United States Patent
Curtiss, III et al.

(10) Patent No.: US 9,598,697 B2
(45) Date of Patent: Mar. 21, 2017

(54) RECOMBINANT BACTERIUM TO DECREASE TUMOR GROWTH

(75) Inventors: Roy Curtiss, III, Paradise Valley, AZ (US); Wei Kong, Phoenix, AZ (US)

(73) Assignee: The Arizona Board of Regents for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/700,591

(22) PCT Filed: May 31, 2011

(86) PCT No.: PCT/US2011/038588
§ 371 (c)(1),
(2), (4) Date: Apr. 15, 2013

(87) PCT Pub. No.: WO2011/150421
PCT Pub. Date: Dec. 1, 2011

(65) Prior Publication Data
US 2013/0209405 A1  Aug. 15, 2013

Related U.S. Application Data

(60) Provisional application No. 61/349,425, filed on May 28, 2010.

(51) Int. Cl.
| | | |
|---|---|---|
| A01N 63/00 | (2006.01) |
| C12N 1/20 | (2006.01) |
| C12N 15/74 | (2006.01) |
| C12R 1/42 | (2006.01) |
| A61K 35/74 | (2015.01) |
| C12N 1/36 | (2006.01) |

(52) U.S. Cl.
CPC .............. *C12N 15/74* (2013.01); *A61K 35/74* (2013.01); *C12N 1/36* (2013.01); *C12R 1/42* (2013.01)

(58) Field of Classification Search
CPC combination set(s) only.
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |
| 5,294,441 A | 3/1994 | Curtiss, III |
| 5,387,744 A | 2/1995 | Curtiss |
| 5,389,368 A | 2/1995 | Curtiss, III |
| 5,424,065 A | 6/1995 | Curtiss, III |
| 5,468,485 A | 11/1995 | Curtiss, III |
| 5,536,658 A | 7/1996 | Shotts, Jr. et al. |
| 5,654,184 A | 8/1997 | Curtiss, III |
| 5,656,488 A | 8/1997 | Curtiss, III |
| 5,672,345 A | 9/1997 | Curtiss, III |
| 5,679,880 A | 10/1997 | Curtiss, III |
| 5,686,079 A | 11/1997 | Curtiss, III |
| 5,817,317 A | 10/1998 | Titball |
| 5,827,705 A | 10/1998 | Dean |
| 5,840,483 A | 11/1998 | Curtiss, III |
| 5,855,879 A | 1/1999 | Curtiss, III |
| 5,855,880 A | 1/1999 | Curtiss, III |
| 5,961,983 A | 10/1999 | Brey et al. |
| 6,024,961 A | 2/2000 | Curtiss, III |
| 6,180,614 B1 | 1/2001 | Davis |
| 6,248,329 B1 | 6/2001 | Chandrashekar et al. |
| 6,350,454 B1 | 2/2002 | Thune |
| 6,383,496 B1 | 5/2002 | Curtiss, III |
| 6,399,074 B1 | 6/2002 | Roland |
| 6,403,094 B1 | 6/2002 | Titball |
| 6,610,529 B1 | 8/2003 | Curtiss, III |
| 6,780,405 B1 | 8/2004 | Curtiss, III |
| 6,872,547 B1 | 3/2005 | Curtiss, III |
| 6,969,513 B2 | 11/2005 | Galen |
| 7,083,794 B2 | 8/2006 | Curtiss, III |
| 7,195,757 B2 | 3/2007 | Curtiss, III |
| 7,205,125 B2 | 4/2007 | Castillo |
| 7,341,860 B2 | 3/2008 | Curtiss, III |
| 7,871,604 B1 | 1/2011 | Curtiss, III |

(Continued)

FOREIGN PATENT DOCUMENTS

| | | |
|---|---|---|
| EP | 0315682 B1 | 12/1993 |
| EP | 0381706 B1 | 4/1995 |

(Continued)

OTHER PUBLICATIONS

Moreno et al. Salmonella as Live Trojan Horse for Vaccine Development and Cancer Gene Therapy. Current Gene Therapy, 2010. 10:56-76.*
Instructions to Authors for the Journal of Bacteriology, 2015. pp. 1-18, downloaded from http://journalitas.asm.org/t/49543 on Feb. 13, 2015.*
Haugen et al. The Natural History of Group I Introns, TRENDS in Genetics, 2005. 21(2): 111-119.*
Kittleson et al. Successes and Failures in Modular Genetic Engineering. Current Opinion in Chemical Biology, 2012. 16:329-336.*
Lefman, J. et al. Three-Dimensional Electron Microscopic Imaging of Membrane Invaginations in *Escherichia coli* Overproducing the Chemotaxis Receptor Tsr. Journal of Bacteriology. Aug. 2004, vol. 186(15), pp. 5052-5061: abstract; p. 5054, col. 1, para 1.

(Continued)

*Primary Examiner* — Christopher M Babic
*Assistant Examiner* — Kimberly A Aron
(74) *Attorney, Agent, or Firm* — McCarter & English, LLP; Elizabeth A. Hanley, Esq.; Marcie B. Clarke

(57) ABSTRACT

A recombinant bacterium capable of reducing tumor growth is provided, wherein said recombinant bacterium is capable of: a. increased expression of a nucleic acid encoding a chemoreceptor that directs chemotaxis towards tumors, b. accumulation in a quiescent tumor, c. hyper-invasion of a tumor, d. reduced fitness in normal tissue, e. enhanced stimulation of the host innate immune responses, f. delivering a tumor specific DNA vaccine vector to a tumor cell, and g. increased bacterium-induced host programmed cell death.

18 Claims, 14 Drawing Sheets

(56) References Cited

U.S. PATENT DOCUMENTS

| | | | |
|---|---|---|---|
| 7,968,101 | B2 | 6/2011 | Kawaoka |
| 8,133,493 | B2 | 3/2012 | Curtiss, III |
| 8,445,254 | B2 | 5/2013 | Curtiss, III et al. |
| 8,465,755 | B2 | 6/2013 | Curtiss, III et al. |
| 2003/0031683 | A1 | 2/2003 | Curtiss, III |
| 2003/0175772 | A1 | 9/2003 | Wang |
| 2004/0077556 | A1 | 4/2004 | Chinery |
| 2004/0101531 | A1 | 5/2004 | Curtiss, III |
| 2004/0120962 | A1 | 6/2004 | Curtiss, III |
| 2004/0137003 | A1 | 7/2004 | Curtiss, III |
| 2004/0203039 | A1 | 10/2004 | Hensel |
| 2005/0036987 | A1 | 2/2005 | Pawelek et al. |
| 2005/0106175 | A1 | 5/2005 | Montaines |
| 2005/0106176 | A1 | 5/2005 | Curtiss, III |
| 2005/0118193 | A1 | 6/2005 | Andino-Pavlovsky et al. |
| 2006/0140975 | A1 | 6/2006 | Curtiss, III |
| 2006/0171917 | A1 | 8/2006 | Campbell |
| 2006/0206961 | A1 | 9/2006 | Cirpus |
| 2006/0233829 | A1 | 10/2006 | Curtiss, III |
| 2006/0234346 | A1 | 10/2006 | Retallack |
| 2006/0275255 | A1 | 12/2006 | Gudkov |
| 2007/0025981 | A1 | 2/2007 | Szalay |
| 2008/0096809 | A1* | 4/2008 | Shai .................... 514/12 |
| 2008/0248066 | A1 | 10/2008 | Dubensky, Jr. |
| 2009/0175829 | A1 | 7/2009 | Forbes et al. |
| 2010/0124558 | A1 | 5/2010 | Curtiss et al. |
| 2010/0154293 | A1 | 6/2010 | Hom et al. |
| 2010/0255022 | A1 | 10/2010 | Prescott et al. |
| 2010/0285592 | A1 | 11/2010 | Curtiss et al. |
| 2010/0317084 | A1 | 12/2010 | Curtiss, III |
| 2011/0033501 | A1 | 2/2011 | Curtiss, III et al. |
| 2011/0256181 | A1 | 10/2011 | Curtiss et al. |
| 2011/0287052 | A1 | 11/2011 | Curtiss, III et al. |
| 2012/0087946 | A1 | 4/2012 | Curtiss, III |
| 2013/0004537 | A1 | 1/2013 | Curtiss, III et al. |
| 2013/0171190 | A1 | 7/2013 | Curtiss, III et al. |

FOREIGN PATENT DOCUMENTS

| | | |
|---|---|---|
| EP | 0465560 B1 | 6/1996 |
| EP | 0500699 B1 | 6/1998 |
| EP | 0558631 B1 | 3/1999 |
| EP | 0433372 B1 | 6/2002 |
| EP | 1030690 B1 | 7/2002 |
| EP | 0556333 B1 | 3/2003 |
| EP | 1326960 B1 | 12/2004 |
| EP | 0832255 B1 | 12/2005 |
| EP | 1537214 B1 | 3/2006 |
| EP | 1292687 B1 | 8/2006 |
| WO | 88/09669 A1 | 12/1988 |
| WO | 89/03427 A1 | 4/1989 |
| WO | 90/02484 A1 | 3/1990 |
| WO | 90/11687 A1 | 10/1990 |
| WO | 90/11688 A1 | 10/1990 |
| WO | 90/12086 A1 | 10/1990 |
| WO | 91/06317 A1 | 5/1991 |
| WO | 92/08486 A1 | 5/1992 |
| WO | 92/09684 A1 | 6/1992 |
| WO | 93/04202 A1 | 3/1993 |
| WO | 94/24291 A2 | 10/1994 |
| WO | 94/24291 A3 | 12/1994 |
| WO | 96/40947 A1 | 12/1996 |
| WO | 99/25387 A1 | 5/1999 |
| WO | 01/83785 A2 | 11/2001 |
| WO | 02/30457 A2 | 4/2002 |
| WO | 01/83785 A3 | 6/2002 |
| WO | 02/059292 A2 | 8/2002 |
| WO | 02/030457 A3 | 1/2003 |
| WO | 02/030457 A3 | 7/2003 |
| WO | 02/059292 A3 | 7/2003 |
| WO | 03/079792 A1 | 10/2003 |
| WO | 03/096812 A1 | 11/2003 |
| WO | 2004/020643 A2 | 3/2004 |
| WO | 2004/020643 A3 | 4/2004 |
| WO | 2005/001069 A1 | 1/2005 |
| WO | 2012087483 A1 | 6/2008 |
| WO | 2008/141226 A2 | 11/2008 |
| WO | 2009/025888 A2 | 2/2009 |
| WO | 2009/046449 A1 | 4/2009 |
| WO | 2009/046451 A1 | 4/2009 |
| WO | 2010/045620 A1 | 4/2010 |
| WO | 2010/078584 A1 | 8/2010 |
| WO | 2010/135563 A1 | 11/2010 |
| WO | 2011/091291 A1 | 7/2011 |
| WO | 2011/150421 A2 | 12/2011 |

OTHER PUBLICATIONS

Takaya, A. et al. The ATP-Dependent Lon Protease of *Salmonella enterica* Serovar Typhimurium Regulates Invasion and Expression of Genes Carried on *Salmonella* Pathogenicity Island 1. Journal of Bacteriology. Jan. 2002, vol. 184(1), pp. 224-232: abstract; p. 225, col. 2, para 2.

Navasa, M., et al. Temperature has reciprocal effect on colanic acid and polysialic acid biosynthesis in *E. coli* K92. Appl Microbiol Biotechnol. Jan. 13, 2009, vol. 82, pp. 721-729: fig 4.

Kong, Q., et al. *Salmonella* Synthesizing 1-Monophosphorylated Lipopolysaccharide Exhibits Low Endotoxic Activity while Retaining its Immunogenicity. J Immunol. Jun. 1, 2011, vol. 187, pp. 412-423: p. 413, col. 1, para 4: p. 415, col. 1, para 1.

Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.

Amann et al., Tightly regulated tac promoter vectors useful for the expression of unfused and fused proteins in *Escherichia coli*. Nucleic acid sequence, 1988. pp. 301-315, vol. 69, No. 2.

Anderson et al., Delivery of the Pertactin/P.69 polypeptide of Bordetella pertussis using an attenuated *Salmonella typhimurium* vaccine strain: expression levels and immune response. Vaccine, 1996, pp. 1384-1390, vol. 14, No. 14.

Aravind et al., The HD domain defines a new superfamily of metal-dependent phosphohydrolases. Trends Biochem Sci, 1998, pp. 469-472, vol. 23.

Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.

Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.

Audia et al., Breaking through the acid barrier: an orchestrated response to proton stress by enteric bacteria. Int J Med Microbiol, 2001, pp. 97-106, vol. 291.

Battesti et al., Acyl carrier protein/SpoT interaction, the switch linking SpoT-dependent stress response to fatty acid metabolism. Mol Microbiol, 2006, pp. 1048-1063, vol. 62.

Blattner et al., The complete genome sequence of *Escherichia coli* K-12. Science, 1997, pp. 1453-1474, vol. 277.

Branger et al., Oral vaccination with different antigens from Yersinia pestis KIM delivered by live attenuated *Salmonella typhimurium* elicits a protective immune response against plague. Adv Exp Med Biol, 2007, pp. 387-399, vol. 603.

Briles et al. The potential for using protein vaccines to protect against otitis media caused by *Streptococcus pneumoniae*. Vaccine, 2000, pp. S87-S95, vol. 19, Suppl 1.

Brubaker, Interleukin-10 and inhibition of innate immunity to Yersiniae: roles of Yops and LcrV (V antigen). Infect Immun, 2003, pp. 3673-3681, vol. 71.

Brubaker, The Vwa+ virulence factor of Yersiniae: the molecular basis of the attendant nutritional requirement for Ca2+. Rev Infect Dis, 1983,pp. S748-S758, vol. 5, Suppl 4.

Brumell et al., (2004) *Salmonella* redirects phagosomal maturation. Curr Opin Microbiol, 2004, pp. 78-84, vol. 7.

Cárdenas et al., Oral immunization using live attenuated *Salmonella* spp. as carriers of foreign antigens. Clin. Microbiol. Rev., 1992, pp. 328-342, vol. 5, No. 3.

(56) References Cited

OTHER PUBLICATIONS

Charnetzky et al., RNA synthesis in Yersinia pestis during growth restriction in calcium-deficient medium. J Bacteriol, 1982, pp. 108-195, vol. 149.
Chatfield et al., Use of the nirB promoter to direct the stable expression of heterologous antigens in Salmonella oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of Yersinia pestis virulence. J Bacteriol, 2005, pp. 8172-8180, vol. 187.
Coombes et al., SseL Is a Salmonella-Specific Translocated Effector Integrated into the SsrB-Controlled Salmonella Pathogenicity Island 2 Type III Secretion System. Infection and Immunity, 2007, pp. 574-580, vol. 75, No. 2.
Cornelis et al., The virulence plasmid of Yersinia, an antihost genome. Microbiol Mol Biol Rev, 1998, pp. 1315-1352, vol. 62.
Curtiss et al. Nonrecombinant and recombinant avirulent Salmonella vaccines for poultry. Vet Immunol Immunopathol, 1996, pp. 365-372, vol. 54.
Curtiss et al., Live oral avirulent Salmonella vaccines. Vet. Microbiol., 1993, pp. 397-405, vol. 37.
Curtiss et al., Recombinant Salmonella vectors in vaccine development. Dev Biol Stand., 1994, pp. 23-33, vol. 82.
Datsenko et al., One-step inactivation of chromosomal genes in Escherichia coli K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in Salmonella typhimurium. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of Yersinia pestis KIM. J Bacteriol, 2002, pp. 4601-4611, vol. 184.
Doggett et al., Delivery of antigens by recombinant avirulent Salmonella strains. Adv. Exp. Med. Biol., 1992, pp. 165-173, vol. 327.
Doublet et al., The murI gene of Escherichia coli is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How Salmonella survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of Salmonella typhimurium are deficient in transductional recombination, DNA repair and plasmid maintenance. Mol. Gen. Genet., 1996, pp. 570-580, vol. 250.
Gentry et al., Mutational analysis of the Escherichia coli spoT gene identifies distinct but overlapping regions involved in ppGpp synthesis and degradation. Mol Microbiol, 1996, pp. 1373-1384, vol. 19.

Gentschev et al., The E. coli alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the Yersinia pestis Yfu ABC inorganic iron transport system. Infect Immun, 2001, pp. 2829-2837, vol. 69.
Gor et al., TH1-TH2: a Procrustean paradigm. Nat Immunol, 2003, p. 503-5, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in Escherichia coli. Mol Microbiol, 1992, pp. 1877-1886, vol. 6.
Hess et al., Secretion of different listeriolysin cognates by recombinant attenuated Salmonella typhimurium: superior efficacy of haemolytic over non-haemolytic constructs after oral vaccination. Microbes Infect., 2000, pp. 1799-1806, vol. 2.
Hohmann et al., Evaluation of a phoP/phoQ-deleted, aroA-deleted live oral Salmonella typhi vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in Xenopus oocytes. Gene, 1988, pp. 301-313, vol. 62, No. 2.
Huang et al., Genome-wide screen of Salmonella nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of Streptococcus pneumoniae. Gene, 2002, pp. 63-71, vol. 284.
In Soo Lee et al., The stationary-phase sigma factor sS (RpoS) is required for a sustained acid tolerance response in virulent Salmonella typhimurium. Molecular Microbiology, 1995, pp. 155-167, vol. 17.
Isoda et al., Expression of a Porphyromonas gingivalis hemagglutinin on the surface of a Salmonella vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of Escherichia coli. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of Streptococcus pneumoniae against lethal infection in mice. Vaccine, 2006, pp. 6225-6231, vol. 24.
Kim et al., Direct transcriptional control of the plasminogen activator gene of Yersinia pestis by the cyclic AMP receptor protein. J Bacteriol, 2007, pp. 8890-8900, vol. 189.
Kolodrubetz et al., Regulation of the L-arabinose transport operons in Escherichia coli. J Mol Biol, 1981, pp. 215-227, vol. 151, No. 2.
Kwon et al., Salmonella-based vaccines for infectious diseases. Expert Review of Vaccines, 2007, pp. 147-152, vol. 6.
Lange et al., Identification of a central regulator of stationary-phase gene expression in Escherichia coli. Mol Microbiol, 1991, pp. 49-59, vol. 5.
Lee et al., Regulation of L-arabinose transport in Salmonella typhimurium LT2. Mol Gen Genet, 1982, pp. 136-141, vol. 185, No. 1.
Lee et al., Surface-displayed viral antigens on Salmonella carrier vaccine. Nat Biotechnol, 2000, pp. 645-648, vol. 18, No. 6.

(56) References Cited

OTHER PUBLICATIONS

Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spv and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in Yersinia pestis. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the Yersinia pestis V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of Yersinia pestis is posttranscriptional. J Bacteriol, 2004, pp. 1638-1647, vol. 186.
Petersen et al., Essential role for cyclic AMP and its receptor protein in Yersinia enterocolitica virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. For mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
PCT/US/2008/063303 (WO2008/141226)—International Search Report and Written Opinion of the International Searching Authority, Nov. 26, 2008.
U.S. Appl. No. 12/759,842, Office Action dated Oct. 4, 2011.
PCT/US2008/078991 (WO2009/046449)—International Search Report and Written Opinion of the International Searching Authority, Dec. 15, 2008.
PCT/US2008/078993 (WO2009/046451)—International Search Report and Written Opinion of the International Searching Authority, Dec. 15, 2008.
PCT/US2010/035630 (WO2010/135563)—International Search Report and Written Opinion of the International Searching Authority, Sep. 29, 2010.
PCT/US2009/061100 (WO2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO2011/091291)—International Search Report and Written Opinion of the International Searching Authority, Apr. 11, 2011.
PCT/US2011/038588 (WO2011/150421)—International Search Report and Written Opinion of the International Searching Authority, Nov. 22, 2011.
PCT/US98/24295—International Preliminary Examination Report, Dec. 26, 2000 (WO/1999/025387).
PCT/US2001/013915—International Preliminary Examination Report, Aug. 16, 2002 (WO/2001/083785).
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.

(56) References Cited

OTHER PUBLICATIONS

European Patent Application No. 90905859.6 (EP0465560), Intention to Grant dated Jan. 4, 1995 by A. Ormerod.
European Patent Application No. 90905859.0 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant Sep. 27, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office Action dated Jan. 17, 2007.
European Patent Application No. 03721711.4 (EP1499191), Office Action dated Mar. 23, 2009.
European Patent Application No. 03721711.4 (EP1499191), Office Action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office Action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al., OmpR regulates the stationary-phase acid tolerance response of *Salmonella enterica* serovar Typhimurium. J. Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low-pH-inducible, PhoPQ-dependent acid tolerance response protects *Salmonella typhimurium* against inorganic acid stress. J. Bacteriol, 1998, pp. 2409-2417, vol. 180.
Bertani, Studies on lysonucleic acid sequencesis. I. The mode of phage liberation by lysogenic *Escherichia coli*. J. Bacteriol, 1951, pp. 293-300, vol. 62, No. 3.
Black et al., Aspartic-semialdehydedehydrogenase and aspartic-semialdehyde, J. Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun. 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J. Immunol., 1998, pp. 5525-5533, vol. 161.
Buchmeier, et al., DNA repair is more important than catalase for *Salmonella* virulence in mice. J. Clin. Invest., 1995, pp. 1047-1053, vol. 95.

(56) References Cited

OTHER PUBLICATIONS

Bumann, Regulated antigen expression in live recombinant *Salmonella enterica* serovar Typhimurium strongly affects colonization capabilities and specific CD4(+)-T-cell responses. Infect. Immun, 2001. pp. 7493-7500, vol. 69, No. 12.
PCT/US2011/061896 (WO2012/087483)—International Search Report and Written Opinion of the International Searching Authority, Apr. 5, 2012.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Byl et al, Sequence of the Genomore of *Salmonella* Bacteriophage P22. Journal of Bacteriology, 2000, pp. 6472-6484, vol. 182, 22.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5517, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Seroavar Typhimurium. Journal of Bacteriology, 2009, pp. 1278-1292, vol. 191, No. 4.
U.S. Appl. No. 12/615,872, Office Action dated Mar. 14, 2012.
Collins et al, Mutation at rfc or pmi Attenuate *Salmonella typhimurium* Virulence for Mice. Infect and Immun, 1991, pp. 1079-1085, vol. 59, No. 3.
Curtiss et al., Stabilization of Recombinant Avirulent Vaccine Strains in vivo. Res. Microbiol., 1990, pp. 797-805, vol. 141.
Curtiss et al, Avirulent *Salmonell typhimurim* cyc crp oral vaccine strains expressing a *streptococcal* colonization and virulence antigen. Vaccine, 1988, pp. 155-160, vol. 6.
Darzins et al., Nucleotide sequence analysis of the phosphomannose isomerase gene (pmi) of Pseudomonas aeruginose and comparison with the corresponding *Escherichia coli* gene manA. Gene, 1986, pp. 293-302, vol. 42.
Doggett et al., Immune Responses to *Streptococcus sobrinus* Surface Protein Antigen A Expressed by Recombinant *Salmonella typhimurium*. Infect and Immun, 1993, pp. 1859-1866, vol. 61, No. 5.
Egan et al., A Regulatory Cascade in the Induction of rhaBAD. J. Mol. Biol., 1993, pp. 87-98, vol. 234.
Guzman et al., Tight regulations, Modulations, and High-Level Expression by Vectors Containing the Arabinose Pbad Promotor. Journal of Bacteriology, 1995, pp. 4121-4130, vol. 177, No. 14.
Kennedy et al., Attenuation and Immunogenicity of cya crp Derivatives of *Salmonella choleraeuis* in Pigs. Infect Immun, 1999, pp. 4628-4636, vol. 67, No. 9.
Nickerson et al., Role of Sigma Factor RpoS in Initial Stages of *Salmonella typhimurium* Infection. Infect Immun, 1997, p. 1814-1823, vol. 65, No. 5.
Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.
Schodel, Recombinant Avirulent *Salmonellae* as Oral Vaccine Carriers. Infection, 1992, vol. 20, pp. 1-12, No. 1.
Siegele et al., Gene Expression from plasmids containing the araBAD promoter at subsaturating inducer concentrations represents mixed populations. PNAS, 1997, pp. 8168-8172, vol. 94.
Song et al., Organization and Regulation of the d-Xylose Operons in *Escherichia coli* K-12: XyIR Acts as a Transcriptional Activator. Journal of Bacteriology, 1997, pp. 7025-7032, vol. 179, No. 22.
Srinivasan et al., Oral Immunization with Attenuated *Salmonella* Expressing Human Sperm Antigen Induces Antibodies in Serum and the Reproductive Tract. Biology of Reproduction, 1995, p. 462-471 vol. 53.
PCT/US2008/063293 (WO 2009/025888)—International Search Report and Written Opinion of the International Searching Authority, Feb. 12, 2009.
Mesika et al., A Regulated, NFkB—Assisted Import of Plasmid DNA into Mammalian Cell Nuclei, Molecular Therapy, vol. 3, No. 5, May 2001, pp. 653-657.
Quenee, et al., Yersinia pestis caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012 (Ginny Portner).
U.S. Appl. No. 13/006,072, Office Action dated Dec. 11, 2012 (Ja'Na Hines).
Kong. Improving DNA Vaccine Vector for Efficient Vaccine Delivery using Live Attenuated Bacterial Carrier. American Society for Microbiology, T-010, 2008, vol. 108, p. 668.
Whitworth et al., Expression of the Rickettsia prowazekii pld or tlyC Gene in *Salmonella enterica* Serovar Typhimurium Mediates Phagosomal Escape, Infection and Immunity, 2005, vol. 73(10), pp. 6668-6673.
Folkesson et al., Components of the peptidoglycan-recycling pathway modulate invasion and intracellular survival of *Salmonella enterica* serovar Typhimurium. Cellular Microbiology, 2005, vol. 7(1) pp. 147-155.
U.S. Appl. No. 12/599,655, Office Action dated Mar. 12, 2013.
U.S. Appl. No. 12/681,711, Office Action dated Nov. 28, 2012.
U.S. Appl. No. 12/789,869, Office Action dated Jun. 3, 2014.
U.S. Appl. No. 13/088,141, Office Action dated Apr. 24, 2014.
U.S. Appl. No. 13/574,718, Office Action dated Sep. 6, 2013.
U.S. Appl. No. 13/574,718, Office Action dated Apr. 28, 2014.
U.S. Appl. No. 13/898,241, Office Action dated Apr. 17, 2014.
CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
U.S. Appl. No. 13/006,072, Office Action dated Apr. 19, 2012.

(56) References Cited

OTHER PUBLICATIONS

Sun et al., Highly efficient method for introducing successive multiple scarless gene deletions and markerless gene insertions into the Yersinia pestis chromosome. Appl Environ Microbiol, 2008, pp. 4241-4245, vol. 74.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Waltman et al., Biochemical Characteristics of *Edwardsiella ictaluri*. Applied and Enviornmental Microbiology, 1986, pp. 101-104, vol. 51, No. 1.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Dean, 1997. Import of plasmid DNA into the nucleus is sequence specific. Exp. Cell Res., 1997, pp. 293-302, vol. 230.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of Shigella sonnei form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella typhimurium* to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella typhi* CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.
Greenwood, The epidemiology of pneumococcal infection in children in the developing world. Philos. Trans. R. Soc. Lond. B. Biol. Sci., 1999, pp. 777-85, vol. 354.
Gulig et al., Plasmid-associated virulence of *Salmonella typhimurium*. Infect Immun, 1987, pp. 2891-2901, vol. 55.
Hall et al., The role of fur in the acid tolerance response of *Salmonella typhimurium* is physiologically and genetically separable from its role in iron acquisition. J Bacteriol, 1996, pp. 5683-5691, vol. 178.
Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.
Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.
Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.
Hoffmann et al., "Ambisense" approach for the generation of influenza A virus: vRNA and mRNA synthesis from one template. Virology, 2000, pp. 310-317, vol. 267.
Hohmann et al., Macrophage-inducible expression of a model antigen in *Salmonella typhimurium* enhances immunogenicity. Proc Natl Acad Sci U S A, 1995, pp. 2904-2908, vol. 92, No. 7.
Hollingshead et al., Diversity of PspA: mosaic genes and evidence for past recombination in *Streptococcus pneumoniae*. Infect. Immun., 2000, pp. 5889-5900, vol. 68.
Hopkins et al., A recombinant *Salmonella typhimurium* vaccine induces local immunity by four different routes of immunization. Infect Immun, 1995, pp. 3279-3286, vol. 63.
Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.
Kang et al., Immune responses to recombinant pneumococcal PspA antigen delivered by live attenuated *Salmonella enterica* serovar typhimurium vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Hurme et al, A Proteinaceous Gene Regulator Thermameter in *Salmonella*. Cell, 1997, pp. 55-64, vol. 90.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.

(56) References Cited

OTHER PUBLICATIONS

Konjufca et al., A Recombinant Attenuated *Salmonella enterica* Serovar Typhimurium Vaccine Encoding Eimeria acervulina Antigen Offers Protection against E. acervulina Challenge. Infect. Immun., 2006, pp. 6785-6796, vol. 74.

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. USA, 1981, pp. 752-756, vol. 78.

Li et al. A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J. Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol. 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al. Complete genome sequence of *Salmonella enterica* serovar Typhimurium LT2. Nature, 2001, pp. 852-856, vol. 413, No. 6858.

McDaniel et al., Monoclonal antibodies against protease sensitive pnuemococcal anitigens can protect mice form fatal infection with *Streptococcus pneumoniae*. J. Exp. Med., 1984, pp. 368-397, vol. 160.

McDaniel et al., Use of insertional inactivation to facilitate studies of biological properties of pneumococcal surface protein A (PspA). J. Exp. Med. 1987, pp. 381-394, vol. 165.

Miller et al., A novel suicide vector and its use in construction of insertion mutations: osmoregulation of outer membrane proteins and virulence determinants in Virbrio cholerae requires toxR. J. Bacteriol, 1988, pp. 2575-2583, vol. 170.

Miller et al, Bacteriophage T4 genome. Microbiol. Mol. Biol. Rev, 2003, pp. 86-156, vol. 67, No. 1.

Molinari et al., The annual impact of seasonal influenza in the US; measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expresses in attenuated *Salmonella typhimurium* elicit mucosal and systemic neutralizing antibodies in mice. Infect. Immun., 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect. Immun. 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of *Streptococcus pneumoniae* D39 in a Mouse Model. Infect. Immun. 2007, pp. 1843-1851, vol. 75.

Osterholm, Preparing for the next pandemic, N. Engl. J. Med. 2005, pp. 1839-1842, vol. 352.

Ozaki et al., Generation of high-yielding influenza A viruses in African green monkey kidney (Vero) cells by reverse genetics. J. Virol. 2004, pp. 1851-1857, vol. 78.

Park et al., Engineered viral vaccine constructs with dual specificity: avian influenza and Newcastle disease. Proc. Natl. Acad. Sci. USA, 2006, pp. 8203-8208, vol. 103.

Pascual et al, Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.

Pashine et al., Th1 dominance in the immune response to live *Salmonella typhimurium* requires bacterial invasiveness but not persistence. Int. Immunol., 1999, pp. 481-489, vol. 11.

Peterson et al., RpoS proteolysis is regulated by a mechanism that does not require the SprE (RssB) response regulator phosphorylation site. J Bacteriol, 2004, pp. 7403-7410, vol. 186.

Pizarro-Cerda et al., The bacterial signal molecule, ppGpp, regulates *Salmonella* virulence nucleic acid sequence expression. Mol Microbiol, 2004, pp. 1827-1844, vol. 52, No. 6.

Prouty et al., *Salmonella enterica* serovar Typhimurium invasion is repressed in the presence of bile. Infect Immun, 2000, pp. 6763-6769, vol. 68.

Quinlivan et al., Attenuation of equine influenza viruses through truncations of the NS1 protein. J. Virol., 2005, pp. 8431-8439, vol. 79.

Rand, Crystal violet can be used to visualize DNA bands during gel electrophoresis and to improve cloning efficiency. Tech Tips Online, 1996 http://www.science-direct.com/science/journal/13662120.

Roberts et al., Oral vaccination against tetanus: comparison of the immunogenicities of *Salmonella* strains expressing fragment C fromt he nirB and htrA promoters. Infect. Immun. 1998, pp. 3080-3087, vol. 66.

Romeo et al, Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.

Sadler et al., A perfectly symmetric lac operator binds the lac repressor very tightly. Proc Natl Acad Sci USA 1983, pp. 6785-6789, vol. 80, No. 22.

Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.

Hori et al, Construction of self disruptive Bacillus megaterium in response to substrate exhaustion for polyhydroxybutyrate production. Appl Microbiol Biotechnol, 2002, pp. 211-216, vol. 59.

Houng et al., Expression of Vi antigen in *Escherichia coli* K-12: characterization of ViaB form Citrobacter freundii and identity of ViaA with RcsB J. Bacterio, 1992, pp. 5910-5915, vol. 174, No. 18.

(56) References Cited

OTHER PUBLICATIONS

Schuchat et al, Bacterial meningitis in the United States in 1995. Active Surveillance Team. N. Engl. J. Med., 1997, pp. 970-976, vol. 337.
Schulman et al., Independent variation in nature of hemagglutinin and neuraminidase antigens of influenza virus: distinctiveness of hemagglutinin antigen of Hong Kong—68 virus. Proc. Natl. Acad. Sci. USA, 1969, pp. 326-333, vol. 63.
Simonsen et al., The impact of influenza epidemics of hospitalizations. J. Infect. Dis., 2000, pp. 831-837, vol. 181.
Rytkonen et al., SseI, a *Salmonella* deubiquitinase required for macrophase killing and virulence. PNAS, 2007, vol. 104 (pp. 3502-3507).
Ribeiro et al., The role of Polyadenylation Signal Secondary Structures on the Resistance of Plasmid Vectors to Nucleases. J. Gene Med., vol. 6, 2004 (pp. 565-573).
Wang et al., Hemagglutinin (HA) Proteins from H1 and H3 Serotypes of Influenza A Viruses Require Different Antigen Designs for the Induction of Optimal Protective Antibody Responses as Studied by Codon—Optimized HA DNA Vaccines. Journal of Virology, 2006. vol. 80 (p. p. 11628-11637).
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of Yersinia pestis is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in Yersinia pestis include structural genes for outer membrane proteins. Infect Immun, 1986, pp. 445-454, vol. 51.
Sun et al., The role of relA and spoT in Yersinia pestis KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in *Salmonella*. Proc Natl Acad Sci U S A, 2001, pp. 15264-15269, vol. 98.
Viboud et al., Yersinia outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.

Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in Yersinia pestis. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in Rhodococcus opacus PD630 and *Mycobacterium smegmatis* mc2155, and provides an anchor to target other proteins. Microbiology, 2006, pp. 3271-3280, vol. 152.
Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.
U.S. Appl. No. 13/302,575, Office Action dated Sep. 25, 2012.
Morita et al., Antibacterial Activity of Bacillus amyloliquefaciencs Phage Endolysin without Holin Conjugation. Journal of Biosciences and Bioengineering, 2001, pp. 469-473, vol. 91, No. 5.
U.S. Appl. No. 13/302,575, Office Action dated Jun. 18, 2013.
Stevens, Immunization with the C-Domain of alpha-Toxin Prevents Lethal Infection, Localizes Tissue Injury, and Promotes Host Responses to Challenge with Clostridium perfringens. JID, 2004, pp. 767-773, vol. 190.
Verjan et al, Genetic Loci of Major Antigenic Protein Genes of Edwardsiella tarda. Applied and Environmental Microbiology, 2005, pp. 5654-5658, vol. 71, No. 9.
U.S. Appl. No. 12/599,655 Office Action dated Jul. 2, 2012.
U.S. Appl. No. 12/681,721, Office Action dated May 24, 2012.
U.S. Appl. No. 12/759,842, Office Action dated Jun. 7, 2012.
Ellis, New Technologies for Making Vaccines. Vaccines, 1988, pp. 568-574, Chapter 29, WB Saunders Company, United States.
Greenspan et al, Defining eptiopes: It's not as easy as it seems. Nature Biotechnology, 1999, pp. 936-937, vol. 17.
Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.
U.S. Appl. No. 12/615,872 Office Action dated Oct. 23, 2012.
Bittner et al., RpoS and RpoN are involved in the growth-dependent regulation of rfaH transcription and O antigen expression in *Salmonella enterica* serovar Typhi, Microbial Pathogenisis. vol. 36, 2004 (p. 19).
Liu et al., Nickel-inducible lysis system in *Synechocystit* sp. PCC 6803. PNAS, vol. 106, 2009, pp. 21550-21554.
Liu et al.,$CO_2$—limitation-inducible Green Recovery of fatty acids from cyanobacterial biomass. PNAS, vol. 108, 2011 pp. 6905-6908.

\* cited by examiner

SEQUENCE LISTING

<160> NUMBER OF SEQ ID NOS: 1

<210> SEQ ID NO 1
<211> LENGTH: 74
<212> TYPE: DNA
<213> ORGANISM: Artificial Sequence
<220> FEATURE:
<223> OTHER INFORMATION: HOMO SAPIENS

<400> SEQUENCE: 1
ggggactttc cggggactttt cctccccacg cgggggactt tccgccacgg gcggggactt      60
tccggggact ttcc      74

RECOMBINANT BACTERIUM TO DECREASE TUMOR GROWTH

GOVERNMENTAL RIGHTS

This invention was made with government support under R01 AI065779, R01 AI056289, and R21 CA152456-01 awarded by the National Institutes of Health. The government has certain rights in the invention.

FIELD OF THE INVENTION

The invention encompasses a recombinant bacterium capable of reducing tumor size.

BACKGROUND OF THE INVENTION

Conventional therapies for cancer as radiotherapy and chemotherapy are characterized by poor survival rates in many forms of cancer. This is due to multiple factors including the development of drug-resistant tumor cells and the presence of undetectable micrometastases at the time of diagnosis and treatment. The other substantial limitation of conventional cancer chemotherapy and radiotherapy is the toxicity of these agents to normal tissue. A major challenge in treating cancer is the difficulty of bringing therapy to poorly perfused areas of solid tumors, which are often most resistant to chemo- and radiotherapy. This has prompted the development of many new approaches for the treatment of cancer, including the delivery of anti-cancer genes to the tumor site in various gene therapy protocols. These genetic approaches include delivering genes encoding pro-drug activating enzymes, cytotoxic, antiangiogenic proteins or cell-targeted toxins to the tumors. However, current gene therapy strategies require local administration of vectors, which limits their usefulness. Hence, there is a need in the art for an effective and largely non-toxic therapy to fight tumor growth and metastasis.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
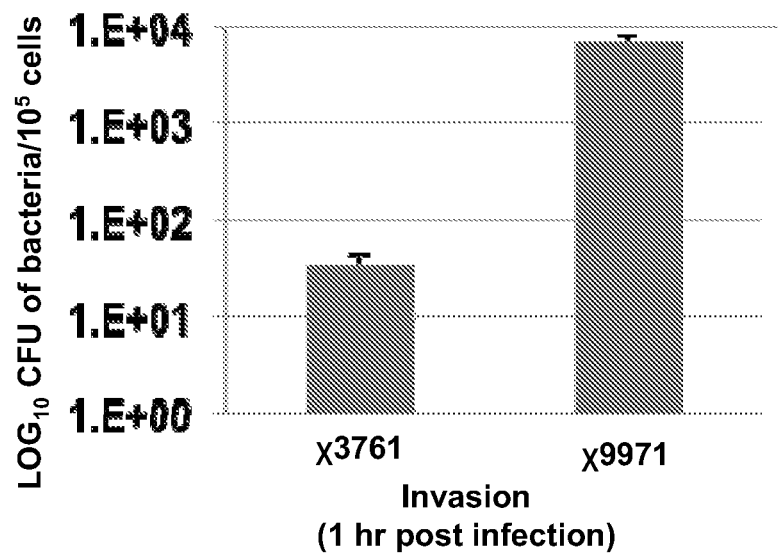
FIG. 1. Invasion (A) and replication (B) of *S. Typhimurium* strains in Int-407 cell line.
Figure 1:
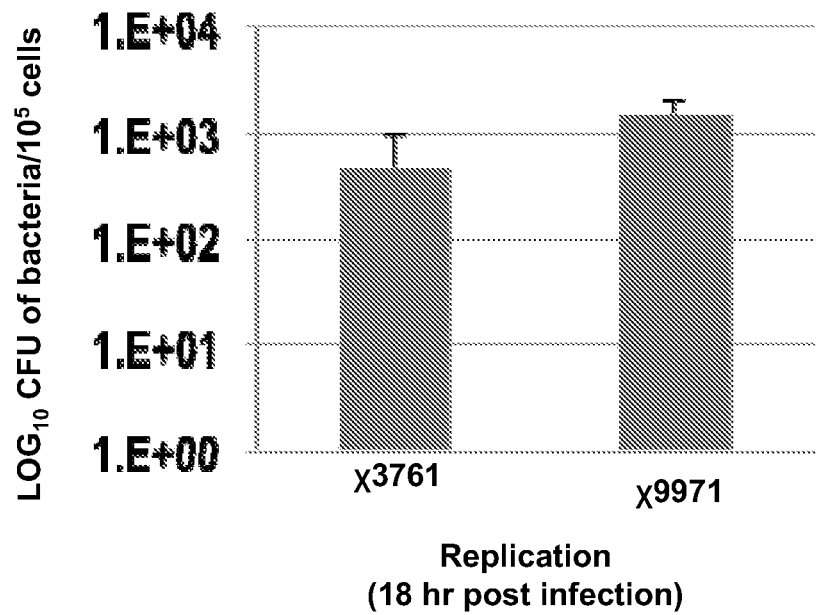

The present invention provides a recombinant bacterium that may be used to inhibit the growth of a tumor or tumor cell. In addition, the invention encompasses methods of use thereof.

I. Recombinant Bacterium

A recombinant bacterium of the invention is typically an anaerobic bacterium. An anaerobic bacterium may be an obligate anaerobe (e.g. a bacterium from the genera *Bacteroides*, *Bifidobacteria*, or *Clostridium*) an aerotolerant bacterium (e.g. a bacterium from the genus *Enterococci*), or a facultative anaerobe (e.g. a bacterium from the family Enterobacteriaceae, the genus *Streptococcus*, the genus *Lactobacillus*, the genus *Staphylococcus*, or the genus *Corynebacterium*). The Enterobacteriaceae family comprises species from the following genera: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Ledercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. In certain embodiments, the recombinant bacterium is typically a pathogenic species of the *Enterobaceteriaceae*. Due to their clinical significance, *Escherichia coli, Shigella, Edwardsiella, Salmonella, Citrobacter, Klebsiella, Enterobacter, Serratia, Proteus, Morganella, Providencia* and *Yersinia* are considered to be particularly useful. In other embodiments, the recombinant bacterium may be a species or strain commonly used for a vaccine.

Some embodiments of the instant invention comprise a species or subspecies of the *Salmonella* genera. For instance, the recombinant bacterium may be a *Salmonella enterica* serovar. In an exemplary embodiment, a bacterium of the invention may be derived from *S. enterica* serovar *Typhimurium*, hereafter referred to as *S. Typhimurium*, and also from *S. Typhi, S. paratyphi, S. Enteritidis, S. Choleraesius, S. Arizona*, or *S. Dublin*. In an exemplary embodiment, the recombinant bacterium is derived from *S. Typhimurium*.

A bacterium of the invention may comprise one or more mutations as detailed below. In particular, a bacterium may comprise one or more mutations to increase invasiveness, to maximize bacterium localization in tumor quiescence, and to reduce bacterium normal tissue fitness (section (a) below), one or more mutations to enhance the stimulation of host innate immune responses (section (b) below), one or more mutations to increase bacterium-induced host programmed cell death (section (c) below), one or more mutations to induce lysis of the bacterium (section (d) below), one or more vectors to express a nucleic acid encoding an antigen or effector protein (section (e) below), one or more mutations to attenuate the bacterium (section (f) below), and/or one or more mutations to enhance the performance of the bacterium as a tumor therapy (section (g) below).

(a) Hyper-Invasiveness and Maximized Localization in Tumors

A recombinant bacterium of the invention may also be hyper-invasive. As used herein, "hyper-invasive" refers to a bacterium that can invade a tumor more efficiently than a wild-type bacterium of the same strain. Invasion may be determined by methods known in the art, e.g. CFUs/g of tumor tissue.

In one embodiment, a recombinant bacterium of the invention may comprise a mutation to increase the expression of a nucleic acid encoding a chemoreceptor that directs chemotaxis towards tumors or increases penetration of tumors. For instance, in one embodiment, the expression of the nucleic acid encoding the aspartate and maltose receptor, e.g. tar, may be increased. In particular, the promoter of the nucleic acid encoding the receptor may be replaced with a constitutive promoter. By way of non-limiting example, a bacterium may comprise a $\Delta P_{tar}::P_{trc\ \Delta lacO888}$ tar mutation. This allows constitutive expression of tar, even when lacI is expressed. In another embodiment, the expression of the nucleic acid encoding the serine receptor, e.g. tsr, may be increased. In particular, the promoter of the nucleic acid encoding the receptor may be replaced with a constitutive promoter. By way of non-limiting example, a bacterium may comprise a $\Delta P_{tsr}::P_{trc\ \Delta lacO888}$ tsr mutation. This allows constitutive expression of tsr, even when lacI is expressed. Additionally, the expression of a nucleic acid encoding a chemoreceptor may be modified by altering the codons of the chemoreceptor nucleic acid to optimize expression in the recombinant bacterium, and/or to alter the translational efficiency of the mRNA and/or to increase the stability of the mRNA.

In certain embodiments, a recombinant bacterium may comprise a mutation that decreases the expression of a nucleic acid encoding a chemoreceptor that directs chemotaxis towards necrosis. This allows bacterial accumulation in a quiescent tumor, as opposed to necrotic cells. For instance, the expression of the nucleic acid encoding the ribose/galactose receptor, e.g. trg, may be decreased. In particular, the trg sequence may be deleted or mutated to prevent or decrease expression of the nucleic acid or translation of the nucleic acid into the corresponding protein. Non-limiting examples of suitable mutations may include the Δtrg and the $\Delta P_{trg}::rhaRS-P_{rhaB}$ trg mutations, which will result in cessation of Trg synthesis in vivo due to the lack of rhamnose. In one embodiment, a bacterium of the invention may comprise both a mutation that increases the expression of one or more nucleic acids that encode a chemoreceptor and a mutation that decreases the expression of one or more different nucleic acids that encode a chemoreceptor.

In another embodiment, a recombinant bacterium may comprise a mutation that decreases the fitness of the bacterium in a normal cell (as opposed to a tumor cell). For instance, a bacterium may comprise a mutation that eliminates the production of adenosine monophosphate (AMP) from inosine monophosphate (IMP). For instance, the S. Typhimurium purA gene may be deleted resulting in a purine-deficient auxotroph. Such a mutant could grow in tumor associated necrotized tissue in vivo, but would have very restricted growth in healthy tissues, which have a very limited supply of purines.

In other embodiments, a recombinant bacterium may further comprise a mutation that increases expression of hilA. For instance, the promoter of hilA may be mutated to enable constitutive expression of hilA. A non-limiting example may include a $\Delta P_{hilA}::P_{trc\Delta lacO}$ hilA mutation, such as $\Delta P_{hilA}::P_{trc\Delta lacO888}$ hilA. Such a mutation replaces the wild-type hilA promoter with the $P_{trc}$ promoter that lacks the lacO operator sequence. This allows constitutive expression of hilA, even when lacI is expressed. Alternatively, deletion of the lrp nucleic acid sequence may be used to increase hilA expression. In another alternative embodiment, a recombinant bacterium may comprise a $\Delta P_{hilA}::P_{hilA256}$ hilA mutation.

(b) Enhanced Stimulation of the Host Innate Immune Responses

The human immune system naturally grows stronger while fighting bacteria, including Salmonella. It is widely believed that one of the main triggers of host inflammation is the recognition of microbial products by receptors of the innate immune system. Consequently, in some embodiments, a recombinant bacterium of the invention may be capable of stimulation of innate immune responses. In an exemplary embodiment, the bacterium is capable of stimulating enhanced host innate immune responses, compared to a wild-type bacterium of the same strain.

In one embodiment, a recombinant bacterium of the invention may overexpress a guanidyl nucleotide exchange factor (e.g. SopE2) and/or an inositol polyphosphatase (e.g. SopB), that activate Rho-family GTPases in a functionally redundant manner to mediate the innate immune responses. In some embodiments, the native promoter of such nucleic acid sequences may be replaced with $P_{trc}$ to enable the regulated delayed synthesis of SopE2 and/or SopB. In certain embodiments, the start codon of the sopE2 and/or sopB genes may be modified to alter its expression level. For instance, the start codon may be changed from GTG to ATG. In addition, the second and third codons can be made more A rich to further increase translation efficiency.

(c) Increased Bacterium-Induced Host Programmed Cell Death

Programmed cell death of a host cell invaded by a bacterium of the invention is advantageous if the host cell is a tumor cell. Consequently, in some embodiments, a recombinant bacterium of the invention may be capable of increased bacterium-induced host programmed cell death compared to a wild-type bacterium of the same strain. Non-limiting examples of bacterium-induced host programmed cell death may include apoptosis and pyroptosis. Methods of detecting and measuring bacterium-induced host programmed cell death are known in the art.

In one embodiment, a bacterium of the invention capable of increasing bacterium-induced host programmed cell death may comprise a mutation that causes over-synthesis of a bacterial protein or effector, after the bacteria accumulate in tumor cells, to affect a pathway inducing apoptosis/pyroptosis. Non-limiting examples of such a mutation may include mutations causing in vivo upregulation of a deubiquitinase-encoding nucleic acid sequence, such as Salmonella sseL, and/or a Toll IL1 Receptor (TIR)-like protein A (TIR-like protein A) nucleic acid sequence (e.g. the Salmonella Enteritidis tlpA), and/or a member of the YopJ/Avr family (e.g. the Salmonella Typhimurium avrA). In particular, a recombinant bacterium of the invention may comprise a mutation that increases the tumor specific expression of *S. Typhimurium* tlpA. By way of non-limiting example, the ansB promoter, which is preferentially activated in tumor cells, may be operably linked to tlpA. Also, the SD sequence of tlpA may be modified to facilitate tumor-specific synthesis of TlpA. For instance, the sequence may be modified to AGGA. In certain embodiments, a bacterium may be capable of regulated lysis, such that the bacterium releases the increased amounts of TlpA upon lysis, thereby increasing bacterium-induced host programmed cell death.

In other embodiments described herein, a recombinant bacterium of the invention may also be used to deliver a nucleic acid vaccine vector, such that the vaccine vector encodes a nucleic acid sequence that increases bacterium-induced host programmed cell lysis. For instance, the vaccine vector may encode Fas ligand (FasL) and/or the tumor necrosis factor (TNF)-related apoptosis-inducing ligand (TRAIL). This is discussed in more detail in section (e) below.

(d) Lysis

In another embodiment, a recombinant bacterium of the invention is capable of regulated lysis. Lysis of the bacterium within the host cell may release a bolus of antigen, or alternatively, may release a nucleic acid vaccine vector for transcription by the tumor cell. Lysis also provides a means of biocontainment.

In some embodiments, a recombinant bacterium capable of regulated lysis may comprise a mutation in a required constituent of the peptidoglycan layer of the bacterial cell wall. For instance, the bacterium may comprise a mutation in a nucleic acid sequence encoding a protein involved in muramic acid synthesis, such as murA. It is not possible to alter murA by deletion, however, because a ΔmurA mutation is lethal and can not be isolated. This is because the missing nutrient required for viability is a phosphorylated muramic acid that cannot be exogenously supplied since enteric bacteria cannot internalize it. Consequently, the murA nucleic acid sequence may be altered to make expression of murA dependent on a nutrient (e.g., arabinose) that can be supplied during the growth of the bacterium. For example, the alteration may comprise a $\Delta P_{murA}$::TT araC $P_{BAD}$ murA deletion-insertion mutation. During in vitro growth of the bacterium, this type of mutation makes synthesis of muramic acid dependent on the presence of arabinose in the growth medium. During growth of the bacterium in a host, however, arabinose is absent. Consequently, the bacterium is non-viable and/or avirulent in a host unless the bacterium further comprises at least one extrachromosomal vector comprising a nucleic acid sequence, that when expressed, substantially functions as murA. Recombinant bacteria with a $\Delta P_{murA}$::TT araC $P_{BAD}$ murA deletion-insertion mutation grown in the presence of arabinose exhibit effective colonization of effector lymphoid tissues after oral administration prior to cell death due to cell wall-less lysing.

Similarly, in various embodiments a recombinant bacterium may comprise the araC $P_{BAD}$ c2 cassette inserted into the asdA nucleic acid sequence that encodes aspartate semialdehyde dehydrogenase, a necessary enzyme for DAP synthesis, a required component of the peptidoglycan layer of the bacterial cell wall. The chromosomal asdA nucleic acid sequence is typically inactivated to enable use of plasmid vectors encoding the wild-type asdA nucleic acid sequence in the balanced-lethal host-vector system. This allows stable maintenance of plasmids in vivo in the absence of any drug resistance attributes that are not permissible in live bacterial vaccines.

In one embodiment, ΔasdA27::TT araC $P_{BAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{BAD}$ c2 has the 1104 base-pair asdA nucleic acid sequence deleted (1 to 1104, but not including the TAG stop codon) and the 1989 base-pair fragment containing T4 iplll TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA. In some additional embodiments, the C2 repressor binding sites may be modified so that as C2 decreases the P22 $P_R$ araBAD nucleic acid sequences are expressed at a higher level than in wild-type strains.

In exemplary embodiments, the bacterium may comprise a mutation in the murA nucleic acid sequence encoding the first enzyme in muramic acid synthesis and the asdA nucleic acid sequence essential for DAP synthesis. By way of non-limiting example, these embodiments may comprise the chromosomal deletion-insertion mutations ΔasdA19::TT araC $P_{BAD}$ c2 or ΔasdA27::TT araC $P_{BAD}$ c2 and $\Delta P_{murA7}$::TT araC $P_{BAD}$ murA or $\Delta P_{murA12}$::TT araC $P_{BAD}$ murA or $\Delta P_{murA25}$::TT araC $P_{BAD}$ murA. This host-vector grows in LB broth with 0.1% L-arabinose, but is unable to grow in or on media devoid of arabinose since it undergoes cell wall-less death by lysis. In another embodiment, the onset of programmed lysis may be delayed about one cell division by including a Δ(araC $P_{BAD}$)-18::P22 $P_R$ araBAD mutation, which initially prevents breakdown of accumulated arabinose at the time of inoculation. Later, however, this mutation allows breakdown of residual arabinose to reduce the likelihood of expressin any araC $P_{BAD}$ regulated nucleic acid sequences.

Bacterium that comprise these mutations also comprise a plasmid that contains a nucleic acid sequence that substitutes for murA and asdA. This allows the bacterium to grow in permissive environments, e.g. when arabinose is present. For instance plasmid vector pYA3681 contains the murA nucleic acid sequence (with altered start codon sequences from ATG to GTG to decrease translation efficiency) under the control of an araC $P_{BAD}$ promoter. The second nucleic acid sequence under the direction of this promoter is the asdA nucleic acid sequence (with altered start codon sequences from ATG to GTG to decrease translation efficiency). The P22 $P_R$ promoter is in the anti-sense direction of both the asdA nucleic acid sequence and the murA nucleic acid sequence. The P22 $P_R$ is repressed by the C2 repressor made during growth of the strain in media with arabinose (due to the ΔasdA::TT araC $P_{BAD}$ c2 deletion-insertion). However C2 concentration decreases due to cell division in vivo to cause $P_R$ directed synthesis of anti-sense mRNA to further block translation of asdA and murA mRNA. The araC $P_{BAD}$ sequence is also not from *E. coli* B/r as originally described but represents a sequence derived from *E. coli* K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asdA nucleic acid sequence does not replace the chromosomal asdA mutation since they have a deleted sequence in common. Additionally, the *E. coli* murA nucleic acid sequence was used in the plasmid instead of using the *Salmonella* murA nucleic acid sequence. In addition to being fully attenuated, this construction exhibits complete biological containment. This property enhances safety and minimizes the potential for exposure of individuals not intended for tumor treatment.

One of skill in the art will recognize that other nutrients besides arabinose may be used in the above mutations. By way of non-limiting example, xylose, mannose, and rhamnose regulatory systems may also be used.

In some embodiments of the invention, the recombinant bacterium may further comprise araBAD and araE mutations to preclude breakdown and leakage of internalized arabinose such that asdA and murA nucleic acid sequence expression continues for a cell division or two after oral immunization into an environment that is devoid of external arabinose. Additionally, a bacterium may comprise a mutation in a protein involved in GDP-fucose synthesis to preclude formation of colonic acid. Non-limiting examples of such a mutation include Δ(gmd-fcl)-26. A bacterium may also comprise a mutation like ΔrelA (e.g., ΔrelA1123) that uncouples cell wall-less death from dependence on protein synthesis.

Lysis of the bacterium will typically release lipid A, an endotoxin. So, a bacterium of the invention may comprise a mutation that reduces the toxicity of lipid A. Non-limiting examples may include a mutation that causes synthesis of the mono-phosphoryl lipid A. This form of lipid A is non-toxic, but still serves as an adjuvant agonist. For instance, in one embodiment, a recombinant bacterium may comprise a ΔpagP81::P$_{lpp}$ lpxE mutation. In particular embodiments, the lpxE sequence may be codon optimized for high-level expression in the recombinant bacterium.

A recombinant bacterium may also comprise a ΔrelA::TT araC P$_{BAD}$ lacI TT deletion-insertion mutation so that growth of the strain in the presence of arabinose causes synthesis of LacI to initially repress synthesis of protein antigens encoded by sequences under the control of P$_{trc}$. As a consequence of cell division in vivo during colonization of lymphoid tissues, LacI becomes diluted and expression of P$_{trc}$ controlled genes commences with synthesis of the protective antigen to stimulate induction of immune responses. In all cases the regulated delayed lysis phenotype is totally attenuating with no persistence of bacteria cells in vivo and no survival of bacteria cells if excreted. This regulated delayed lysis system has been described by Kong et al. (2008. Regulated programmed lysis of recombinant *Salmonella* in host tissues to release protective antigens and confer biological containment. Proc. Natl. Acad. Sci. USA 105: 9361-9366) and Curtiss and Kong (US Patent 2006/0140975), each of which is hereby incorporated by reference in its entirety. In certain embodiments, a recombinant bacterium of the invention may further comprise mutations to increase the expression of lacI. For instance, the SD sequence of lacI may be modified, the start codon may be modified, and/or structural codons may be modified to maximize transcription efficiency in the recombinant bacterium. In a specific embodiment, the SD sequence of lacI may be modified from AGGG to AGGA and/or the start codon may be modified from GTG to ATG.

(e) Expression of a Nucleic Acid Encoding an Antigen or Effector Protein

A recombinant bacterium of the invention may express or deliver one or more nucleic acids that encode one or more antigens or effector proteins. For instance, in one embodiment, a recombinant bacterium may be capable of the regulated expression of a nucleic acid sequence encoding an antigen or effector protein. In another embodiment, a recombinant bacterium may comprise a nucleic acid vaccine vector. Each of the above embodiments is described in more detail below. Other means of expressing or delivering one or more nucleic acids that encode one or more antigens are known in the art.

In one embodiment, the antigen is tumor specific antigen. In another embodiment, the antigen is an effector protein designed to illicit an innate immune response. For instance, in one embodiment, the effector protein is FasL and/or TRAIL. Additional examples of antigens may be found in sections i. and ii. below and in the Examples.

In some embodiments, antigens of the invention may be delivered via a type 2 or a type 3 secretion system.

i. Regulated Expression

The present invention encompasses a recombinant bacterium capable of the regulated expression of at least one nucleic acid sequence encoding an antigen or effector protein of interest. Generally speaking, such a bacterium comprises a chromosomally integrated nucleic acid sequence encoding a repressor and a vector. Each is discussed in more detail below.

A. Chromosomally Integrated Nucleic Acid Sequence Encoding a Repressor

A recombinant bacterium of the invention that is capable of the regulated expression of at least one nucleic acid sequence encoding an antigen or effector protein comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA nucleic acid sequence.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

1. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid sequence encoding an antigen or effector protein of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from E. coli if the recombinant bacterium is from the genus Salmonella. Alternatively, the repressor may be from a bacteriophage.

Suitable repressors are known in the art, and may include, for instance, LacI of E. coli, C2 encoded by bacteriophage P22, or C1 encoded by bacteriophage Λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

2. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system, which has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$). For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$.

Other enteric bacteria contain arabinose regulatory systems homologous to the araC-araBAD system from E. coli. For example, there is homology at the amino acid sequence level between the E. coli and the S. Typhimurium AraC proteins, and less homology at the DNA level. However, there is high specificity in the activity of the AraC proteins. For example, the E. coli AraC protein activates only E. coli $P_{BAD}$ (in the presence of arabinose) and not S. Typhimurium $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid sequence encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the P$_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the P$_{rhaRS}$ promoter and activates the production of RhaR and RhaS. RhaS together with L-rhamnose in turn binds to the P$_{rhaBAD}$ and the P$_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC P$_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the P$_{rhaBAD}$ promoter.

In still other embodiments, the promoter may be sensitive to the level of xylose in the environment. The xylR—P$_{xylA}$, system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-P$_{BAD}$ system described above, the xylR—P$_{xylAB}$ and/or xy/R—P$_{xylFGH}$ regulatory systems may be used in the present invention. In these embodiments, xylR P$_{xylAB}$ xylose interacting with the XylR protein activates transcription of nucleic acid sequences operably-linked to either of the two P$_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

3. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen or effector protein of interest, as detailed below. In an exemplary embodiment, the level of expression is optimized so that the repressor is synthesized while in the permissive environment (i.e. in vitro growth) at a level that substantially inhibits the expression of the nucleic acid sequence encoding an antigen or effector protein of interest, and is substantially not synthesized in a non-permissive environment, thereby allowing expression of the nucleic acid sequence encoding an antigen or effector protein of interest.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor. Modify can also mean optimization of codons to increase the stability of the mRNA to increase its half-life and thus the number of times it can be translated.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of the recombinant bacterium. In a further embodiment, the start codon of lacI may be altered, the SD sequence may be altered, and/or the codons of lacI may be optimized.

Methods of modifying the nucleic acid sequence encoding the repressor and/or the regulatable promoter are known in the art and detailed in the examples.

4. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

B. Vector

A recombinant bacterium of the invention that is capable of the regulated expression of at least one nucleic acid sequence encoding an antigen or effector protein comprises, in part, a vector. The vector comprises a nucleic acid sequence encoding at least one antigen or effector protein of interest operably linked to a promoter. The promoter is regulated by the chromosomally encoded repressor, such that the expression of the nucleic acid sequence encoding an antigen or effector protein of interest is repressed during in vitro growth of the bacterium, but the bacterium is capable of high level synthesis of the antigen or effector protein in an animal or human host. In certain embodiments, however, the promoter may also be regulated by a plasmid encoded repressor.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15 A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

1. Antigen or Effector Protein

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response decreases the size of a tumor, decreases metastases, and/or contributes to the lessening of any symptoms associated with a tumor. The use of the term "protective" in this invention does not necessarily require that the host is completely protected from the effects of the tumor. As used herein, "effector protein" refers to a biomolecule capable of inhibiting tumor cell growth. In some embodiments, an effector protein may induce programmed cell death (e.g. apoptosis or pyrotosis) in tumor cells, or may otherwise decrease the size of a tumor, decrease metastases, or contribute to the lessening of any symptoms associated with a tumor It is not necessary that the vector comprise the complete nucleic acid sequence of the antigen or effector protein. It is only necessary that the antigen sequence used be capable of eliciting an immune response, or the effector protein be capable of eliciting the desired effect. The antigen or effector protein may be one that was not found in that exact form in the parent organism. For example, a sequence coding for an antigen or effector protein comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen, effector protein, or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic or be effector proteins. In some embodiments, a vector of the invention may comprise a nucleic acid sequence encoding at least one antigen or effector protein, at least two antigens or effector proteins, at least three antigens or effector proteins, or more than three antigens or effector proteins. These antigens or effector proteins may be encoded by two or more open reading frames operably linked to be expressed coordinately as an operon, wherein each antigen or effector proteins is synthesized independently. Alternatively, the two or more antigens or effector proteins may be encoded by a single open reading frame such that the antigens or effector proteins are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tenus toxin fragment C, CT-B, LT-B and hepatitis virus B core are particularly useful for these purposes, although other epitope presentation systems such as hepatitis B virus and woodchuck hepatitis virus cores are well known in the art.

In further embodiments, a nucleic acid sequence encoding an antigen or effector protein of the invention may comprise a secretion signal. In other embodiments, an antigen or effector protein of the invention may be toxic to the recombinant bacterium.

In one embodiment, an effector protein may be SopE2. In some embodiments, the native promoter may be replaced with $P_{trc}$ to enable the regulated delayed synthesis of SopE2. In certain embodiments, the start codon of sopE2 may be modified to alter its expression level. For instance, the start codon may be changed from GTG to ATG.

2. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen or effector protein of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen or effector protein, such that expression of the nucleic acid sequence encoding an antigen or effector protein is repressed when the repressor is synthesized (i.e. during in vitro growth of the bacterium), but expression of the nucleic acid sequence encoding an antigen or effector protein is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding an antigen or effector protein after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen or expression protein after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

3. Expression of the Nucleic Acid Sequence Encoding an Antigen or Effector Protein As detailed above, generally speaking the expression of the nucleic acid sequence encoding the antigen or effector protein should be repressed when the repressor is synthesized. For instance, if the repressor is synthesized during in vitro growth of the bacterium, expression of the nucleic acid sequence encoding the antigen or effector protein should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen or effector protein should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen or effector protein should be high. As used herein, "high level" expression refers to expression that is strong enough to elicit an immune response to the antigen or to see the effects of the effector protein on the tumor cell. Consequently, the copy number correlating with high level expression can and will vary depending on the antigen or effector protein and the type of immune response desired. Methods of determining whether an antigen elicits an immune response such as by measuring antibody levels or antigen-dependant T cell populations or antigen-dependant cytokine levels are known in the art, and methods of measuring levels of expression of antigen or effector protein encoding sequences by measuring levels of mRNA transcribed or by quantitating the level of antigen or effector protein synthesis are also known in the art.

ii. Nucleic Acid Vaccine Vector

A recombinant bacterium of the invention may encompass a nucleic acid vaccine vector. Such a vector is typically designed to be transcribed in the nucleus of the host cell to produce mRNA encoding one or more antigens or effector proteins of interest. To increase performance, a nucleic acid vaccine vector should be targeted to the nucleus of a host cell, and should be resistant to nuclease attack.

In one embodiment of the invention, a nucleic acid vaccine vector may be targeted to the nucleus using a DNA nuclear targeting sequence. Such a sequence allows transcription factors of the host cell to bind to the vector in the cytoplasm and escort it to the nucleus via the nuclear localization signal-mediated machinery. DNA nuclear targeting sequences are known in the art. For instance, the SV40 enhancer may be used. In particular, a single copy of a 72-bp element of the SV40 enhancer may be used, or a variation thereof. The SV40 enhancer may be used in combination with the CMV immediate-early gene enhancer/promoter.

Additionally, DNA binding sites for eukaryotic transcription factors may be included in the vaccine vector. These sites allow transcription factors such as NF-κB and AP-2 to bind to the vector, allowing the nuclear location signal to mediate import of the vector to the nucleus.

A nucleic acid vaccine vector of the invention may also be resistant to eukaryotic nuclease attack. In particular, the polyadenalytion signal may be modified to increase resistance to nuclease attack. Suitable polyadenylation signals that are resistant to nuclease attack are known in the art. For instance, the SV40 late poly A signal may be used. Alternatively, other poly A adenylation signal sequences could be derived from other DNA viruses known to be successful in infecting avian and/or mammalian species.

A bacterium comprising a nucleic acid vaccine vector may also comprise a mutation that eliminates the periplasmic endonuclease I enzyme, such as a ΔendA mutation, e.g. ΔendA2311. This type of mutation is designed to increase vector survival upon the vector's release into the host cell.

In one embodiment, a nucleic acid vaccine vector may comprise a promoter that is over-expressed in a tumor. For instance, the hexokinase type II promoter may be used. In an exemplary embodiment, the hexokinase type II promoter may be operably linked to a nucleic acid encoding Fas ligand.

(f) Attenuation

In each of the above embodiments, a recombinant bacterium of the invention may also be attenuated. "Attenuated"

refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the tumor is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of tumor tissues before the recombinant bacterium is regulated to display the attenuated phenotype.

In one embodiment, a recombinant bacterium may be attenuated by regulating LPS O-antigen. In other embodiments, attenuation may be accomplished by altering (e.g., deleting) native nucleic acid sequences found in the wild type bacterium. For instance, if the bacterium is Salmonella, non-limiting examples of nucleic acid sequences which may be used for attenuation include: a pab nucleic acid sequence, a pur nucleic acid sequence, an aro nucleic acid sequence, asdA, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asdA. Other modifications that may be employed include modifications to a bacterium's ability to synthesize D-alanine or to synthesize D-glutamic acid (e.g., Δmurl mutations), which are both unique constituents of the peptidoglycan layer of the bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

Other means of attenuation are known in the art.

i. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be necessary to synthesize a component of the cell wall of the bacterium, or may itself be a necessary component of the cell wall such as the protein encoded by murA.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid sequence encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta$araBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as $\Delta$araBAD23, which prevents use of arabinose retained in the cell cytoplasm at the time of oral immunization, and/or $\Delta$araE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in section (d).

In some embodiments, more than one modification may be performed to optimize the attenuation of the bacterium. For instance, at least one, two, three, four, five, six, seven, eight or nine modifications may be performed to optimize the attenuation of the bacterium. In various exemplary embodiments of the invention, the SD sequences and/or the start codons for the fur and/or the phoPQ virulence nucleic acid sequences may be altered so that the production levels of these nucleic acid products are optimal for regulated attenuation.

(g) Other Mutations

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC$_{BAD}$ P may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated or constructed that synthesize a Crp protein that is not dependent on cAMP to regulate transcription from $P_{BAD}$. Two such alterations in the crp gene have been made with amino acid substitution mutations T127I, Q170K and L195R to result in the crp-70 gene modification and with amino acid substitutions I112L, T127I and A144T to result in the crp-72 gene modification. Both constructions have been made with araC $P_{BAD}$ to yield the $\Delta P_{crp70}$::TT araC $P_{BAD}$ crp-70 and $\Delta P_{crp72}$::TT araC $P_{BAD}$ crp-72 deletion-insertion mutations. In both cases, synthesis of the Crp protein induced by arabinose is insensitive to the addition of glucose. This strategy may also be used in other systems responsive to Crp, such as the systems responsive to rhamnose and xylose described above.

(h) Exemplary Bacterium

In an exemplary embodiment, a bacterium may comprise one or more mutations to increase invasiveness (section (a) above), one or more mutations that enhance stimulation of host innate immune responses (section (b) above), one or more mutations to increase bacterium-induced host programmed cell death (section (c) above), one or more mutations to induce lysis of the bacterium (section (d) above), one or more vectors to express a nucleic acid encoding an antigen or effector protein (section (e) above), one or more mutations to attenuate the bacterium (section (f) above), and one or more mutations to enhance the performance of the bacterium as a vaccine (section (g) above).

In one embodiment, a bacterium of the invention may comprise the following mutations: $\Delta$asdA27::TT araC $P_{BAD}$ c2 $\Delta P_{murA25}$::TT araC $P_{BAD}$ murA $\Delta$(wza-wcaM)-8 $\Delta$relA198::araC $P_{BAD}$ lacI TT $\Delta$(araC $P_{BAD}$)-18::P22 $P_R$ araBAD $\Delta$pagP81::$P_{lpp}$ IpxE $\Delta$endA2311 $\Delta P_{hilA}$::$P_{trc\ \Delta lacO888}$ hilA. In another embodiment, a bacterium of the invention may comprise the following mutations: $\Delta P_{murA25}$::TT araC $P_{BAD}$ murA $\Delta$(wza-wcaM)-8 $\Delta$relA198::araC $P_{BAD}$ lacI TT $\Delta$(araC $P_{BAD}$)-18::P22 $P_R$ araBAD $\Delta$pagP81::$P_{lpp}$ IpxE $\Delta$endA2311 $\Delta P_{tar}$::$P_{trc\ \Delta lacO888}$ tar $\Delta P_{tsr}$::$P_{trc\ \Delta lacO888}$ tsr $\Delta$trg or $\Delta P_{trg}$::rhaRS-$P_{rhaB}$ trg $\Delta P_{hilA}$::$P_{trc\ \Delta lacO888}$ hilA $\Delta$purA. In yet another embodiment, a bacterium of the invention may comprise the following mutations: $\Delta$asdA27::TT araC $P_{BAD}$ c2 $\Delta P_{murA25}$::TT araC $P_{BAD}$ murA $\Delta$(wza-wcaM)-8 $\Delta$relA198::araC $P_{BAD}$ lacI TT $\Delta$(araC $P_{BAD}$)-18::P22 $P_R$ araBAD $\Delta$pagP81::$P_{lpp}$ IpxE $\Delta$endA2311 $\Delta P_{tar}$::$P_{trc\ \Delta lacO888}$ tar $\Delta P_{tsr}$::$P_{trc\ \Delta lacO888}$ tsr $\Delta$trg or $\Delta P_{trg}$::rhaRS-$P_{rhab}$ trg $\Delta P_{hilA}$::$P_{trc\ \Delta lacO888}$ hilA $\Delta$purA_$\Delta P_{sopE2}$::$P_{trc}$ sopE2. In still another embodiment, a bacterium of the invention may comprise the following mutations: $\Delta$asdA27::

TT araC $P_{BAD}$ c2 $\Delta P_{murA25}$::TT araC $P_{BAD}$ murA $\Delta$(wza-wcaM)-8 $\Delta$relA 198::araC $P_{BAD}$ lacl TT $\Delta$(araC $P_{BAD}$)-18::P22 $P_R$ araBAD $\Delta$pagP81::$P_{lpp}$ IpxE $\Delta$endA2311 $\Delta P_{tar}$::$P_{trc\ \Delta lacO888}$ tar $\Delta P_{tsr}$::$P_{trc\ \Delta lacO888}$ tsr $\Delta$trg or $\Delta P_{trg}$::rhaRS-$P_{rhaB}$ trg $\Delta P_{hilA}$::$P_{trc\ \Delta lacO888}$ hilA $\Delta$purA $\Delta P_{sopE2}$::$P_{trc}$ sopE2 $\Delta P_{tlpA}$::$P_{ansB}$ tlpA.

In a certain embodiment, the bacterium comprises the following mutations: $\Delta$asdA27::TT araC $P_{BAD}$ c2, $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311.

In another embodiment, the bacterium comprises the following mutations: $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$::$P_{trc\ \Delta lacO888}$ tar.

In still another embodiment, the bacterium comprises the following mutations: $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$::$P_{trc\ \Delta lacO888}$ tar, $\Delta P_{tsr}$:: $P_{trc\ \Delta lacO888}$ tsr.

In yet another embodiment, the bacterium comprises the following mutations: $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$::$P_{trc\ \Delta lacO888}$ tar, $\Delta P_{tsr}$:: $P_{trc\ \Delta lacO888}$ tsr, $\Delta$trg, or $\Delta P_{trg}$::rhaRS-$P_{rhaB}$ trg.

In a further embodiment, the bacterium comprises the following mutations: $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$::$P_{trc\ \Delta lacO888}$ tar, $\Delta P_{tsr}$:: $P_{trc\ \Delta lacO888}$ tsr, $\Delta$trg, or $\Delta P_{trg}$::rhaRS-$P_{rhaB}$ trg, $\Delta P_{hilA}$::$P_{trc\ \Delta lacO888}$ hilA.

In still a further embodiment, the bacterium comprises the following mutations: $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$::$P_{trc\ \Delta lacO888}$ tar, $\Delta P_{tsr}$:: $P_{trc\ \Delta lacO888}$ tsr, $\Delta$trg, or $\Delta P_{trg}$::rhaRS-$P_{rhaB}$ trg, $\Delta P_{hilA}$::$P_{trc\ \Delta lacO888}$ hilA, $\Delta$purA.

In an alternative embodiment, the bacterium comprises the following mutations: $\Delta$asdA27::TT araC $P_{BAD}$ c2, $\Delta P_{murA25}$::TT araC $P_{BAD}$ murA, $\Delta$(wza-wcaM)-8, $\Delta$relA198::araC $P_{BAD}$ lacl TT, $\Delta$(araC $P_{BAD}$)-18::P22 $P_R$ araBAD, $\Delta$pagP81::$P_{lpp}$ IpxE, $\Delta$endA2311, $\Delta P_{tar}$:: $P_{trc\ \Delta lacO888}$ tar, $\Delta P_{tsr}$::$P_{trc\ \Delta lacO888}$ tsr, $\Delta$trg, or $\Delta P_{trg}$::rhaRS-$P_{rhaB}$ trg, $\Delta P_{hilA}$::$P_{trc\ \Delta lacO888}$ hilA, $\Delta$purA, $\Delta P_{sopE2}$::$P_{trc}$ sopE2.

In yet another alternative, the bacterium comprises the following mutations: $\Delta$asdA27::TT araC $P_{BAD}$ c2, $\Delta P_{murA25}$::TT araC $P_{BAD}$ murA, $\Delta$(wza-wcaM)-8, $\Delta$relA 198::araC $P_{BAD}$ lacl TT, $\Delta$(araC $P_{BAD}$)-18::P22 $P_R$ araBAD, $\Delta$pagP81::$P_{lpp}$ IpxE. $\Delta$endA2311, $\Delta P_{tar}$::$P_{trc\ \Delta lacO888}$ tar, $\Delta P_{tsr}$::$P_{trc\ \Delta lacO888}$ tsr, $\Delta$trg, or $\Delta P_{trg}$::rhaRS-$P_{rhaB}$ trg, $\Delta P_{hilA}$::$P_{trc\ \Delta lacO888}$ hilA, $\Delta$purA, $\Delta P_{sopE2}$::$P_{trc}$ sopE2, $\Delta P_{tlpA}$::$P_{ansB}$ tlpA.

II. Pharmaceutical Compositions and Administration

Pharmaceutical compositions of the present invention may be administered to any host susceptible to tumors and the recombinant bacterium. Such hosts may include all vertebrates, for example, mammals, including domestic animals, agricultural animals, laboratory animals, and humans, and various species of birds, including domestic birds and birds of agricultural importance. Preferably, the host is a warm-blooded animal.

In exemplary embodiments, the recombinant bacterium is alive when administered to a host in a pharmaceutical composition of the invention. Suitable pharmaceutical composition formulations and methods of administration are detailed below.

(a) Pharmaceutical Composition

A pharmaceutical composition comprising a recombinant bacterium of the invention may optionally comprise one or more possible additives, such as carriers, preservatives, stabilizers, and other substances.

In another embodiment, the composition may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

Care should be taken when using additives so that the live recombinant bacterium is not killed, or have its ability to effectively colonize tumor tissues compromised by the use of additives. Stabilizers, such as lactose or monosodium glutamate (MSG), may be added to stabilize the pharmaceutical formulation against a variety of conditions, such as temperature variations or a freeze-drying process.

The dosages of a pharmaceutical composition of the invention can and will vary depending on the recombinant bacterium, the regulated antigen or effector protein, and the intended host, as will be appreciated by one of skill in the art. Generally speaking, the dosage need only be sufficient to elicit an anti-tumor response in a majority of hosts. Routine experimentation may readily establish the required dosage. Typical initial dosages of a pharmaceutical composition for oral administration could be about $1\times10^7$ to $1\times10^{10}$ CFU depending upon the age of the host to be immunized. Administering multiple dosages may also be used as needed to provide the desired level of anti-tumor activity. In some embodiments, parental administration is preferred (e.g. for treatment of internal solid tumors). In such embodiments, doses may range from about $1\times10^5$ to $1\times10^8$ CFU.

(b) Methods of Administration

A pharmaceutical composition may be administered orally intravenously, intramuscularly, or by subcutaneous injection. In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

III. Methods of Use

A further aspect of the invention encompasses methods of using a recombinant bacterium of the invention. For instance, in one embodiment the invention provides a method for inhibiting tumor growth. The method generally comprises administering a recombinant bacterium of the invention to a subject. In another embodiment, the invention provides a method for treating cancer. The method generally comprises administering a recombinant bacterium of the invention to a subject.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Introduction for Examples 1-8

Colorectal cancer is the second leading cause of cancer-related deaths in the United States (after lung cancer). According to the American Cancer Society, almost 150,000 new cases of colorectal cancer were diagnosed and approximately 50,000 people died from the disease last year. Multidrug resistance and the presence of undetectable micrometastases, which are caused by at least two mechanisms: i.e. limited drug penetration and poor cell susceptibility (59, 80), significantly reduce the effectiveness of most cancer therapeutics, mainly radiotherapy and chemotherapy. Uneven perfusion in tumors creates populations of cells that are physically distant from therapeutics in the bloodstream and are quiescent due to nutrient deficiencies (105). The other substantial limitation of conventional cancer chemotherapy and radiotherapy is the toxicity of these agents to normal tissue (131). This has prompted the development of many new approaches for the treatment of cancer including the delivery of anti-cancer genes to the tumor site in various gene therapy protocols (85, 119). However, current gene therapy protocols require local administration of vectors, which limits their usefulness. Also the nonselectivity of the available gene delivery systems renders cancer gene therapy strategies potentially toxic to normal cell populations. Although there have been recent advances in adjuvant therapy, there are no major breakthroughs in the treatment of colorectal cancers.

Motile facultative anaerobes have the potential to actively penetrate into tumor tissue and overcome diffusion limitation, where they could attack quiescent cancer cells that are impervious to standard chemo- and radiotherapies (49, 67, 78, 113). The preferential accumulation of bacteria in certain experimental tumors was initially reported in the 1950s when spores of *Clostridium tetani* were shown to germinate exclusively in the tumor after intravenous administration into tumor-bearing mice (96). It was assumed that the obligate anaerobic bacteria were replicating in the necrotic/hypoxic centers of these tumors, leaving the well oxygenated normal tissues unaffected. In an initial clinical trial in humans using spores of *Clostridia* incapable of producing toxins, most patients showed no objective regression (23). Thus, further studies were abandoned due to the lack of clinical efficiency. More recently, investigators have attempted to use the tumor-targeting properties of *Clostridia* for the selective delivery of pro-drug converting enzymes (106). Once germinated within the tumor, these *Clostridia* destroy adjacent tumor cells through the secretion of degradative enzymes, at the same time the host reacts to the bacterial infection by producing cytokines that lead to the influx of inflammatory cells. On the one hand, the inflammatory reaction restricts bacterial growth, and on the other hand, it may also contribute to the destruction of tumor cells (2). Anaerobic *Bifidobacteria* have also been investigated and shown to colonize tumors. In contrast to *Clostridia*, *Bifidobacteria* are non-pathogenic bacteria found naturally in the digestive tract of humans and other mammals and therefore may represent a safer alternative compared to *Clostridia* (137). Strains of these bacteria, which were modified to produce cytosine deaminase and the antiangiogenic protein endostatin (103), resulted in inhibition of angiogenesis and retardation of growth of the tumor after systemic administration. In addition, oral administration of *Bifidobacterium longum* carrying the endostatin gene was efficient in a liver tumor model (52). However, the utility of anaerobes as anti-cancer agents is limited by the absolute requirement for anoxic conditions, which restrict their activity to large tumors.

However, these restrictions do not apply to facultative anaerobes such as the gram-negative bacterium *S. Typhimurium*. These bacteria have the potential to colonize not only the anaerobic necrotic parts of the tumor but also oxygenated proliferative and quiescent tumor regions as well as metastatic lesions (49). This promoted an extensive research on using attenuated strains of *S. Typhimurium* for tumor therapy. The capacity of *Salmonella* to preferentially target and replicate in tumor tissue has been used in tumor therapy. This was first demonstrated in 1997, in which injected auxotrophic *Salmonella* were shown to specifically accumulate in the malignant tissue of tumor-bearing mice (113). The ratio of bacteria in the tumor to bacteria in normal tissues ranged between 250:1 and 9000:1 and this specific accumulation was accompanied by retarded tumor growth. Other studies have confirmed these findings and further shown that attenuated *Salmonella* have bacteriolytic activity (120). Although the precise molecular mechanisms for this antitumor effect remain elusive, it has been reported that infected tumor cells present antigens of bacterial origin and become targets for *Salmonella*-specific T cells (7). It is proposed that massive recruitment of both innate and adaptive effector cells at the site of infection and *Salmonella*-induced cross-presentation of tumor antigens contribute to the antitumor activity (7). Furthermore, *Salmonella* strains have been constructed in order to deliver therapeutic molecules such as the herpes simplex thymidine kinase protein (113), endostatin (87) and thrombospondin-1 (88). A safety barrier for the utilization bacteria as systemically administered anti-cancer agents in humans is that they often massively stimulate TNF-α induction, which might lead to a cytokine cascade responsible for septic shock (28). This effect is mediated by lipid A of gram-negative bacteria, which is a component of the bacterial outer membrane. By disrupting the msbB gene, which encodes a myristil transferase involved in the synthesis of this lipid moiety, TNF-α induction could be reduced without losing the tumor-targeting and tumorinhibiting properties (91). A safe attenuated strain of *S. Typhimurium* VNP20009, was generated, in which the purI gene and msbB gene were deleted and remained susceptible to antibiotics (28). In initial clinical trials, this strain showed tumor colonization but no tumor regression was observed (133), even when a pro-drug converting enzyme was expressed (110). Both bacterial and tumor-related factors have been implicated for the preferential accumulation of *Salmonella* in tumors. It has been shown that chemoattractive compounds produced by quiescent tumor cells contribute to the preferential accumulation (78). However, the administration of *Salmonella* to tumor-bearing animals also caused bacteria to colonize normal tissues, albeit transiently and to a lesser extent. In case of constitutive expression of therapeutic genes, this might cause adverse side effects. The increased specificity of the growth in tumor tissue could be recently achieved by creating Leu/Arg-dependent auxotrophic *Salmonella* mutants (146, 147). These mutants were cleared from normal tissue even in immunodeficient mice, whereas the tumors were still colonized. Also, it would be desirable to use regulated promoters that can be turned on either specifically in tumors or at certain time points when the bacteria have been cleared from normal tissues. In addition, several studies have found that *S. Typhimurium* purA auxotrophs are fully attenuated and undetectable 21 days after inoculation in healthy tissue. This is because there is an insufficient supply of unphosphorylated purines available in healthy tissues to enable growth. Therefore, the means to improve the bacterial carrier for efficient tumor therapy may be investigated.

Immune cells play an important role in the control of spontaneous tumors such as melanoma that express endogenous tumor antigens (126). Innate immune cells respond to "danger" signals, which can be provided by growing tumors due to cell transformation and disruption of the surrounding microenvironment. Ideally, these signals induce inflammation, activation of innate effector cells with anti-tumor activity and stimulation of dendritic cells (DC) to present tumor-derived antigens and to trigger an adaptive immune response (15). Tumors often exhibit strategies to escape this immunosurveillance, such as exclusion of immune cells from tumor sites, impairing antigen presentation by DCs and poor immunogenicity due to reduced expression of MHC molecules and co-stimulatory proteins (98). The strategies have been developed to manipulate the innate immune responses by administration of adjuvants, cytokines or ligands for co-stimulatory proteins directly triggering innate immune cells (15). As the global activation of the innate immune system often leads to toxicity, it is desirable to combine this approach with specific targeting of the tumor, e.g. providing effector molecules specifically at the tumor site. In this respect, the use of bacteria as vaccine vectors and delivery systems for therapeutic molecules represents a very promising alternative. More than 100 years ago, William B. Coley observed that, when patients with sarcomas developed acute streptococcal infections, their tumors regressed due to the stimulation of the innate immune system (29). The background of the attenuated bacterial carrier strain and the type of mutation selected to achieve attenuation critically affect the extent and quality of elicited immune responses (42, 136).

The apoptosis-inducing Fas ligand (FasL) is a membrane protein that belongs to the tumor necrosis factor family. After binding to its receptor (Fas), it initiates an apoptotic signal in the Fas-sensitive cells (132). This mechanism is of particular importance for a variety of physiological and pathological conditions, including the killing of transformed target cells by cytotoxic T lymphocytes and natural killer cells (116). However, it has been shown that systemic administration of recombinant FasL induced lethal liver injury (115). TNF-related apoptosis inducing ligand (TRAIL) is a protein that has been a focus of cancer research since 1995, because of its ability to induce apoptosis in cancer cells by stimulating death receptors on the cell surface, while leaving normal cells relatively unaffected. It is believed that TRAIL is part of the body's natural defense system against cancer. The Examples below describe the use of attenuated *S. Typhimurium* with multiple improved features to deliver tumor-specific synthesized FasL and/or TRAIL as cytotoxic and immunostimulatory therapeutic proteins. Although initial studies using *S. Typhimurium* constructs provide preclinical data from experiments with mice, the ultimate use of these delivery systems in humans might more logically rely on human host-adapted *S. Typhi* and *S. Paratyphi* A vaccine vector systems.

Attenuation of *Salmonella* vectors should decrease, if not eliminate, induction of undesirable disease symptoms while retaining immunogenicity. Such *Salmonella* vectors should be sufficiently invasive and persistent and minimize unnecessary tissue damage. However, it is difficult to achieve a balance between these desirable safety features and immunogenicity. Many means to attenuate *Salmonella* make them less able to tolerate stresses encountered after administration. To address these problems, strains were designed that display features of wild-type virulent strains of *Salmonella* at the time of inoculation to enable strains for effective colonization and then exhibit a regulated delayed attenuation in vivo to preclude inducing disease symptoms (30, 34, 82). Using live attenuated *Salmonella* as carriers of homologous and heterologous antigens, the inventors and others have developed a variety of attenuating mutations and antibiotic resistance-free balanced-lethal plasmid stabilization systems (22, 56, 57, 109). However, biological containment systems are recommended to address potential risks posed by the unintentional release of these genetically modified organisms into the environment as a subject of considerable concern (37, 84). Such release can lead to unintentional infections and the possible transfer of cloned genes that might represent virulence attributes in some cases (31, 100). An approach has been to develop a biological containment system that will allow *Salmonella* strains enough time to colonize the host tissues, a requirement for delivery of selected proteins and DNA vaccine vectors but eventually leads to *Salmonella* cell death by programmed cell lysis, thus preventing *Salmonella* strain persistence in vivo and spread into the environment (82). Also, release of the synthesized proteins or DNA vaccine vectors from the RAS strains with programmed lysis phenotype would be much more efficient than a non-lysis delivery system.

To significantly improve on these accomplishments, innovative improvements in these processes may be investigated and perfected. These efforts are described in the Examples below.

Example 1

Available Improved Means to Genetically Alter *S. Typhimurium* To Display Regulated Delayed or Constitutive Synthesis of Selected Proteins Aerobically and Anaerobically and to Diminish Toxicity of Lipid a to Reduce The Possibility of Septic Shock Overexpression of foreign protein by recombinant attenuated *S. Typhimurium* (RAS) strains reduces colonizing ability and thus immunogenicity. It was for this reason that Chatfield et al. (25) proposed the use of the nirB promoter that is more active anaerobically than aerobically in accord with a more likely in vivo anaerobic environment. The promoter, $P_{trc}$, that had been used by the inevntors (55, 74, 125) is constitutively active under most environments but is more transcriptionally active in both anaerobic and aerobic conditions than the nirB promoter (25). Therefore, ΔrelA198::araC $P_{BAD}$ lacI TT (90) was generated, so that Salmonella strains growing in the presence of arabinose should synthesize the LacI repressor to inhibit transcription from $P_{trc}$ in Salmonella until after administration when the Salmonella strain is already colonizing internal targeted tissues. This technology was incrementally improved to ultimately increase expression of the lacI gene 40-fold by changing (i) the SD sequence from AGGG to AGGA, (ii) the start codon from GTG to ATG, and (iii) structural codons to maximize transcription efficiency in Salmonella. In addition, an alternative $P_{trc}$ promoter that lacks the operator lacO sequence was created to enable constitutive synthesis of selected protein, if necessary, even when the lacI gene in the host strain is expressed.

The regulated delayed lysis phenotype results in the release of the lipid A endotoxin which is inflammatory via interaction with TLR4 and MD2 (114), and also induces TNF-α mediated septic shock (79). To preclude this, the $\Delta pagP81::P_{lpp}$ IpxE deletion-insertion mutation was generated and fully evaluated. This construction contains the IpxE gene from Francisella tularensis that has been codon-optimized for high-level expression in Salmonella, and the resulting strain produces the mono-phosphoryl lipid A, which is totally non-toxic and yet is a safe adjuvant for recruitment of innate immunity (5). Therefore, a strain with the optimal lipid A form to enhance innate immunity and reduce septic shock may now be constructed.

Example 2

Figure 2:
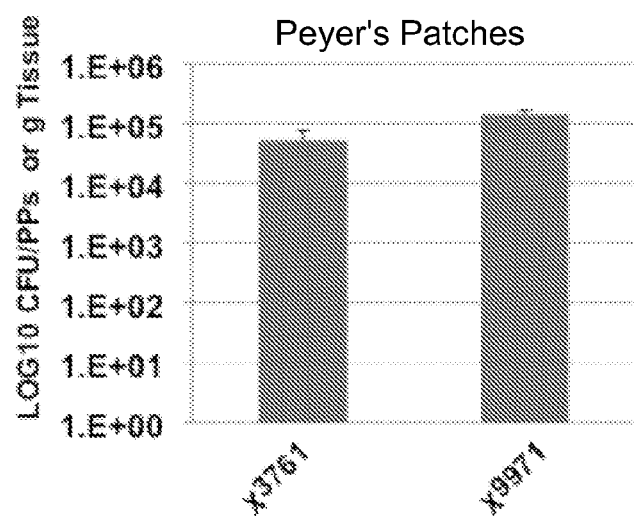
FIG. 2. Colonization of mice with *S. Typhimurium* strains at day 6 post-inoculation. (A) Peyer's patches, (B) spleen, (C) liver.
Figure 2:
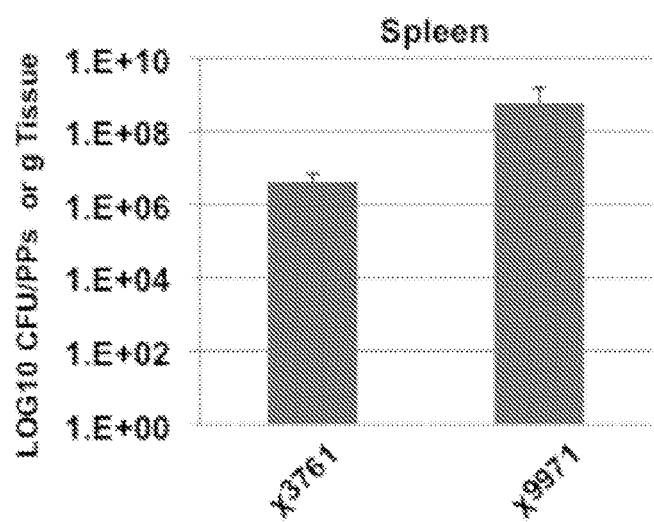
Figure 2:
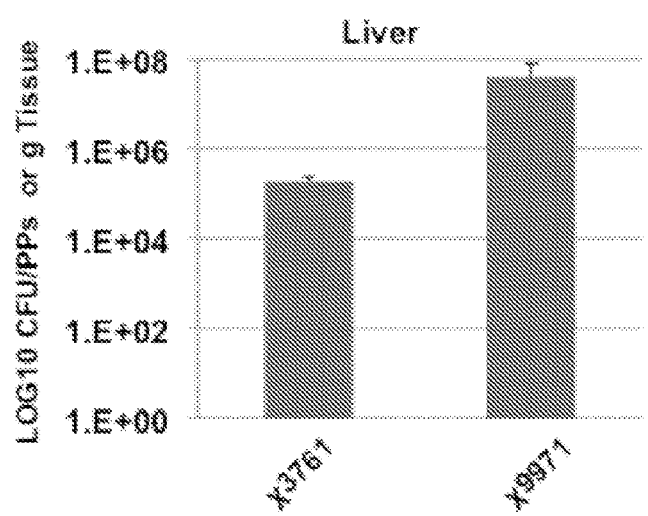

Construction of Hyper-Invasive Strains to Enhance Delivery of Selected Protein and DNA Vaccine Vector One of the major mechanisms of S. Typhimurium invasion of animal hosts is to enter and traverse the epithelial monolayer lining the intestine through microfold (M) cells (50, 69, 71, 128). The expression of genes required for invasion of M cells is tightly regulated by a variety of regulatory factors that are activated by specific environmental conditions. The hilA (hyper-invasion locus) regulator encodes an OmpR/ToxR family transcriptional regulator that activates the expression of invasion genes in response to both environmental and genetic regulatory factors (9, 10). The regulation of hilA expression is a key point for controlling expression of the invasive phenotype (8, 43, 92). To improve M cell mediated Salmonella invasion for efficient oral administration, the hilA promoter was replaced with an artificial $P_{trc\Delta lacO888}$ promoter that lacks the operator lacO sequence to enable constitutive synthesis of HilA even when the lacI gene in the host strain is expressed. The S. Typhimurium strain 9971 ($\Delta P_{hilA}::P_{trc\Delta lacO888}$ hilA) was able to invade and replicate in human intestinal Int-407 cells (MOI 50:1) (FIG. 1) and colonize mouse tissues in significantly greater numbers than the wild-type strain (FIG. 2).

Example 3

Construction of S. Typhimurium Vaccine Strains with Regulated Expression of Genes for the Synthesis of Essential Components of the Peptidoglycan Enabling Regulated Delayed Lysis after Colonization to Release Selected Proteins and DNA Vaccine Vectors In Vivo and Confer Attenuation And Complete Biological Containment To eliminate use of plasmid vectors with non-permitted drug resistance genes and to stabilize plasmid vectors in recombinant attenuated Salmonella strains in vivo, a balanced-lethal Salmonella host-vector system with deletion of the asdA gene to impose an obligate requirement for diaminopimelic acid (DAP) was developed (13), and a plasmid vector with the wild-type asdA gene (32, 55). The murA gene encodes the first enzyme in muramic acid synthesis (18). DAP and muramic acid are essential unique constituents of peptidoglycan. The asdA and murA systems were combined, providing redundant mechanisms to ensure cell death. A regulated delayed lysis system was devised for antigen delivery after colonization of host lymphoid tissues that relies on using a more tightly regulated araC $P_{BAD}$ activator-promoter (82) than the original sequence from E. coli B/r (60) for the arabinose-dependant synthesis of the Asd and MurA enzymes. This system is composed of two parts. The first component is the S. Typhimurium strain 8937 ($\Delta asdA19::TT$ araC $P_{BAD}$ c2 TT $\Delta P_{murA7}::TT$ araC $P_{BAD}$ murA $\Delta(gmd-fcl)$-26 $\Delta relA1123$ $\Delta endA2311$) with deletion of the asdA gene, arabinose-regulated expression of murA and additional mutations to enhance complete lysis and antigen delivery. Unlike strains with asdA deletions, which can be grown by addition of DAP to the growth medium, strains with murA deletions are lethal due to an inability to supply the phosphorylated substrate for the MurA enzyme. Therefore, a conditional-lethal arabinose-dependant murA mutation was created by replacing the chromosomal murA promoter with the araC $P_{BAD}$ activator-promoter. Although arabinose is present in plant foods, most is in a complex form unavailable to support growth of strains with $\Delta P_{murA7}$:: TT araC $P_{BAD}$ murA deletion-insertion mutations. Thus a strain with the $\Delta P_{murA7}::TT$ araC $P_{BAD}$ murA mutation undergoes about two cell divisions and then commences to lyse in media without arabinose (82). The $\Delta(gmd-fcl)$-26 mutation deletes genes encoding enzymes for GDP-fucose synthesis, thereby precluding the formation of colanic acid, a polysaccharide made in response to stress associated with cell wall damage (141). This mutation was included because it was observed that under some conditions, asdA mutants can survive if they produce copious amounts of colonic acid (33). Therefore, by deleting the genes required for colanic acid synthesis, this possibility was circumvented. The $\Delta relA1123$ mutation uncouples cell wall-less death from dependence on protein synthesis to further ensure that the bacteria do not survive in vivo or after excretion and to allow for maximum antigen production in the face of amino acid starvation resulting from a lack of aspartate semi-aldehyde synthesis due to the asdA mutation (38, 75). The second component is plasmid pYA3681, which encodes arabinose-regulated murA and asdA expression and C2-regulated synthesis of anti-sense asdA and murA mRNA transcribed from the P22 $P_R$ promoter with opposite polarity at the 3' end of the asdA gene. The mRNA translation efficiency was reduced for both the murA and asdA genes by changing their start codons from ATG to GTG. An arabinose-regulated c2 gene is present in the chromosome due to the $\Delta asdA19::TT$ araC $P_{BAD}$ c2 TT deletion-insertion. The cloning of a sequence encoding a protective antigen is under $P_{trc}$ control. Transcription terminators (TT) flank all of the domains for controlling lysis, replication and expression so that expression of a function in one domain does not affect the activities of another domain. As a safety feature, the plasmid asdA and murA gene sequences cannot replace the chromosomal asdA and murA mutations. χ8937 (pYA3681) exhibits arabinose-dependent growth. Upon invasion of host tissues, an arabinose-free environment, transcription of asdA, murA and c2 ceases and concentrations of their gene products decrease due to cell division. The drop in C2 concentration results in activation of $P_R$, driving synthesis of anti-sense mRNA to block translation of any residual asdA and murA mRNA (82). This host-vector grows in LB broth with 0.2% L-arabinose as well as the wild-type strain χ3761, but is unable to grow in or on media devoid of arabinose since it undergoes cell wall-less death by lysis (82). Vaccine strains with this regulated lysis system are totally avirulent at oral doses in excess of $10^9$ CFU to BALB/c mice and, by release of a bolus of protective antigen upon lysis, induce very good immune responses (82). These *Salmonella* host-vector systems are ideal for delivery of selected proteins that are difficult to secrete due to structural attributes. In addition, they provide complete biological containment with no persistence in vivo and no survival if excreted (82).

The regulated lysis phenotype commences as the products of arabinose-regulated genes are diluted at each cell division. Onset of programmed lysis can be delayed about one cell division by including the Δ(araC $P_{BAD}$)-18::P22 $P_R$ araBAD mutation, which initially prevents breakdown of accumulated arabinose at the time of inoculation but later allows breakdown of residual arabinose to reduce likelihood of expressing any araC $P_{BAD}$ regulated genes. This mutation also prevents acid production by metabolism of arabinose that must be included in the growth medium for *Salmonella* strains exhibiting the regulated lysis phenotype. This is important to maximize generation of an invasive phenotype during growth of *Salmonella* strains. It should be noted that the −10, SD and C2 repressor binding sites have been altered so that as C2 decreases the araBAD genes are expressed at a higher level than in wild-type strains. We have also constructed the much-improved ΔasdA27::TT araC $P_{BAD}$ c2 and Δ$P_{murA25}$::TT araC $P_{BAD}$ murA deletion-insertion mutations that share the tightly-regulated araC $P_{BAD}$ cassette and a better spacing of the regulatory sequences was included in Δ$P_{murA}$ mutation.

Example 4

Figure 3:
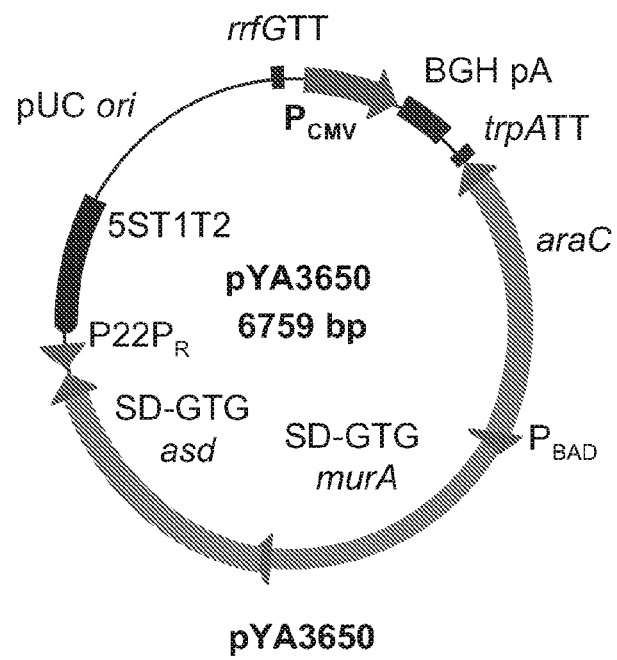
FIG. 3. Improved DNA vaccine vector pYA4545 (B) and parent vector (A).
Figure 3:
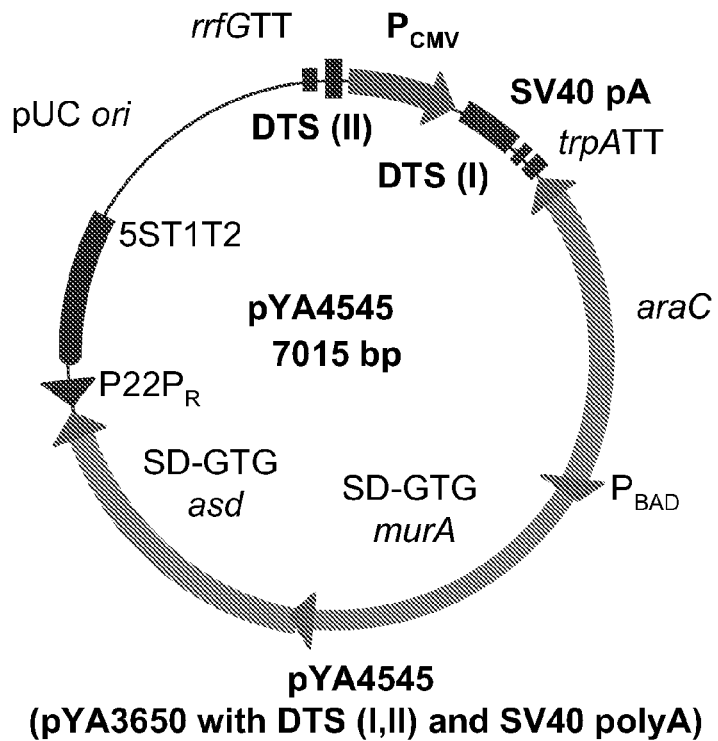
Figure 4:
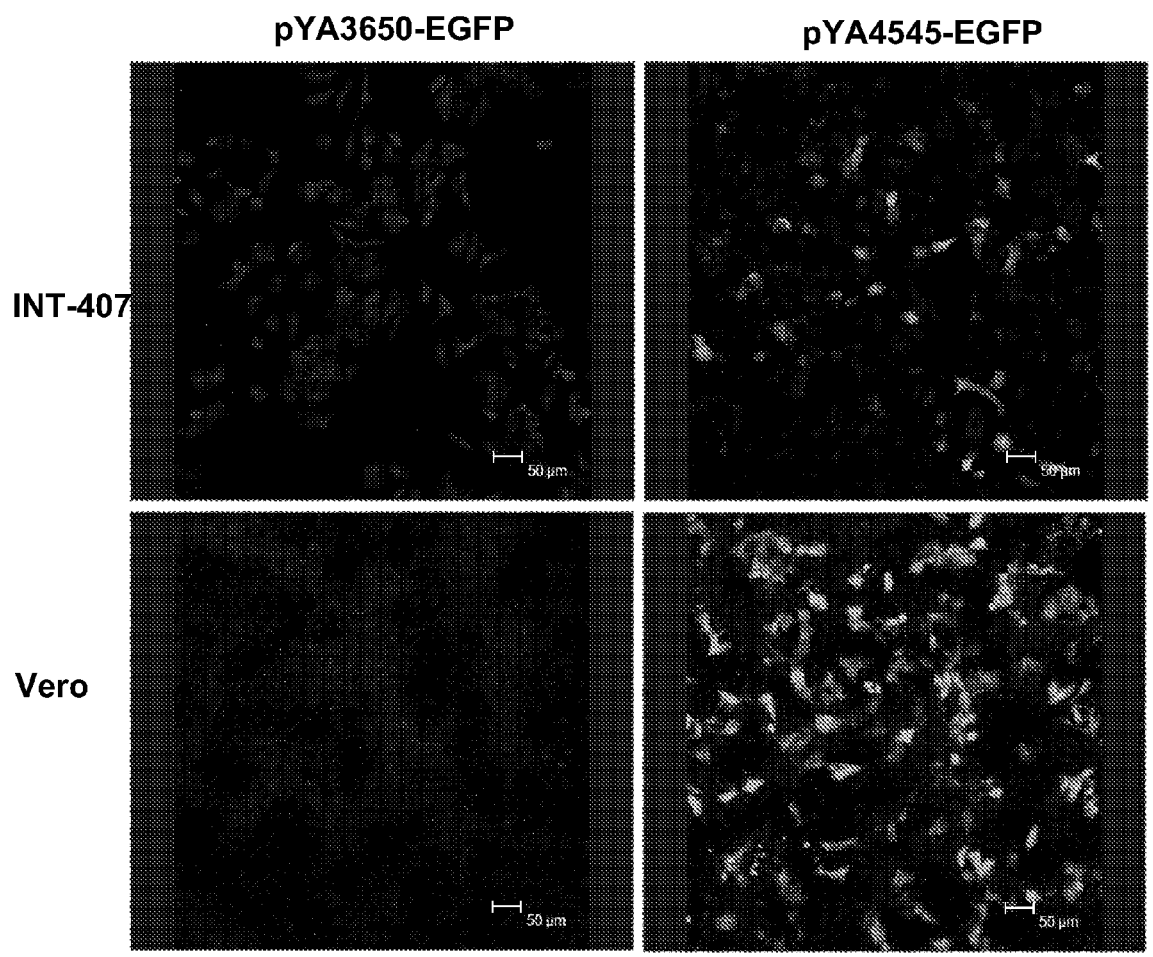
FIG. 4. Synthesis of EGFP from pYA4545 harboring EGFP gene in INT-407 cell line and Vero cell line.

Construction of *S. Typhimurium* Strains with Regulated Lysis Phenotype to Release Improved DNA Vector, with Enhanced Plasmid Nuclear Import and Resistance to Attack from Mammalian Nucleases A second regulated delayed lysis host-vector system was devised that harbors DNA vaccine vector pYA3650 with the same regulatory domain that contributes to the lysis phenotype encoded on pYA3681 but with a eukaryotic expression promoter. The *S. Typhimurium* host strain χ8888 (ΔasdA19:: TT araC $P_{BAD}$ c2 TT Δ$P_{murA7}$::TT araC $P_{BAD}$ murA, Δ(gmd-fcl)-26, ΔrelA1123, ΔendA2311, ΔaraBAD1923 ΔaraE25) includes a ΔendA mutation to eliminate the periplasmic endonuclease I enzyme (41) to increase plasmid survival upon its release into host cells. ΔaraBAD and ΔaraE mutations were also included to block arabinose catabolism with production of acid during vaccine growth and enable efficient and rapid breakdown of arabinose encountered in vivo or in intestinal contents. Other attributes of the regulated delayed lysis system are described above. It should be emphasized, that all DNA vaccine host-vector constructions derived from χ8888 with pYA3650 are strictly arabinose-dependent for growth in liquid or on solid media. Although use of non-viral DNA vaccine vectors offers advantages, such as decreasing inflammatory responses, gene expression in vivo remains much lower than observed with their viral counterparts. One reason for such low expression is that bacterial plasmids, unlike many viruses, have not evolved mechanisms to target the nucleus in non-dividing cells and make use of the cell's protein synthesis machinery to produce the antigen of interest (19, 21, 107). Plasmid nuclear import is dependent on DNA nuclear targeting sequences (DTS) (39, 40) several of which have been identified (135). The DTS frequently contain transcription factor binding sites, which allow transcription factors to bind to the plasmid in the cytoplasm and escort it to the nucleus by the nuclear localization signal-mediated machinery. The SV40 enhancer, which is known to bind to over 10 distinct transcription factors, is an excellent DTS (12). The minimum requirement for this function is a single copy of a 72-bp element of the SV40 enhancer, in combination with the CMV immediate-early gene enhancer/promoter (CMV E/P) (4). Nuclease degradation of DNA vaccine vectors after delivery and during trafficking to the nucleus is another barrier that leads to inefficient DNA vaccination. Homopurine-rich tracts in the bovine growth hormone polyadenylation signal (BGH poly A) were identified as labile sequences, and replacement of BGH poly A with SV40 late poly A has improved resistance to attack from mammalian nucleases (24, 117). To increase the efficiency of the DNA vaccine vector system, the 72 bp DTS (I) of the SV40 enhancer was inserted into pYA3650 and also replaced the BGH poly A with the SV40 late poly A resulting in pYA4050. The synthesis of eukaryotic transcription factors, e.g., NF-κB and AP-2, are stimulated by *Salmonella* infection (25, 129, 139). Newly synthesized transcription factors can bind to non-viral DNA vaccine vectors in the cytoplasm, allowing the nuclear locating signal to mediate import of plasmid DNA into the nucleus. Depending on the position of these transcription factor binding sites relative to the transgene, the binding sites could also act as transcriptional enhancers that further increase gene expression levels. Therefore, artificial DNA binding sites for NF-κB and AP-2 (SEQ ID NO:1-GGGGACTTTCCGGGGACTTTCCTC-CCCACGCGGGGGACT TTCCGC-CACGGGCGGGGACTTTCCGGGGACTTTCC) were designed and inserted them upstream of CMV E/P in pYA4050 as a DNA nuclear targeting and enhancer sequence to yield the improved DNA vaccine vector pYA4545 (FIG. 3). The plasmid pYA4545 allows rapid nuclear import and high-level synthesis of the enhanced green fluorescent proteins (EGFP) in multiple tested mammalian cells (FIG. 4).

Example 5

The Roles of TIR-Like Protein a (TlpA), Deubiquitinase (SseL) and a Member of the YopJ/Avr Family of Proteins (AvrA) in *Salmonella*-Induced Host Cell Apoptosis Invasive *Salmonella* induces pyroptosis/apoptosis in a fraction of infected macrophages (46, 93). Macrophages infected by *Salmonella* triggers caspase-1-dependent proinflammatory programmed cell death, i.e., a recently recognized process termed pyroptosis, which is distinguished from other forms of cellular demise by its unique mechanism, features and inflammatory outcome (17, 45, 63, 102). *Salmonella* strains harboring mutations in the genes encoding the SPI-1 T3SS, including invA, invG, invJ, prgH, sipB, sipC, sipD and spaO, are not cytotoxic (27, 70, 97, 108). *Salmonella Enteritidis* gene tlpA (for (TIR)-like protein A) is predicted to encode a protein with homology to the Toll/interleukin-1 receptor (TIR) domain of the mammalian Toll like receptors (TLRs) (53, 83, 111). Like many important bacterial virulence factors, TlpA also acts as mimics of mammalian proteins to subvert normal host cell processes. As analogous to the previously characterized SipB protein of *S. Typhimurium*, TlpA promotes activation of the protease caspase-1, resulting in caspase-dependent secretion of IL-1β and host cell apoptosis. *Salmonella* deubiquitinase (SseL) is required for *Salmonella*-induced cytotoxicity of macrophages. *Salmonella* sseL mutant strains did not show a replication defect or induce altered levels of cytokine production upon infection of macrophages, but were defective for the delayed cytotoxic effect. *Salmonella* AvrA effector presumably involved in the metabolism of ubiquitin or related molecules, have evolved to inhibit the anti-apoptotic NF-κB pathway. Taken together, TlpA, SseL and AvrA effectors are directly involved in inducing apoptosis of host cells infected by *Salmonella*, it is hypothesized that release of over-synthesized TlpA, SseL and AvrA effectors by a *S. Typhimurium* strain with the regulated lysis phenotype after the strain accumulated in tumor tissue, could be a potential means to further enhance inducing apoptosis in tumor cells.

Materials and Methods for Examples 6-8

Bacterial Strains, Media and Bacterial Growth

All strains are derived from the *S. Typhimurium* strain UK-1 (35). Defined deletion mutations with and without specific insertions are described in the following sections. These genetic constructions can be introduced into any strain using suicide vectors, transduction and novel allele replacement methods previously described (73, 127). LB broth and agar (94) are used as complex media for propagation and plating of bacteria. MacConkey agar with 0.5% lactose (Lac) and arabinose (Ara) will be used to enumerate bacteria from mice. Bacterial growth is monitored spectrophotometrically and/or by plating.

Molecular and Genetic Procedures

Methods for DNA isolation, restriction enzyme digestion, DNA cloning and use of PCR for construction and verification of vectors are standard (121). *E. coli* K-12 strain 6212 was used for initial cloning. DNA sequence analysis may be performed at nominal charge in the DNA Sequence Laboratory in the School of Life Sciences. All oligonucleotide and/or gene segment syntheses may be done commercially. Phage P22HTint (123, 124) may be used to transduce mutations of a selectable phenotype from one *S. Typhimurium* strain into other strains. Conjugational transfer of suicide vectors may be performed by standard methods (104, 118) using the suicide vector donor strain χ7213. Plasmid constructs may be evaluated by DNA sequencing, ability to complement various *S. Typhimurium* mutant strains and for ability to specify synthesis of proteins using gel electrophoresis and western blot analyses.

Strain Characterization.

Multiple gene modifications are routinely included in the strains, and complete biochemical and genetic characterizations are performed after every step in strain construction for stability of plasmid maintenance, integrity and selected protein synthesis ability when strains are grown in the presence of arabinose and/or DAP over a 50 generation period. Moreover, an LPS gel is run to make sure rough variants are not selected (64). Multiple mutant strains therefore grow at almost the same rate and to the same density as wild-type parental strains when grown under permissive conditions. With many regulated functions, it is critical that strains commence to synthesize selected protein and often deliver them prior to cell lysis. Strains synthesizing GFP have been used to monitor these events. So far, selected protein synthesis commences several divisions before lysis commences. Engineered *Salmonella* strain stability are also evaluated, due to possible recombinational events, and to date have detected no problems. Motility tests and use of specific antisera for given flagellar antigens may be used to reveal presence of flagella. Presence of fimbrial adhesins may be assayed using agglutination of yeast and red blood cells. Metabolic attributes of candidate vaccine strains may be evaluated using API-20E tests.

Cell Biology.

The ability of various constructed *Salmonella* strains to attach to, invade into and survive in various murine and human epithelial and/or macrophage cell lines may be quantitated by well established methods (36, 54) that are routinely used.

Cell Culture and Cylindroid Formation.

Human colon cancer cells, LS174T may be obtained from the American Type Culture Collection (Manassas, Va.) and cultured in Dulbecco's modified Eagle's medium (DMEM) with 10% fetal bovine serum (FBS) and 26 mM HEPES buffer at 37 C and 5% CO2. Cell aggregates may be grown in tissue culture flasks coated with 20 mg/ml poly (2-hydroxyethyl methacrylate) for 9 days to form spheroids. Formation of tumor cylindroids may be done as described by Kasinskas (78). Briefly, cylindroids may be formed by constraining spheroids between the bottom surface of a 96-well plate and the top surface of a set of polycarbonate cylindrical plugs attached to a polycarbonate lid. The diameter of each cylindroid is dependent on the initial size of the spheroid used in its formation. Spheroids ranging from 150 to 1,000 μm in diameter will be selected based on their size, symmetry, and overall integrity. After being constrained, cylindroids were allowed to equilibrate for 22 h in 100 μL DMEM to relieve mechanical stress and establish oxygen and metabolic gradients before subjection to further experimentation (78).

Establish LS174T Cell Line Stably Over Expressing Red Fluorescence Protein RFP.

RFP open reading frame may be inserted into plasmid pSELECT-puro-MCS to result in plasmid pSELECT-puro-RFP. This plasmid may be transfected into LS174T cells. After 2 days of culture, cells may be selected by addition of puromycin to the culture medium. Subsequently, puromycin-resistant cells may be cloned into sublines expressing RFP, designated as LS174T/RFP cells.

Establish a Real-Time Whole-Body Imaging of an Orthotopic Colon Cancer Model Stably.

All animal experiments may be performed according to the National Institutes of Health Guide for Care and Use of Experimental Animals with approve by the Animal Care Committee of Arizona State University. Male BALB/c six to eight-week old mice may be used in the study. Although mouse subcutaneous tumor models are easy to establish and monitor, it is clear that this model cannot replicate the original anatomic site of colorectal cancer. Due to the difference in microenvironment, colorectal cancer cells growing under the skin have been shown to change their phenotype and almost always fail to progress and metastasize (62, 81). In fact, tumor response to therapy can vary dramatically depending on whether cancer cells are implanted in an ectopic (subcutaneous) versus orthotopic location (142). Orthotopic mouse models of colorectal cancer, which feature cancer cells growing in their natural location, replicate human disease with high fidelity (134). To establish an orthotopic mouse model, subconfluent cultures of LS174T/RFP cells may be harvested by treatment with 0.25% trypsin and 1 mM EDTA-4Na in Hank's balanced salt solution (HBSS), washed and suspended at a density of $2 \times 10^8$ cells/ml in DMEM. The single cell suspension of LS174T/RFP ($1 \times 10^7$ cells/100 µl/mouse) may be injected into the mouse cecal wall (134). Tumor-bearing mice (after tumors reach a size that is clearly visible) may be used to monitor and measure the accumulation and anti-tumor activity of the RAS strains in vivo.

Statistical Analysis.

Experiments may be performed three times and the data may be presented as mean±SD. Student's t-test will be carried out to assess the statistical difference. P<0.05 may be considered to be significant.

Example 6

To Construct and Characterize Recombinant Attenuated *S. Typhimurium* (RAS) Strains that are Hyper-Invasive, Allow Constitutive Over-Synthesis of Serine and Aspartate Chemoreceptors to Maximize *Salmonella* Localization in Tumor Quiescence, Display Regulated Delayed Protein Synthesis Attributes to Facilitate Maximal Colonization of Tumor Tissues and Exhibit Regulated Delayed Lysis Phenotype Introduction.

The starting *S. Typhimurium* delivery strain has the genotype ΔasdA27::TT araC $P_{BAD}$ c2 $\Delta P_{murA25}$::TT araC $P_{BAD}$ murA (to enable regulated delayed lysis), Δ(wza-wcaM)-8 (to block synthesis of colanic acid that can enable survival of bacteria undergoing cell wall-less death), ΔrelA198::araC $P_{BAD}$ lacI TT (to enable regulated delayed synthesis of protective antigens), Δ(araC $P_{BAD}$)-18::P22 $P_R$ araBAD (to block arabinose catabolism with production of acid during vaccine growth and enable efficient and rapid breakdown of arabinose encountered in vivo or in intestinal contents), ΔpagP81::$P_{lpp}$ lpxE (to diminish toxicity of lipid A) and ΔendA2311 (to reduce destruction of DNA vaccines upon their release during lysis by eliminating endonuclease). Our core genotype includes the mutations of ΔasdA27::TT araC $P_{BAD}$ c2 and $\Delta P_{murA25}$::TT araC $P_{BAD}$ murA. The much-improved $\Delta P_{murA25}$::TT araC $P_{BAD}$ murA deletion-insertion mutation has a tightly-regulated araC $P_{BAD}$ cassette and a better spacing of the regulatory sequences. A strain with this deletion-insertion mutation when grown in medium with 0.05 percent arabinose produces the MurA enzyme at the same level as the wild-type *S. Typhimurium* UK-1 strain.

The effectiveness of most chemotherapeutics is limited by their inability to deeply penetrate into tumor tissue and their ineffectiveness against quiescent cells (80, 105). Motile *S. Typhimurium*, which are specifically attracted to compounds produced by quiescent cancer cells, could overcome this therapeutic barrier (67, 113). *S. Typhimurium* accumulate within the necrotic regions of tumors formed both in vitro and in vivo, and chemotaxis is essential to initiate bacterial accumulation (49, 78). There are five chemotaxis-specific transmembrane receptors in *S. Typhimurium* (16), four of which bind specific chemical ligands including aspartate/maltose, serine, citrate, and ribose/galactose (14, 66, 143). It has been shown that chemoreceptors direct bacterial chemotaxis within cylindroids: the aspartate and maltose receptor (Tar) initiates chemotaxis toward cylindroids, the serine receptor (Tsr) initiates penetration, and the ribose/galactose receptor (Trg) directs *S. Typhimurium* toward necrosis (77). By deleting the ribose/galactose receptor Trg, bacterial accumulation took place in locations to tumor quiescence, and had a greater individual effect on inducing apoptosis than a wild-type strain (77). A better means of down regulating the trg gene in vivo is to make a $\Delta P_{trg}$::rhaRS-$P_{rhaB}$ trg construction that will result in cessation of Trg synthesis in vivo with its level decreasing by half after every cell division. Furthermore, overexpression of tar results in longer response to aspartate and maltose (122). The role of chemoreceptors in enhancing the accumulation of *S. Typhimurium* within quiescent cells in tumor may be explored by up-regulating expression of the Tar and Tsr chemoreceptors.

Construction of the RAS Strain that Preferably Localize in Tumor Tissue.

Figure 5:
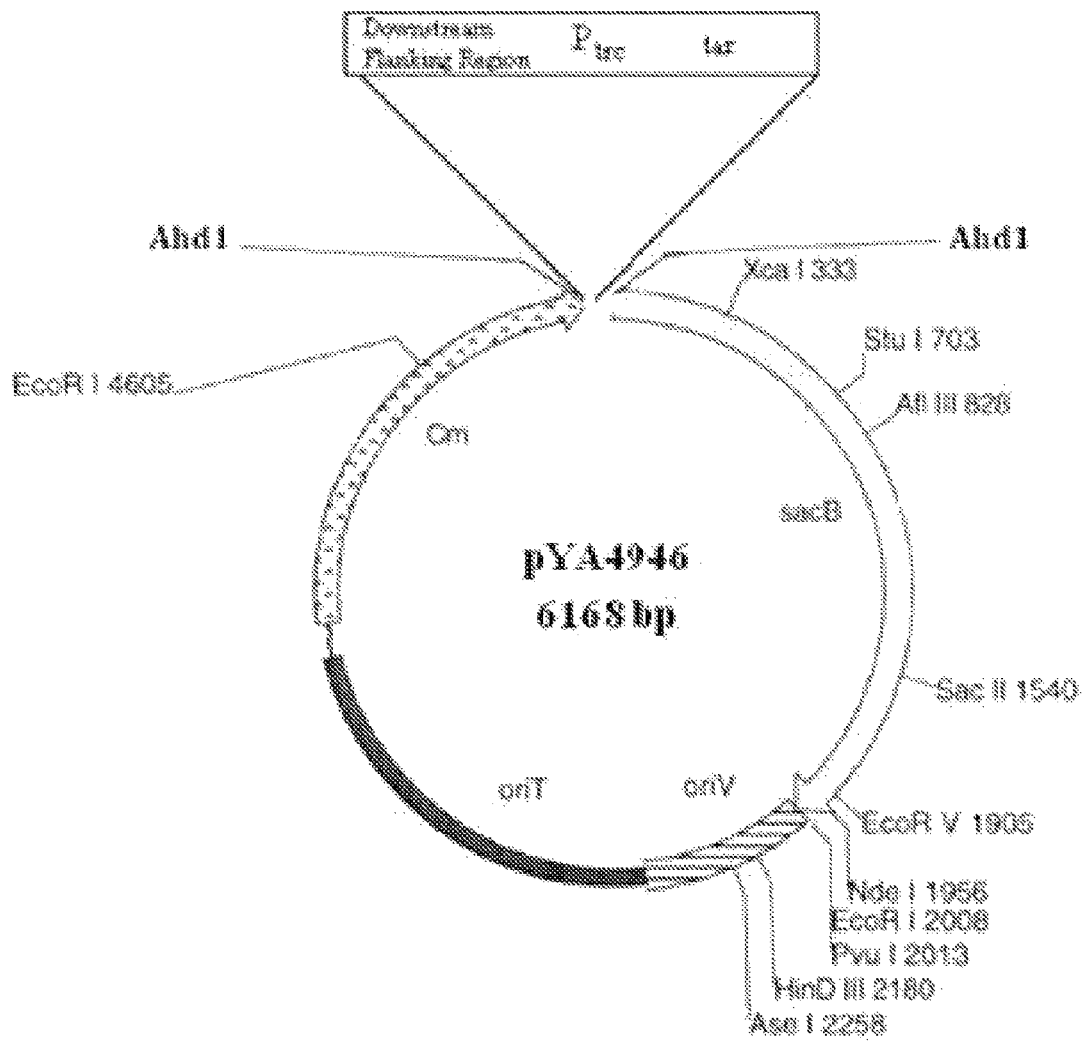
FIG. 5. Depicts an illustration of the suicide vector pYA4946.
Figure 6:
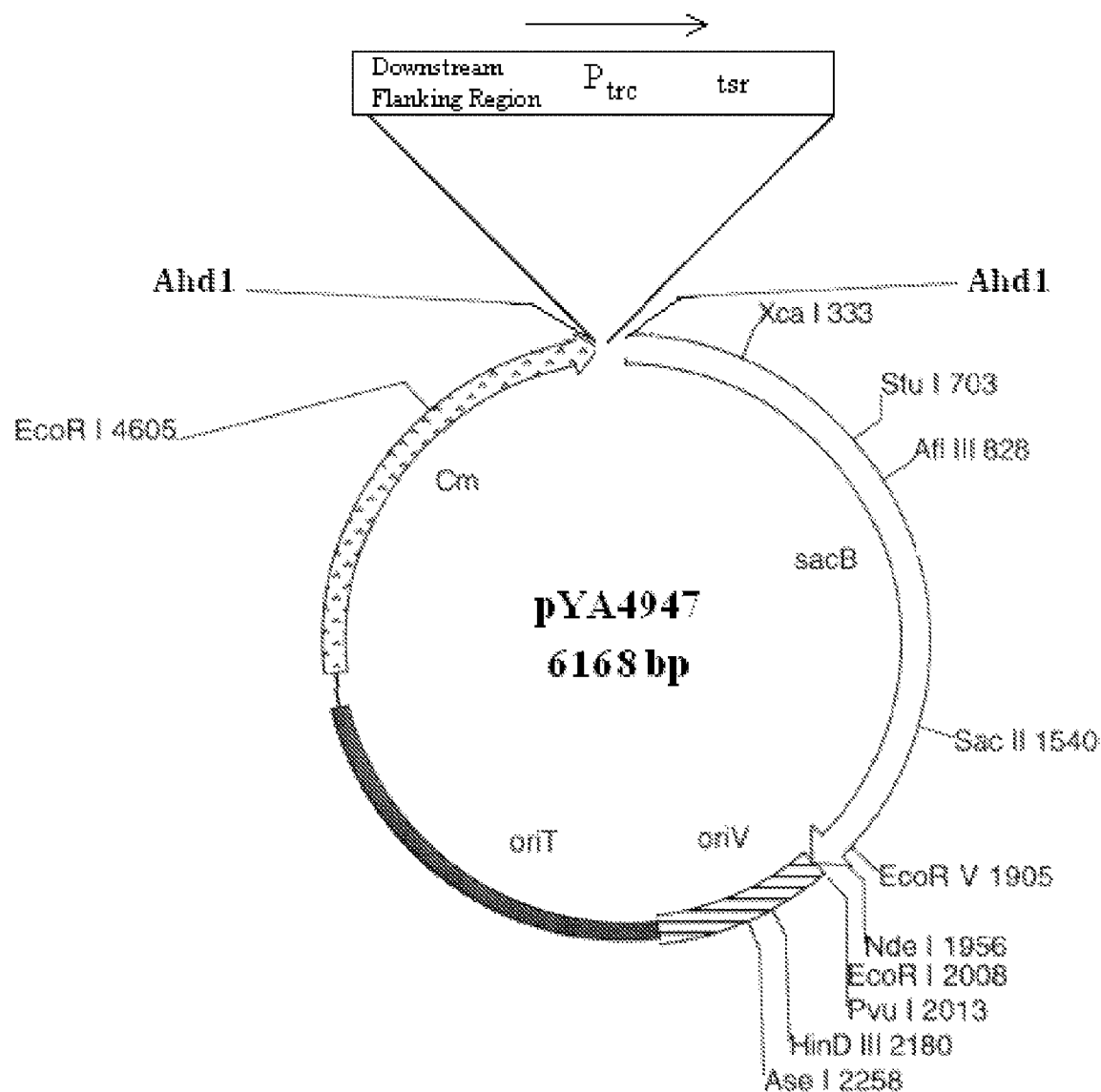
FIG. 6. Depicts an illustration of the suicide vector pYA4947.
Figure 7:
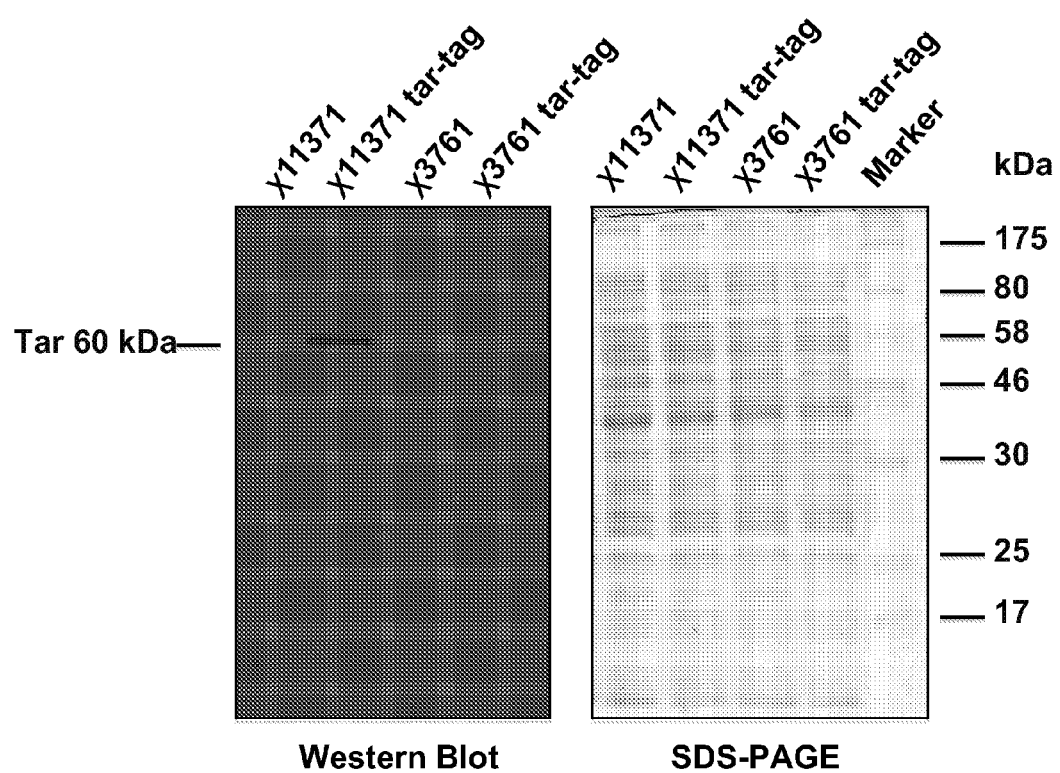
FIG. 7. Confirmation of the over-expression of Tar in strain χ11371 by western blot analysis using mouse anti-c-Myc tag and goat-anti-mouse IgG antisera.
Figure 8:
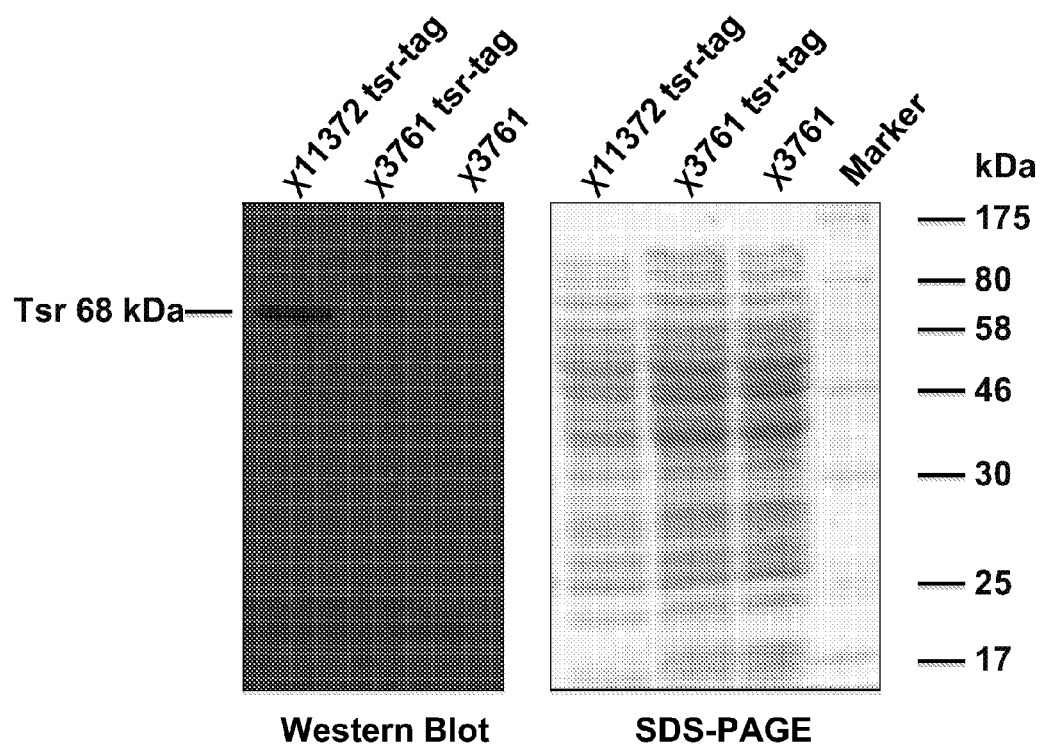
FIG. 8. Confirmation of the over-expression of Tsr in strain χ11372 by western blot analysis using mouse anti-c-Myc tag and goat anti-mouse IgG antisera.
Figure 9:
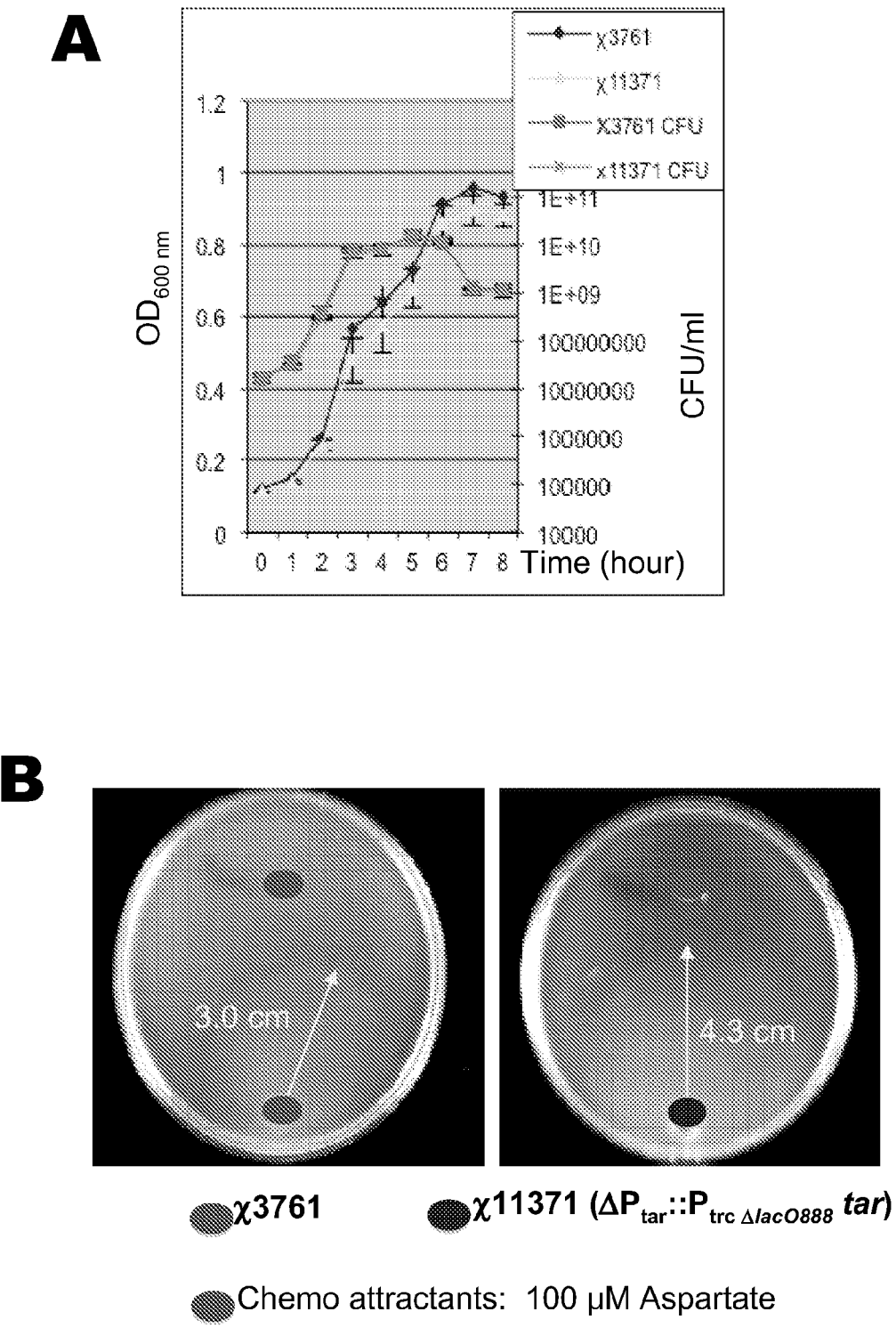
FIG. 9. Chemotaxis assay of strain harboring tar deletion-insertion mutation versus its parent *S. Typhimurium* UK-1 wild-type strain. (A) depicts the OD600 versus time and CFU/ml versus time, (B) illustrates the chemotaxis assay, and (C) depicts the distance traveled by each strain.
Figure 9C:
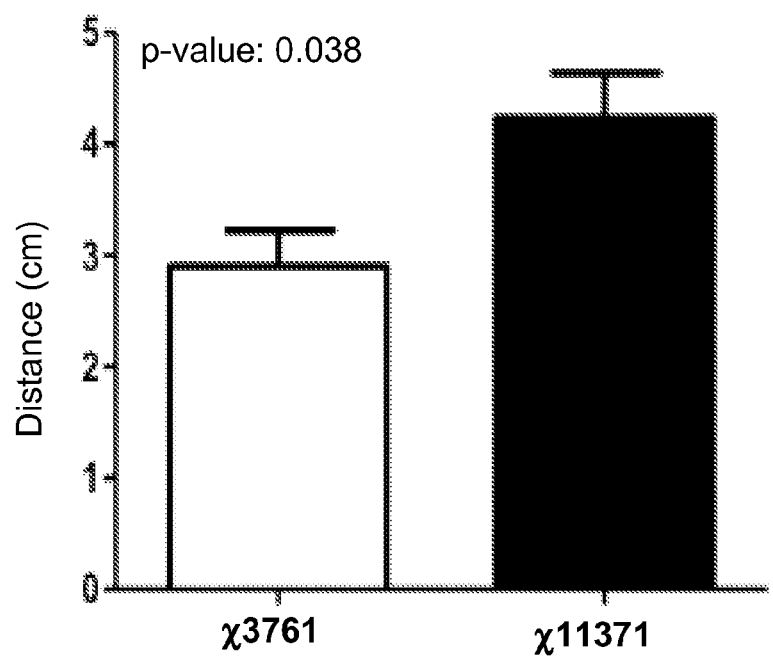
Figure 10A:
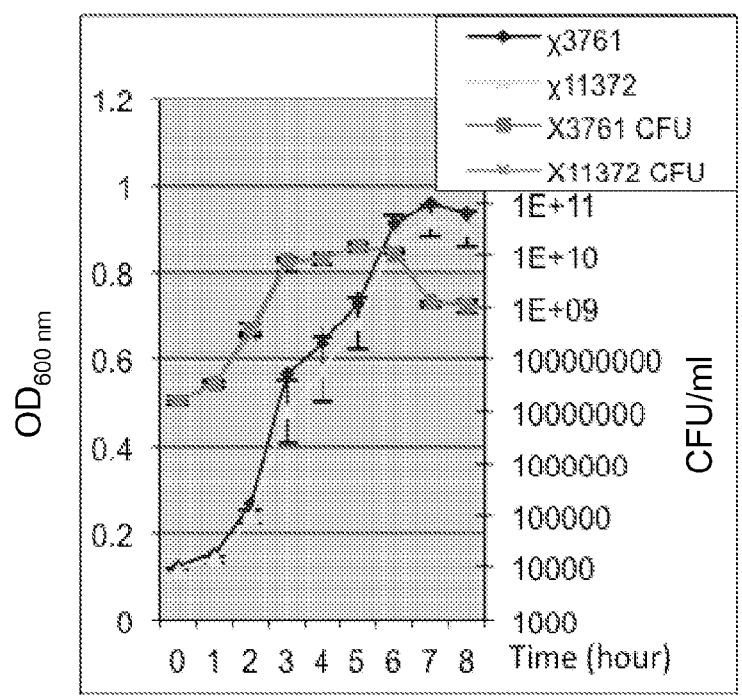
FIG. 10. Chemotaxis assay of strain harboring tsr deletion-insertion mutation versus its parent *S. Typhimurium* UK-1 wild-type strain. (A) depicts the OD600 versus time and CFU/ml versus time, (B) illustrates the chemotaxis assay, and (C) depicts the distance traveled by each strain.
Figure 10:
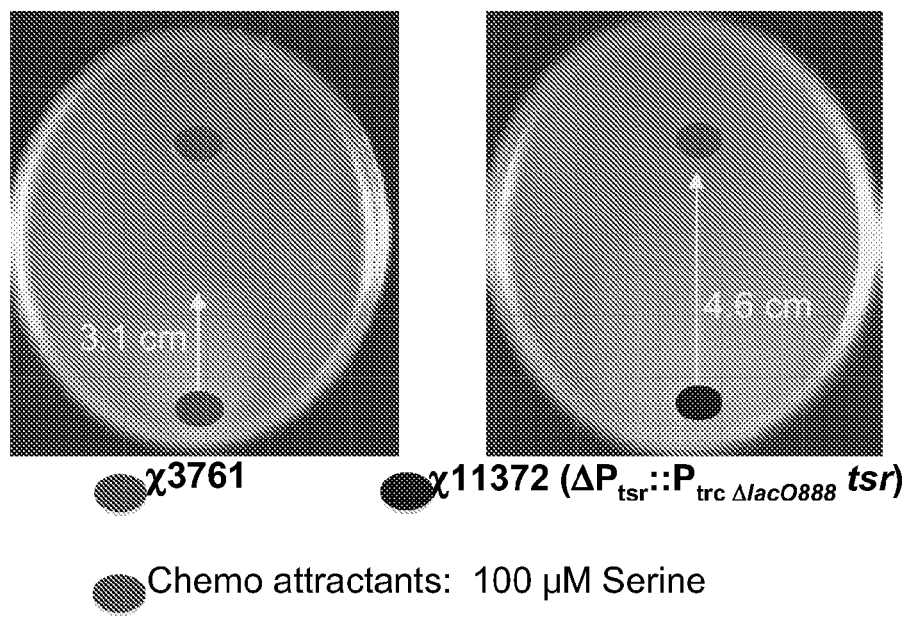
Figure 10:
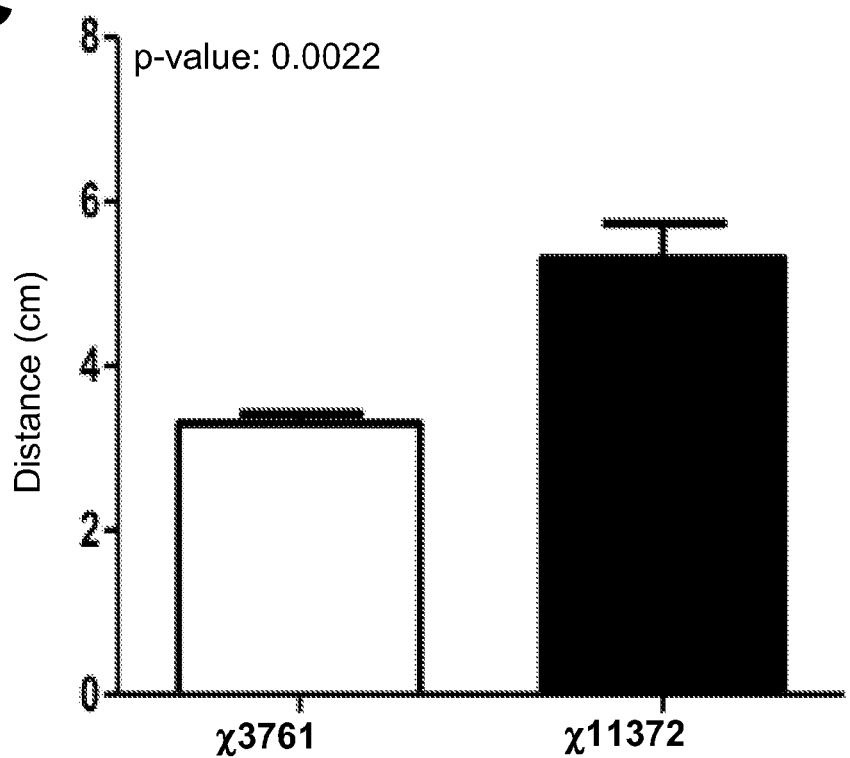

It is hypothesized that up-regulating the synthesis of the Tar and Tsr chemoreceptors could enhance the accumulation of the *Salmonella* in tumor quiescence. Therefore, the promoters of tar and tsr genes of strain χ11409 were replaced, respectively, with the $P_{trc\ \Delta lacO888}$ promoter that lacks the operator lacO sequence to enable constitutive synthesis of Tar and Tsr even when the lacI gene in the host strain is expressed. We have constructed suicide vectors pYA4946 (pRE112 based suicide vector for construction of $\Delta P_{tar}$::$P_{trc\Delta lacO888}$ tar deletion-insertion mutation) and pYA4947 (pRE112 based suicide vector for construction of $\Delta P_{tsr}$::$P_{trc\ \Delta lacO888}$ tsr deletion-insertion mutation) (FIG. 5 and FIG. 6). The $\Delta P_{tar}$::$P_{trc\Delta lacO888}$ tar and $\Delta P_{tsr}$::$P_{trc\ \Delta lacO888}$ trc deletion-insertion mutations were introduced into *S. Typhimurium* UK-1 wild-type strain χ3761, resulting in strains χ11371($\Delta P_{tar}$::$P_{trc\Delta lacO888}$ tar) and χ11372 ($\Delta P_{tsr}$::$P_{trc\ \Delta lacO888}$ tsr). The over-expressions of Tar in strain χ11371 and Tsr in strain χ11372 were confirmed by western blot analysis using mouse anti-Flag tag and mouse anti-c-Myc tag, respectively. Goat-anti-mouse IgG antisera served as secondary antibody (FIG. 7 and FIG. 8). The chemotaxis assays were carried out, and strain χ11371 was significantly attracted by 50 urn and 100 µm aspartate on swarm plate comparing with its parent *S. Typhimurium* UK-1 wild-type strain χ3761 (FIG. 9). Furthermore, strain χ11372 was significantly attracted by 10 µm serine on swarm plate (FIG. 10). These two mutations were also introduced into regulated delayed lysis strain χ11283 resulting in strains χ11374 (ΔasdA27::TT araC $P_{BAD}$ c2 Δ(araC $P_{BAD}$)-5::P22 $P_R$ araBAD Δ(wza-wcaM)-8 Δpmi-2426 ΔrelA198::araC $P_{BAD}$ lacI TT $\Delta P_{MurA25}$::TT araC $P_{BAD}$ murA ΔpagP81::$P_{lpp}$ lpxE $\Delta P_{Tar}$::$P_{trc\ \Delta lacO888}$ tar) and χ11375 (ΔasdA27::TT araC $P_{BAD}$ c2 Δ(araC $P_{BAD}$)-5::P22 $P_R$ araBAD Δ(wza-wcaM)-8 Δpmi-2426 ΔrelA198::araC $P_{BAD}$ lacI TT $\Delta P_{murA25}$::TT araC $P_{BAD}$ murA ΔpagP81::$P_{lpp}$ lpxE $\Delta P_{tsr}$::$P_{trc\ \Delta lacO888}$ tsr). The $\Delta P_{tar}$::$P_{trc\ \Delta lacO888}$ tar and $\Delta P_{tsr}$::$P_{trc\ \Delta lacO888}$ tsr deletion-insertion mutations were also introduced into strain χ11409. The resulting strains were strain χ11410 ($\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ lpxE ΔendA2311 $\Delta P_{tar}$::$P_{trc\ \Delta lacO888}$ tar) and strain χ11514 ($\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ lpxE ΔendA2311 $\Delta P_{tar}$::$P_{trc\ \Delta lacO888}$ tar $\Delta P_{tsr}$::$P_{trc\ \Delta lacO888}$ tsr).

Construction of the RAS Strain that Preferably Localizes in Tumor Quiescence.

Figure 11:
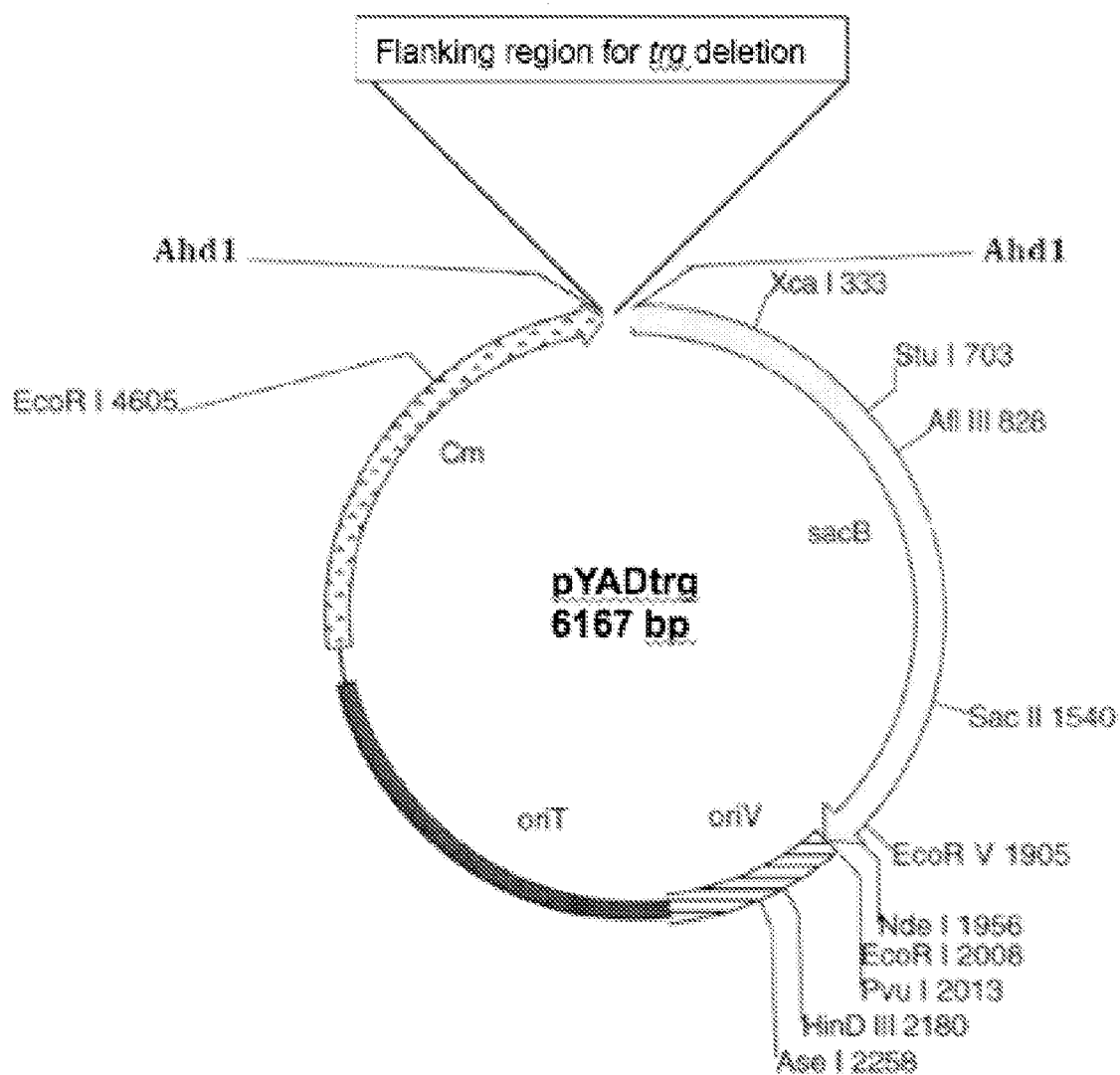
FIG. 11. Depicts an illustration of the suicide vector pYA5077.
Figure 12:
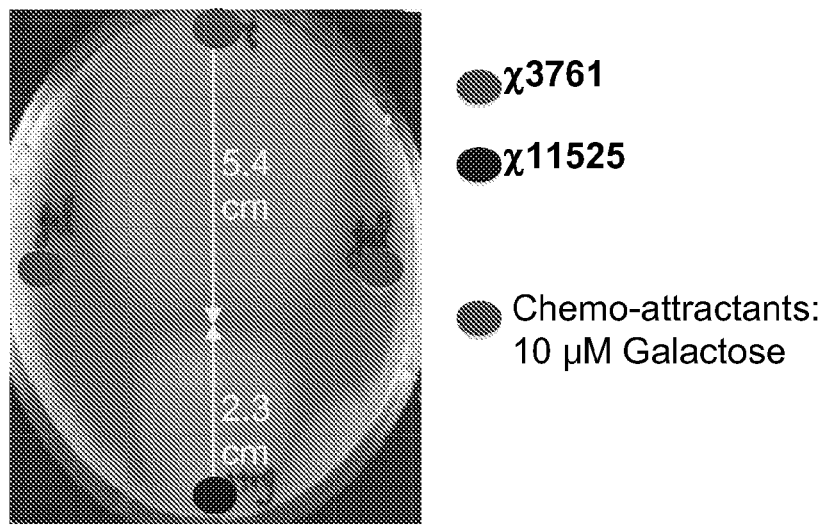
FIG. 12. Chemotaxis assay of strain harboring trg deletion mutation versus its parent *S. Typhimurium* UK-1 wild-type strain. (A) illustrates the chemotaxis assay, and (B) depicts the distance traveled by each strain.
Figure 12:
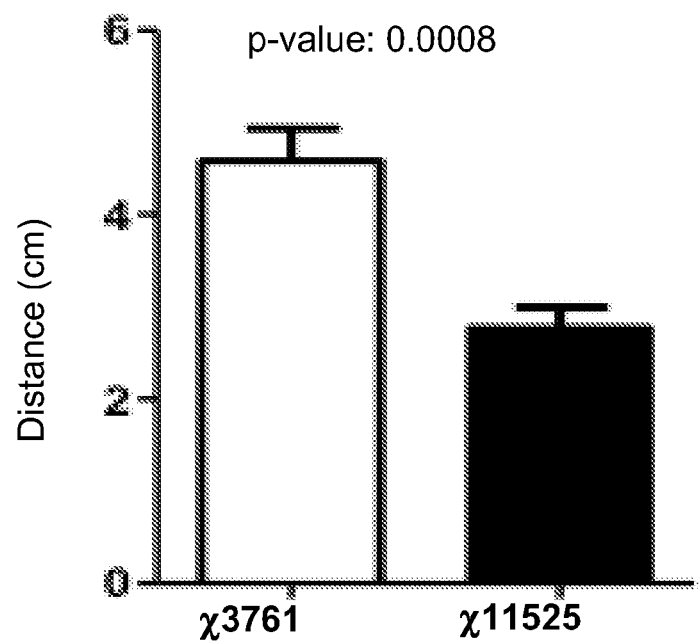

By deleting the ribose/galactose receptor Trg, bacterial accumulation took place in locations to tumor quiescence, and had a greater individual effect on inducing apoptosis than a wild-type strain. We have constructed suicide vector pYA5077 (pRE112 based suicide vector for construction of Δtrg mutation) (FIG. 11). The Δtrg mutation was introduced into *S. Typhimurium* UK-1 wild-type strain χ3761, resulting in strain χ11525. The chemotaxis assays was performed, and strain χ11525 was not attracted by 10 μM galactose on swarm plate (FIG. 12). Therefore, the mutation Δtrg was included into χ11514. The resulting strain was χ11515 ($\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 PR araBAD ΔpagP81::$P_{lpp}$ IpxE ΔendA2311 $\Delta P_{tar}$::$P_{trc\ \Delta lacO888}$ tar $\Delta P_{tsr}$:: $P_{trc\ \Delta lacO888}$ tsr Δtrg). Furthermore, a better means of down regulating the trg gene in vivo is to make a construction that will result in cessation of Trg synthesis in vivo with its level decreasing by half after every cell division. In this regard, the mutation Δtrg was replaced with mutation-insertion $\Delta P_{trg}$::rhaRS-P rhaB trg. The resulting strain was χ11516 ($\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ IpxE ΔendA2311 $\Delta P_{tar}$::$P_{trc\ \Delta lacO888}$ tar $\Delta P_{tsr}$:: $P_{trc\ \Delta lacO888}$ tsr $\Delta P_{trg}$::rhaRS-$P_{rhaB}$ trg).

Construction of the *S. Typhimurium* Strain that Displays Super-Invasive Phenotype.

It is evident that an engineered *S. Typhimurium* strain whether delivering selected protein or a DNA vaccine vector will likely be improved by increasing its invasiveness. Therefore, the $\Delta P_{hilA}$::$P_{trc\ \Delta lacO888}$ hilA deletion-insertion mutation was included into strain χ11515 or strain χ11516 to result in strain χ11517 (ΔasdA27::TT araC $P_{BAD}$ c2 $\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ IpxE ΔendA2311 $\Delta P_{tar}$::$P_{trc\ \Delta lacO888}$ tar $\Delta P_{tsr}$::$P_{trc\ \Delta lacO888}$ tsr Δtrg or $\Delta P_{trg}$::rhaRS-$P_{rhaB}$ trg $\Delta P_{hilA}$:: $P_{trc\ \Delta lacO888}$ hilA).

Construction of the RAS ΔpurA Auxotrophs Strain to Selectively Colonize in the Necrotized Tumor Tissue.

The possibility of utilizing *S. Typhimurium* auxotrophs has been considered for selective growth in tumors, since the bacteria would be both attenuated for use in vivo and preferentially survive in the necrotized tissue in and around tumors, utilizing the cell lysate for its own needs. The ΔpurA mutation was introduced into strain χ11517 to result in strain χ11518 (ΔasdA27::TT araC $P_{BAD}$ c2 $\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ IpxE ΔendA2311 $\Delta P_{tar}$:: $P_{trc\ \Delta lacO888}$ tar $\Delta P_{tsr}$:: $P_{trc\ \Delta lacO888}$ tsr Δtrg or $\Delta P_{trg}$::rhaRS-$P_{rhaB}$ trg $\Delta P_{hilA}$::$P_{trc\ \Delta lacO888}$ hilA Δ purA). We have also constructed balanced-lethal vector-host system strain χ11203 (ΔasdA ΔpurA) and regulated delayed lysis system strain χ11204 (ΔasdA::TT araC $P_{BAD}$ c2 ΔmurA::TT araC $P_{BAD}$ murA Δ (gmd-fcl) ΔrelA::araC $P_{BAD}$ lacI TT Δpmi ΔaraBAD ΔpurA) to test the effects of ΔpurA mutation on selective colonization in the necrotized tumor tissue. The plasmids pYA4545 or pYA4545-GFP (DNA vaccine vector pYA4545 harboring prokaryotic expressing green fluorescent protein (GFP)) may then be transformed into the RAS strains χ11409, χ11410, χ11514, χ11515, χ11516, χ11517, and χ11518, respectively, to test the efforts of these modifications.

Capillary Assay to Quantify Bacterial Chemotaxis.

The ability of the RAS strains to migrate toward chemoattractant molecules may be quantified using the needle-syringe capillary assay (99). Briefly, the RAS strains χ11409 (pYA4545), χ11410 (pYA4545), χ11514 (pYA4545), χ11515 (pYA4545), χ11516 (pYA4545), χ11517 (pYA4545), and χ11518 (pYA4545) may be grown to mid-logarithmic phase, centrifuged, washed, and suspended in motility buffer to a final concentration of $3.2 \times 10^7$ CFU/ml bacteria (1, 101). Hypodermic needles (25 gauge) attached to 1 ml syringes may be filled with 0.1 ml of chemoattractant solution containing 0.1 mM serine or 1 mM aspartate. The needle-syringe assemblies may be inserted into 200 μl pipette tips containing the bacterial suspension and incubated at 35° C. for 1 h. After incubation, the content of the needles may be removed, diluted, and plated to quantify the bacterial numbers (CFU). Chemotactic ability may be reported as the ratio of the average number of bacteria that accumulated in the chemoattractant capillaries to the average number of bacteria that accumulated in the chemoattractant-free controls.

Accumulation of Bacteria in Cylindroids, Image Acquisition and Analysis.

Before inoculation into cylindroid cultures (See Materials and Methods section), the RAS strains χ11409 (pYA4545-GFP), χ11410 (pYA4545-GFP), χ11514 (pYA4545-GFP), χ11515 (pYA4545-GFP), χ11516 (pYA4545-GFP), χ11517 (pYA4545-GFP), and χ11518 (pYA4545-GFP) may be grown at 37° C. to mid-logarithmic phase ($OD_{600}$ 0.3-0.5) from single colony cultures. Individual colonies may be chosen from agar plates following confirmation of GFP expression using fluorescence microscopy. These bacterial cultures may be centrifuged at 4,000 rpm for 10 min and resuspended in DMEM with 10% FBS and 26 mM HEPES buffer to a final concentration of 500 CFU/ml. Equilibrated cylindroid cultures may be inoculated with 100 μl of 500 CFU/ml *S. Typhimurium*. Time-lapse fluorescent images may be acquired at 10-min intervals up to 304 h after inoculation using time-lapse microscopy (Nikon Eclipse TE300 Inverted Microscope). Excitation light may be shuttered between acquisitions to prevent photobleaching. To test the influence of aspartate and serine on the accumulation of RAS strains χ11409 (pYA4545-GFP), χ11410 (pYA4545-GFP), χ11514 (pYA4545-GFP), χ11515 (pYA4545-GFP), χ11516 (pYA4545-GFP), χ11517 (pYA4545-GFP), and χ11518 (pYA4545-GFP), cylindroids may be prepared as described above, except cylindroids may be equilibrated in the medium containing 1 and/or 5 mM of added aspartate or serine. Bacteria added to the cylindroids may be suspended in medium containing corresponding concentrations (1 and/or 5 mM) of aspartate or serine. The accumulation of bacteria and fluorescent dyes in cylindroids may be quantified as described by Kasinskas (78).

Analysis of Bacteria Fitness in Normal Tissue Versus Tumor Tissue in LS174T Tumor Orthotopic Mice.

The $LD_{50}$ of the RAS strains χ1409 (pYA4545), χ11410 (pYA4545), χ11514 (pYA4545), χ11515 (pYA4545), χ11516 (pYA4545), χ11517 (pYA4545), and χ11518 (pYA4545) may be determined in BALB/c mice and their abilities of colonizating mouse Peyer's patches, spleen and liver monitored. Then the accumulation of each strain in tumor versus normal tissue in LS174T tumor orthotopic mice will be monitored post i.v. or oral inoculation. The strain with the best attributes will be named as Strain H.

Discussion.

$\Delta P_{hilA}$::$P_{hilA256}$ hilA deletion-insertion mutation in *S. Typhimurium* UK-1 strain was also created, in that both upstream and downstream AT-track sequences of hilA promoter region recognized by the nucleoid-associated protein H-NS to silence hilA gene expression, were deleted to construct strain χ9974. Strain χ9974 is more invasive than wild-type *S. Typhimurium* UK-1, but less than strain χ9971 ($\Delta P_{hilA}$:: $P_{trc\ \Delta lacO888}$ hilA). If a that has $\Delta P_{hilA}$::$P_{trc\ \Delta lacO888}$ hilA mutation induces unexpected pro-inflammatory response, the $\Delta P_{NA}$:$P_{hilA256}$ hilA mutation may be considered instead. (ii) the expression levels of the selected chemoreceptors may always be modulated by changing the 2nd and 3rd codon (altering translational efficiency of mRNA), and by altering codons in the chemoreceptor genes (in order to optimize for a high-level expression in *Salmo-*

*nella*). These modifications may be included if needed and these constructs may be evaluated to establish the final RAS strain.

Example 7

To Construct and Characterize the Improved RAS Strains with Regulated Delayed Synthesis of *S. Typhimurium* T3SS Effectors SopE2 and/or SopB that Stimulate Innate Immune Responses, and to Explore the Means that Provoke the Human Immune System Introduction.

The human immune system naturally grows stronger while fighting bacteria, including *Salmonella*. The potential stimulation of innate immune responses by the ideal bacterial vector to provoke the human immune system may be investigated. It is widely believed that one of the main triggers of host inflammation is the recognition of microbial products by receptors of the innate immune system (3, 11, 76). Intestinal epithelial cells, however, are a special case in that they are exposed to massive amounts of bacterial products potentially able to activate innate immune receptors. Therefore, signaling through these receptors, particularly surface TLRs, must be prevented from uncontrolled inflammation, which would be detrimental to the host. How this negative regulation of innate immune receptor activation is exerted remains poorly understood. However, it recently has been shown that *S. Typhimurium* can stimulate innate immune responses in cultured epithelial cells through the activity of bacterial effector proteins, such as the guanidyl nucleotide exchange factor SopE2 and an inositol polyphosphatase SopB, which are delivered by its T3SS in a manner independent of innate immune receptors (20). SopE2 and SopB are good candidates to mediate the innate immune responses since they activate Rho-family GTPases in a functionally redundant manner (51, 112, 148). Rho GTPases are important regulators of gene transcription and cytokine expression in infection. One role of Rho proteins in the signaling networks is to activate nuclear factor κB (NF-κB), which is a central regulator of innate and adaptive immunity. Activation of NF-κB results in expression of many inflammatory and anti-apoptotic factors, and modulation of diverse immune responses (47, 58).

Construction of the *S. Typhimurium* Strain Exhibiting Regulated Delayed Synthesis of *S. Typhimurium* T3SS effector SopE2.

Figure 13:
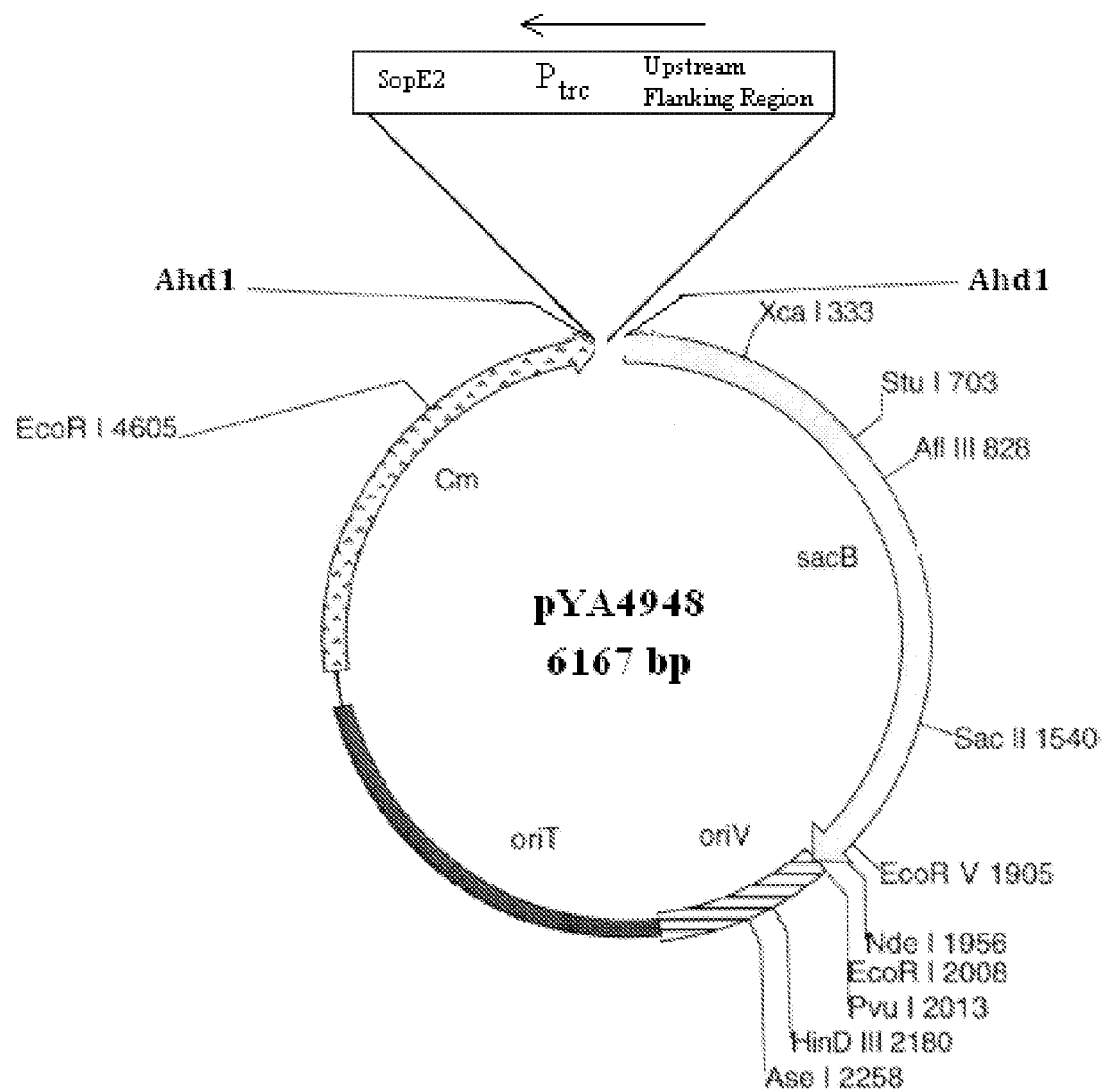
FIG. 13. Depicts an illustration of the suicide vector pYA4948.

To modulate production of the immune stimulants in RAS strains, the promoter of the sopE2 gene in the RAS strain H or its derivatives may be replaced with the $P_{trc}$ promoter to enable the regulated delayed expression of the sopE2 gene facilitating a delayed stimulation of the immune system. This may avoid an unexpected level of pro-inflammatory responses before *Salmonella* colonization since growth of the RAS strain in LB broth with 0.2% arabinose causes synthesis of LacI due to the ΔrelA198::araC $P_{BAD}$ lacI TT deletion-insertion mutation. We have constructed suicide vector p YA5077 (pRE112 based suicide vector for construction of $\Delta P_{sopE2}$::$P_{trc}$ sopE2 deletion-insertion mutation) (FIG. 13). The $\Delta P_{sopE2}$::$P_{trc}$ sopE2 deletion-insertion mutation was introduced into *S. Typhimurium* UK-1 wild-type strain χ3761, resulting strain χ11376 ($\Delta P_{sopE2}$::$P_{trc}$ sopE2). This mutation was also introduced into regulated delayed lysis strain χ11283, resulting strains χ11376 (ΔasdA27::TT araC $P_{BAD}$ c2 Δ(araC $P_{BAD}$)-5::P22 $P_R$ araBAD Δ(wza-wcaM)-8 Δpmi-2426 ΔrelA198::araC $P_{BAD}$ lacI TT $\Delta P_{MurA25}$::TT araC $P_{BAD}$ murA ΔpagP81::$P_{lpp}$ IpxE $\Delta P_{sopE2}$::$P_{trc}$ sopE2). The $\Delta P_{sopE2}$::$P_{trc}$ sopE2 deletion-insertion mutation will also be introduced into Strain H. This may result in Strain I. the genotype of strain I will most likely be (ΔasdA27::TT araC $P_{BAD}$ c2 $\Delta P_{murA25}$::TT araC $P_{BAD}$ murA Δ(wza-wcaM)-8 ΔrelA198::araC $P_{BAD}$ lacI TT Δ(araC $P_{BAD}$)-18::P22 $P_R$ araBAD ΔpagP81::$P_{lpp}$ IpxE ΔendA2311 $\Delta P_{hilA}$::$P_{trc\ \Delta lacO888}$ hilA ΔpurA $\Delta P_{tar}$:: $P_{trc\ \Delta lacO888}$ tar $\Delta P_{tsr}$::$P_{trc\ \Delta lacO888}$ tsr Δtrg or $\Delta P_{trg}$::rhaRS-$P_{rhaB}$ trg $\Delta P_{hilA}$:: $P_{trc\ \Delta lacO888}$ hilA ΔpurA $\Delta P_{sopE2}$::$P_{trc}$ sopE2). The regulated delayed synthesis of SopE2 will be confirmed in these strains by western blot using anti-SopE2 antibody.

Evaluation of the Improved RAS Strain by Monitoring Innate Immune Responses.

*S. Typhimurium* induces innate immune responses in cultured epithelial cells. The transcriptional program stimulated by wild-type *S. Typhimurium* infection that activates several genes whose products are pro-inflammatory such as several chemokines (Interleukin-8 (IL-8), IL1a, IL11, IL1 R1 and IL4R, etc). The *Salmonella* effector SopE2 activates Rho-family GTPases, which can lead to MAPK and NF-κB activation (26, 61, 140). Therefore, the ability of the RAS strain over-expressing SopE2 to stimulate innate immune responses may be investigated by examining its effect on the expression of IL-8 and activation of p38 MAPK as described below.

Detect the Stimulation of IL-8 Expression.

The RAS Strain H (pYA4545) and Strain I (pYA4545) may be grown at 37° C. over night in the medium with arabinose starvation to release $P_{trc}$ promoter from LacI repressor. Human intestinal Int-407 cell may be infected by the RAS Strain H (pYA4545) or Strain I (pYA4545). Two days after infection, infected cells may be lysed and the levels of IL-8 may be determined using Human IL-8 ELISA Kit (BioVendor Laboratory Medicine, Inc., Brno, CZ).

Detect the Activation of p38 MAPK by Measuring the Level of Phospho-P38 MAPK.

The 48 h post-infected human intestinal Int-407 cells by RAS Strain H (pYA4545) and Strain I (pYA4545) may be lysed with the lysis buffer (10 mM Tris-HCl, pH 7.5, 40 mM Na pyrophosphate, 5 mM EDTA, 150 mM NaCl, 1% NP-40, 0.5% Na-Deoxycholate, 0.025% SDS, 1 mM Na orthovanadate and complete protease inhibitor cocktail (Roche)). Proteins from cell lysates may be separated by SDS-PAGE, and phospho-P38 MAPK, total P38 MAPK may be examined by western immunoblotting using mouse anti-phospho-P38 [Thr 180, Tyr 182] (Cell Signaling Technology, Danvers, Mass.) and rabbit anti-P38, while actin may be used as a control and detected using rabbit anti-actin (Santa Cruz Biotechnology, Santa Cruz, Calif.).

Discussion.

If necessary, sopE2 expression level may be enhanced by changing the sopE2 start codon from GTG to ATG. The best candidate from these studies may be included in the RAS strain for anti-cancer agent delivery.

Example 8

To Construct and Evaluate an Improved RAS Delivery System Allowing Oversynthesis and Release of a Bacterial Virulence Factor Controlled by a *Salmonella* Promoter Preferentially Activated Inside Tumors, and Simultaneous Release of a DNA Vaccine Vector Encoding a Tumor-Specific Synthesized Fas Ligand and/or TRAIL to Trigger Tumor Apoptosis Introduction.

Invaded *Salmonella* can induce pyroptosis/apoptosis in a fraction of infected macrophages. *Salmonella Enteritidis*

TIR-like protein Δ(TlpA) is involved in induction of the host cell apoptosis (Example 5). An improved RAS strain described above may be designed and constructed to over-synthesize TlpA after they accumulate in tumor cells. Over-synthesized TlpA may be released in the tumor tissues by regulated cell lysis after *Salmonella* colonizes to induce tumor cell apoptosis. Success of gene therapy strategies for cancer by using genetic elements or toxic molecules largely depends on the cancer-specific delivery and expression of the therapeutic molecules at high level (65, 86, 138). It is known that the promoter of *S. Typhimurium* ansB gene (encoding periplasmic L-asparaginase II) is preferentially activated inside tumors (6, 68). The potential of genetically engineered promoter of ansB for tumor-specific expression of TlpA may be investigated to enhance induction of the apoptosis in tumor cells. On the other hand, the delayed regulated lysis system should ensure *Salmonella* to release with adequate time a DNA vaccine vector in host tissues by programmed cell lysis, thereby enhancing the probability of efficient DNA delivery. Moreover, the improved DNA vaccine vector pYA4545 allows a rapid nuclear import and high-level synthesis of the encoded gene. Therefore, the potential of the improved RAS strain that could release TlpA and simultaneously release a DNA vaccine vector encoding death ligand Fas and/or TRAIL by the programmed cell lysis may be explored.

Constructing the Improved RAS Strain with Overexpression of the *Salmonella Enteritidis* tlpA Gene Directed by a *Salmonella* Promoter Preferentially Activated Inside of Tumors.

The promoter and Shine-Dalgarno (SD) sequence of the tlpA gene may be replaced with $P_{ansB}$ promoter and a strong SD sequence AGGA that should facilitate tumor-specific synthesis of TlpA, and subsequently induce apoptosis in tumor cells. The resulting strain may be Strain J (ΔasdA27:: TT araC $P_{BAD}$ c2 $\Delta P_{murA25}$::TT araC $P_{BAD}$ murA Δ(wza-wcaM)-8 ΔrelA 198::araC $P_{BAD}$ lacI TT Δ(araC $P_{BAD}$)-18:: P22 $P_R$ araBAD ΔpagP81::$P_{lpp}$ IpxE ΔendA2311 $\Delta P_{hilA}$:: $P_{trc}$ ΔlacO888 hilA ΔpurA $\Delta P_{tar}$::$P_{trc}$ ΔlacO888 tar $\Delta P_{tsr}$:: $P_{trc}$ ΔlacO888 tsr Δtrg or $\Delta P_{trg}$::rhaRS-$P_{rhaB}$ trg $\Delta P_{hilA}$:: $P_{trc}$ ΔlacO888 hilA ΔpurA $\Delta P_{sopE2}$::$P_{trc}$ sopE2 $\Delta P_{tlpA}$::$P_{ansB}$ tlpA). It is well established that cell proliferation and death are important in the regulation of development and homeostasis in multicellular organisms (44, 72), and physiological cell death is usually accomplished through apoptosis. However, uncontrolled growth and proliferation, and blocked apoptosis are major characteristics of cancer cells (144). The effects of RAS Strain H, I, and J harboring a DNA vaccine vector on cell proliferation and apoptosis in the tumor cell line, and the anti-tumor activity may be evaluated using the colon cancer mouse model.

Constructing an Improved RAS Strain Harboring the Improved DNA Vaccine Vector Encoding a Tumor-Specific Synthesized FasL to Trigger Tumor Cell Death.

The anti-tumor activity of FasL is well known. However, systemic administration of recombinant FasL appears to induce lethal liver injury (115), making the untargeted systemic delivery an unacceptable strategy. The use of tumor-selective promoters for targeted gene therapy of cancer depends on their strong and selective activities. Hexokinase type II (HK II) catalyzes the first committed step of glycolysis, which is over-expressed in tumors, and no longer responsive to normal physiological inhibitors, e.g., glucagon (89). The $P_{CMV}$ promoter of the improved DNA vaccine vector pYA4545 may be replaced with the HK II gene promoter to control the synthesis of Fas ligand. The resulting plasmid (pYA4545+PHK IIFasL) may be transformed into RAS Strain H, Strain I, and Strain J, respectively, to evaluate their anti-cancer efficacy. The synthesis of TlpA and FasL in normal cells (human Int-407 cells) and LS174T human colon cancer cell cultures may be compared. These RAS strain FasL delivery systems may be fully characterized as described in the Materials and Methods section. The $LD_{50}$ of each strain may be determined in BALB/c mice and their abilities of colonizating mouse Peyer's patches, spleen and liver monitored. The efficacy of these RAS strain FasL delivery systems to reduce tumor mass may be measured in LS174T/RFP tumor cells (human colon cancer cells, LS174T stably over expressing RFP), and in a real-time whole-body imaging of an orthotopic colon cancer model. The effectiveness of different *Salmonella* administration routes (including intratumoral injection, intravenous (i.v.) injection, intraperitoneal (I.P.) injection and oral administration) on the efficacy of these RAS strains may be specifically compared to reduce tumor mass. The most efficient administration route may be applied to future clinical tests. We have also constructed balanced-lethal vector harboring TRAIL encoding gene pYA5078 and Lysis vector specifying TRAIL encoding gene pYA5079. The vector pYA5079 was introduced into regulated delayed lysis system strain χ11204 (ΔasdA::TT araC $P_{BAD}$ c2 ΔmurA::TT araC $P_{BAD}$ murA Δ(gmd-fcl) ΔrelA::araC $P_{BAD}$ lacI TT Δpmi Δpmi ΔaraBAD ΔpurA) to test the effects of ΔpurA mutation on selective colonization in the necrotized tumor tissue. The vector pYA5078 will also be introduced into balanced-lethal host strain to test the effects of ΔpurA mutation.

Examination of Cancer Cell-Specific Expression of TlpA and FasL by Immunostaining and Microscopic Imaging.

Human Int-407 cells and human colon cancer LS174T cells may be infected with RAS Strain H (pYA4545), RAS strain H (pYA4545+PHK IIFasL), RAS strain I (pYA4545+ PHK IIFasL), and RAS strain J (pYA4545+PHK IIFasL), respectively. After incubating for a proper time, cells may be fixed with 2.0% paraformaldehyde and permeabilized with 0.5% Triton-X in PBS. The rabbit anti-TlpA or FasL antibody may be used as the primary antibodies, and detected by an Alexa-488-conjugated secondary antibody (Molecular Probes, Eugene, Oreg. USA). Infected cells may be counterstained by 4',6-diamino-2-phenylindole (DAPI), and mounted in Vectashield mounting medium (Vector Laboratories, Burlingame, Calif., USA). Microscopic images of cultured cells may be collected using an inverted microscope Leica Microsystems Heidelberg Gmbh.

Anti-Tumor Efficacy Assay in Cell Culture.

i. Cell Proliferation Assay.

Incorporation of bromodeoxyuridine (Brd-U) may be examined using a cell proliferation enzyme-linked immunosorbent assay (ELISA) kit (Roche Diagnostics, Mannheim, Germany) by following the manufacturer's instructions. Briefly, human Int-407 and LS174T cells may be plated at a density of 10-104 cells per well into 96-well tissue culture plates and allowed to adhere overnight. Cells may be infected with RAS Strain H (pYA4545), RAS Strain H (pYA4545+PHK IIFasL), Strain I (pYA4545+PHK IIFasL), and Strain J (pYA4545+PHK IIFasL), respectively, and may continue to be cultured for a proper time. The infected cells may be labeled with Brd-U for 8 h at the end of culture. Each condition may be measured in triplicate and the results may be analyzed by Student's t test.

ii. Apoptosis Assay.

Apoptosis may be characterized by a series of morphological changes such as chromatin condensation, cell shrinkage, membrane blebbing, packing of organelles, the formation of apoptotic bodies, internucleosomal DNA fragmentation (48, 145). The cleavage of DNA double strand can be visualized in a laddering pattern on agarose gel indicates a late event and is a hallmark of apoptosis (95). Therefore human Int-407 and LS174T cells may again be infected with the same RAS strains as described above. DNA fragmentation assays may be performed as described (130). The DNA solution may be electrophoresed on 2% agarose gel. DNA fragments may be visualized under UV light.

Iii. Measure Apoptosis/Pyroptosis Induction by Cell Morphology.

The LS174T/RFP cells may be grown on glass cover slips to about 60% confluency. Cells may be infected with the same RAS strains as described above. Afterwards, cells may be fixed with PBS-23.7% formaldehyde, and permeabilized with PBS-20.1% Triton X-100. Cells may be visualized using microscope Leica Microsystems Heidelberg Gmbh.

Anti-Tumor Efficacy Assay in Orthotopic Mouse Models.

i. Whole-Body Imaging of the Efficacy of the RAS Strains on the Growth of a Human Colorectal Tumor.

Whole-body imaging of orthotopic colorectal tumor-bearing mice (five mice/group) may be used for growth models and infection studies. Uninfected healthy mice and tumor-bearing mice may be the controls. For intratumoral injection, RAS Strain H (pYA4545), RAS Strain H (pYA4545+PHK IIFasL), Strain I (pYA4545+PHK IIFasL), and Strain J (pYA4545+PHK IIFasL), may be harvested at late logarithmic phase, respectively, washed, diluted with PBS, and injected directly into the central areas of the RFP-labeled tumors under fluorescence guidance. A total of 100 μl injection at two sites (50 μl each) and $10^9$ CFU per tumor may be used. For the i.v. injection, the same strains described above may be injected into the tail vein of RFP orthotopic tumor-bearing mice ($10^7$ CFU per 100 μl of PBS). For the I.P. injection, the same strains listed above may be injected into the peritoneum (body cavity) of RFP orthotopic tumor-bearing mice ($10^5$ CFU per 100 μl of PBS). For oral administration, tumor-bearing mice may be deprived of food and water 4 h before oral infection. The above strains may be inoculated orally ($10^9$ CFU per 20 μl of PBS). Food and water may be returned 30 min after infection. Whole-body fluorescence imaging techniques May be used to track the effect on the red fluorescent protein (RFP)-labeled target tumors using the Lumina Imaging System IVIS-200 (Xenogen) by following instructions of the manufacturer. Tumor size may be determined by fluorescence imaging on days 11, 16, 21, 25, 30 and 35.

ii. Demonstrate Apoptotic Cell Death of Tumor Tissues.

Mice may be killed on Day 36 after inoculation of the RAS strains. Specimens from the tumor tissues may be collected, fixed in 10% neutral formaldehyde for 6 h and paraffin-embedded, and 5 μm-thick consecutive sections may be sliced. To demonstrate apoptotic cell death of tumor tissues on paraffin-embedded sections, terminal deoxynucleotidyl transferase-mediated dUTP nick end labeling (TUNEL) assay may be performed using In Situ Cell Death Detection Kit (Roche Diagnostics, Basel, Switzerland) according to the manufacturer's instructions. Positive index (PI) may be counted from five randomly selected high-power fields under light microscope, and expressed as a percentage of total cells counted.

Discussion.

(i) If the activity of $P_{ansB}$ promoter is not high enough to trigger expected high-level expression of the bacterial virulence factor genes in tumor cells, $P_{ansB}$ promoter may be engineered by modifying its −35 and −10 regions. The codons of the tlpA gene may be further optimized for high-level expression in *Salmonella*.

(ii) On the other hand, the plasmid stability of the DNA vaccine vector in *Salmonella* during infection and the timing of *Salmonella* cell lysis to release DNA vaccine vector are critical for desired anti-tumor efficacy. If needed, the improved regulated delayed lysis vector pYA4545 (pUC ori) derivatives may be constructed. These vectors may have pSC101 ori, p15A ori and pBR ori, respectively, such that plasmid stability during *Salmonella* infection and the timing of lysis in vivo for release of DNA vaccine vectors may be improved.

The success of using a multiple functional RAS host-vector delivery system to overcome therapeutic resistance and increase treatment efficiency may significantly reduce systemic toxicity, limit the deleterious effects of metastatic disease, and increase life expectancy. Future human trials using similarly genetically modified *S. Typhi* strains may demonstrate the ability of administration of the multiple functional RAS host-vector anti-cancer system to reduce local recurrence and metastatic disease in stage-four colorectal cancer patients.

REFERENCES FOR EXAMPLES 1-8

1. Adler, J., and B. Templeton. 1967. The effect of environmental conditions on the motility of *Escherichia coli*. J Gen Microbiol 46:175-184.
2. Agrawal, N., C. Bettegowda, I. Cheong, J. F. Geschwind, C. G. Drake, E. L. Hipkiss, M. Tatsumi, L. H. Dang, L. A. Diaz, Jr., M. Pomper, M. Abusedera, R. L. Wahl, K. W. Kinzler, S. Zhou, D. L. Huso, and B. Vogelstein. 2004. Bacteriolytic therapy can generate a potent immune response against experimental tumors. Proc Natl Acad Sci USA 101:15172-15177.
3. Akira, S., S. Uematsu, and O. Takeuchi. 2006. Pathogen recognition and innate immunity. Cell 124:783-801.
4. Alba, B. M., H. J. Zhong, J. C. Pelayo, and C. A. Gross. 2001. degS (hhoB) is an essential *Escherichia coli* gene whose indispensable function is to provide sigma (E) activity. Mol. Microbiol. 40:1323-1333.
5. Alderson, M. R., P. McGowan, J. R. Baldridge, and P. Probst. 2006. TLR4 agonists as immunomodulatory agents. J Endotoxin Res 12:313-319.
6. Arrach, N., M. Zhao, S. Porwollik, R. M. Hoffman, and M. McClelland. 2008. *Salmonella* promoters preferentially activated inside tumors. Cancer Res 68:4827-4832.
7. Avogadri, F., C. Martinoli, L. Petrovska, C. Chiodoni, P. Transidico, V. Bronte, R. Longhi, M. P. Colombo, G. Dougan, and M. Rescigno. 2005. Cancer immunotherapy based on killing of *Salmonella*-infected tumor cells. Cancer Res 65:3920-3927.
8. Baek, C. H., S. Wang, K. L. Roland, and R. Curtiss, III. 2009. Leucine-responsive regulatory protein (Lrp) acts as a virulence repressor in *Salmonella enterica* serovar *Typhimurium*. J. Bacteriol. 191:1278-1292.
9. Bajaj, V., C. Hwang, C. A. Lee. 1995. hilA is a novel ompR/toxR family member that activates the expression of *Salmonella typhimurium* invasion genes. Mol. Microbiol. 18:715-727.
10. Bajaj, V., R. L. Lucas, C. Hwang, and C. A. Lee. 1996. Co-ordinate regulation of *Salmonella typhimurium* invasion genes by environmental and regulatory factors is mediated by control of hilA expression. Mol. Microbiol. 22:703-714.

11. Barton, G. M. 2008. A calculated response: control of inflammation by the innate immune system. J Clin Invest 118:413-420.
12. Black, R. E., S. S. Morris, and J. Bryce. 2003. Where and why are 10 million children dying every year? Lancet 361:2226-2234.
13. Black, S., and N. G. Wright. 1955. Aspartic beta-semialdehyde dehydrogenase and aspartic betasemialdehyde. J. Biol. Chem. 213:39-50.
14. Blat, Y., and M. Eisenbach. 1995. Tar-dependent and -independent pattern formation by *Salmonella typhimurium*. J Bacteriol 177:1683-1691.
15. Blattman, J. N., and P. D. Greenberg. 2004. Cancer immunotherapy: a treatment for the masses. Science 305: 200-205.
16. Bren, A., and M. Eisenbach. 2000. How signals are heard during bacterial chemotaxis: protein-protein interactions in sensory signal propagation. J Bacteriol 182:6865-6873.
17. Brennan, M. A., and B. T. Cookson. 2000. *Salmonella* induces macrophage death by caspase-1-dependent necrosis. Mol. Microbiol. 38:31-40.
18. Brown, E. D., E. I. Vivas, C. T. Walsh, and R. Kolter. 1995. MurA (MurZ), the enzyme that catalyzes the first committed step in peptidoglycan biosynthesis, is essential in *Escherichia coli*. J Bacteriol 177:4194-4197.
19. Brunner, S., T. Sauer, S. Carotta, M. Cotten, M. Saltik, and E. Wagner. 2000. Cell cycle dependence of gene transfer by lipoplex, polyplex and recombinant adenovirus. Gene Ther. 7:401-407.
20. Bruno, V. M., S. Hannemann, M. Lara-Tejero, R. A. Flavell, S. H. Kleinstein, and J. E. Galan. 2009. *Salmonella Typhimurium* type III secretion effectors stimulate innate immune responses in cultured epithelial cells. PLoS Pathog 5:e1000538.
21. Capecchi, M. R. 1980. High efficiency transformation by direct microinjection of DNA into cultured mammalian cells. Cell 22:479-488.
22. Cardenas, L., and J. D. Clements. 1992. Oral immunization using live attenuated *Salmonella* spp. as carriers of foreign antigens. Clin. Microbiol. Rev. 5:328-342.
23. Carey R. W., H. J. F., Whang H. Y., Netter E. and Bryant B. 1967. Clostridial oncolysis in man. Eur. J. Cancer 3:37-46.
24. Carswell, S., and J. C. Alwine. 1989. Efficiency of utilization of the simian virus 40 late polyadenylation site: effects of upstream sequences. Mol. Cell. Biol. 9:4248-4258.
25. Chatfield, S, N., I. G. Charles, A. J. Makoff, M. D. Oxer, G. Dougan, D. Pickard, D. Slater, and N. F. Fairweather. 1992. Use of the nirB promoter to direct the stable expression of heterologous antigens in *Salmonella* oral vaccine strains: development of a single-dose oral tetanus vaccine. Biotechnology 10:888-892.
26. Chen, L. M., S. Hobbie, and J. E. Galan. 1996. Requirement of CDC42 for *Salmonella*-induced cytoskeletal and nuclear responses. Science 274:2115-2118.
27. Chen, L. M., K. Kaniga, and J. E. Galan. 1996. *Salmonella* spp. are cytotoxic for cultured macrophages. Mol. Microbiol. 21:1101-1115.
28. Clairmont, C., K. C. Lee, J. Pike, M. lttensohn, K. B. Low, J. Pawelek, D. Bermudes, S. M. Brecher, D. Margitich, J. Turnier, Z. Li, X. Luo, I. King, and L. M. Zheng. 2000. Biodistribution and genetic stability of the novel antitumor agent VNP20009, a genetically modified strain of *Salmonella typhimurium*. J Infect Dis 181:1996-2002.
29. Coley, W. B. 1991. The treatment of malignant tumors by repeated inoculations of erysipelas. With a report of ten original cases. 1893. Clin Orthop Relat Res:3-11.
30. Curtiss, R., III. 2005. Antigen delivery systems: development of live recombinant attenuated bacterial antigen and DNA vaccine delivery vector vaccines, p. 1009-1037. In J. Mestecky, M. E. Lamm, W. Strober, J. Bienenstock, J. R. McGhee, and L. Mayer (ed.), Mucosal Immunology, 3rd edition, vol. 1. Academic Press, San Diego.
31. Curtiss, R., III, T. Doggett, A. Nayak, and J. Srinivasan. 1996. Strategies for the use of live recombinant avirulent bacterial vaccines for mucosal immunization, p. 499-511. In H. Kiyono and M. F. Kagnoff (ed.), Essentials of Mucosal Immunology. Academic Press, San Diego.
32. Curtiss, R., III, J. E. Galan, K. Nakayama, and S. M. Kelly. 1990. Stabilization of recombinant avirulent vaccine strains in vivo. Res. Microbiol. 141:797-805.
33. Curtiss, R., III, D. A. Pereira, J. C. Hsu, S. C. Hull, J. E. Clark, L. J. Maturin, III, R. Goldschmidt, R. Moody, M. Inoue, and L. Alexander. 1976. Biological containment: The subordination of *Escherichia coli* K-12, p. 45-56. In R. F. Beers Jr. and E. G. Bassett (ed.), Recombinant Molecules: Impact on Science and Society. Raven Press, N. Y.
34. Curtiss, R., III, S. Y. Wanda, B. M. Gunn, X. Zhang, S. A. Tinge, V. Ananthnarayan, H. Mo, S. Wang, and W. Kong. 2009. *Salmonella enterica* serovar *typhimurium* strains with regulated delayed attenuation in vivo. Infect. Immun. 77:1071-1082.
35. Curtiss, R., III, S. B. Porter, M. Munson, S. A. Tinge, J. O. Hassan, C. Gentry-Weeks, and S. M. Kelly. 1991. Nonrecombinant and recombinant avirulent *Salmonella* live vaccines for poultry, p. 169-198. Colonization Control of Human Bacterial Enteropathogens in Poultry. Academic Press, Inc., New York.
36. Daigle, F., J. E. Graham, and R. Curtiss III. 2001. Identification of *Salmonella typhi* genes expressed within macrophages by selective capture of transcribed sequences (SCOTS). Mol. Microbiol. 41:1211-1222.
37. Davison, J. E. 2002. Towards safer vectors for the field release of recombinant bacteria. Biosafety Res. 1:9-18.
38. De Groote, M. A., T. Testerman, Y. Xu, G. Stauffer and F. C. Fang. 1996. Homocysteine antagonism of nitric oxide-related cytostasis in *Salmonella typhimurium*. Science 272:414-417.
39. Dean, D. A. 1997. Import of plasmid DNA into the nucleus is sequence specific. Exp. Cell Res. 230:293-302.
40. Dean, D. A., B. S. Dean, S. Muller, and L. C. Smith. 1999. Sequence requirements for plasmid nuclear import. Exp. Cell Res. 253:713-722.
41. Dubnau, D. 1999. DNA uptake in bacteria. Annu. Rev. Microbiol. 53:217-244.
42. Dunstan, S. J., C. P. Simmons, and R. A. Strugnell. 1998. Comparison of the abilities of different attenuated *Salmonella typhimurium* strains to elicit humoral immune responses against a heterologous antigen. Infect Immun 66:732-740.
43. Fahlen, T. F., R. L. Wilson, J. D. Boddicker, and B. D. Jones. 2001. Hha is a negative modulator of transcription of hilA, the *Salmonella enterica* serovar *Typhimurium* invasion gene transcriptional activator. J. Bacteriol. 183: 6620-6629.
44. Farber, E. 1994. Programmed cell death: necrosis versus apoptosis. Mod Pathol 7:605-609.

45. Fink, S. L., and B. T. Cookson. 2006. Caspase-1-dependent pore formation during pyroptosis leads to osmotic lysis of infected host macrophages. Cell. Microbiol. 8:1812-1825.

46. Fink, S. L., and B. T. Cookson. 2007. Pyroptosis and host cell death responses during *Salmonella* infection. Cell Microbiol 9:2562-2570.

47. Fiorentini, C., L. Falzano, S. Travaglione, and A. Fabbri. 2003. Hijacking Rho GTPases by protein toxins and apoptosis: molecular strategies of pathogenic bacteria. Cell Death Differ 10:147-152.

48. Fleisher, T. A. 1997. Apoptosis. Ann Allergy Asthma Immunol 78:245-249; quiz 249-250.

49. Forbes, N. S., L. L. Munn, D. Fukumura, and R. K. Jain. 2003. Sparse initial entrapment of systemically injected *Salmonella typhimurium* leads to heterogeneous accumulation within tumors. Cancer Res 63:5188-5193.

50. Francis, C. L., T. A. Ryan, B. D. Jones, S. J. Smith, and S. Falkow. 1993. Ruffles induced by *Salmonella* and other stimuli direct macropinocytosis of bacteria. Nature 364:639-642.

51. Friebel, A., H. Ilchmann, M. Aepfelbacher, K. Ehrbar, W. Machleidt, and W. D. Hardt. 2001. SopE and SopE2 from *Salmonella typhimurium* activate different sets of RhoGTPases of the host cell. J Biol Chem 276:34035-34040.

52. Fu, G. F., X. Li, Y. Y. Hou, Y. R. Fan, W. H. Liu, and G. X. Xu. 2005. *Bifidobacterium longum* as an oral delivery system of endostatin for gene therapy on solid liver cancer. Cancer Gene Ther 12:133-140.

53. Gal-Mor, O., Y. Valdez, and B. B. Finlay. 2006. The temperature-sensing protein TlpA is repressed by PhoP and dispensable for virulence of *Salmonella enterica* serovar Typhimurium in mice. Microbes Infect. 8:2154-2162.

54. Galan, J. E., and R. Curtiss III. 1989. Cloning and molecular characterization of genes whose products allow *Salmonella typhimurium* to penetrate tissue culture cells. Proc. Natl. Acad. Sci. USA 86:6383-6387.

55. Galan, J. E., K. Nakayama, and R. Curtiss III. 1990. Cloning and characterization of the asd gene of *Salmonella typhimurium*: use in stable maintenance of recombinant plasmids in *Salmonella* vaccine strains. Gene 94:29-35.

56. Galen, J. E., J. Nair, J. Y. Wang, S. S. Wasserman, M. K. Tanner, M. B. Sztein, and M. M. Levine. 1999. Optimization of plasmid maintenance in the attenuated live vector vaccine strain *Salmonella typhi* CVD 908-htrA. Infect. Immun. 67:6424-6433.

57. Garmory, H. S. et. al. 2005. Antibiotic-free plasmid stabilization by operator-repressor titration for vaccine delivery by using live *Salmonella enterica* serovar *Typhimurium*. Infect. Immun. 73:2005-2011.

58. Ghosh, S., M. J. May, and E. B. Kopp. 1998. NF-kappa B and Rel proteins: evolutionarily conserved mediators of immune responses. Annu Rev Immunol 16:225-260.

59. Giaccia, A. J. 1996. Hypoxic Stress Proteins: Survival of the Fittest. Semin Radiat Oncol 6:46-58.

60. Guzman, L. M., D. Belin, M. J. Carson, and J. Beckwith. 1995. Tight regulation, modulation, and high-level expression by vectors containing the arabinose $P_{BAD}$ promoter. J. Bacteriol. 177:4121-4130.

61. Hardt, W. D., L. M. Chen, K. E. Schuebel, X. R. Bustelo, and J. E. Galan. 1998. *S. typhimurium* encodes an activator of Rho GTPases that induces membrane ruffling and nuclear responses in host cells. Cell 93:815-826.

62. Heijstek, M. W., O. Kranenburg, and I. H. Borel Rinkes. 2005. Mouse models of colorectal cancer and liver metastases. Dig Surg 22:16-25.

63. Hersh, D., D. M. Monack, M. R. Smith, N. Ghori, S. Falkow, and A. Zychlinsky. 1999. The *Salmonella* invasin SipB induces macrophage apoptosis by binding to caspase-1. Proc Natl Acad Sci USA 96:2396-2401.

64. Hitchcock, P. J., and T. M. Brown. 1983. Morphological heterogeneity among *Salmonella* lipopolysaccharide chemotypes in silver-stained polyacrylamide gels. J. Bacteriol. 154:269-277.

65. Huber, B. E., C. A. Richards, and T. A. Krenitsky. 1991. Retroviral-mediated gene therapy for the treatment of hepatocellular carcinoma: an innovative approach for cancer therapy. Proc Natl Acad Sci USA 88:8039-8043.

66. Iwama, T., K. I. Nakao, H. Nakazato, S. Yamagata, M. Homma, and I. Kawagishi. 2000. Mutational analysis of ligand recognition by tcp, the citrate chemoreceptor of *Salmonella enterica* serovar *typhimurium*. J Bacteriol 182:1437-1441.

67. Jain, R. K., and N. S. Forbes. 2001. Can engineered bacteria help control cancer? Proc Natl Acad Sci USA 98:14748-14750.

68. Jennings, M. P., S. P. Scott, and I. R. Beacham. 1993. Regulation of the ansB gene of *Salmonella enterica*. Mol Microbiol 9:165-172.

69. Jepson, M. A., and M. A. Clark. 2001 The role of M cells in *Salmonella* infection. Microbes Infect. 3:1183-1190.

70. Jesenberger, V., K. J. Procyk, J. Yuan, S. Reipert, and M. Baccarini. 2000. *Salmonella*-induced caspase-2 activation in macrophages: a novel mechanism in pathogen-mediated apoptosis. J. Exp. Med. 192:1035-1046.

71. Jones, B. D., N. Ghori, S. Falkow. 1994 *Salmonella typhimurium* initiates murine infection by penetrating and destroying the specialized epithelial M cells of the Peyer's patches. J Exp Med. 180:15-23.

72. Kanduc, D., A. Mittelman, R. Serpico, E. Sinigaglia, A. A. Sinha, C. Natale, R. Santacroce, M. G. Di Corcia, A. Lucchese, L. Dini, P. Pani, S. Santacroce, S. Simone, R. Bucci, and E. Farber. 2002. Cell death: apoptosis versus necrosis (review). Int J Oncol 21:165-170.

73. Kang, H. Y., D. M. Dozois, S. A. Tinge, T. H. Lee, and R. Curtiss, III. 2002. Transduction-mediated transfer of unmarked deletion and point mutations through use of counterselectable suicide vectors. J. Bacteriol. 184:307-312.

74. Kang, H. Y., T. H. Lee, X. Zhang, and R. Curtiss III. ABSTRACT. 2002. Presented at the Abstracts of the 102th General meeting of American Society for Microbiology, Washington, D.C.

75. Kari, T. I. a. C. 1980. Accumulation of ppGpp in a relA mutant of *Escherichia coli* during amino acid starvation. J. Biol. Chem. 255:3838-3840.

76. Karin, M., T. Lawrence, and V. Nizet. 2006. Innate immunity gone awry: linking microbial infections to chronic inflammation and cancer. Cell 124:823-835.

77. Kasinskas, R. W., and N. S. Forbes. 2007. *Salmonella typhimurium* lacking ribose chemoreceptors localize in tumor quiescence and induce apoptosis. Cancer Res 67:3201-3209.

78. Kasinskas, R. W., and N. S. Forbes. 2006. *Salmonella typhimurium* specifically chemotax and proliferate in heterogenous tumor tissue in vitro. Biotechnol Bioeng 94:710-721.

79. Khan, A. Q., L. Zhao, K. Hirose, M. Miyake, T. Li, Y. Hashimoto, Y. Kawamura, and T. Ezaki. 1998. *Salmonella typhi* rpoS mutant is less cytotoxic than the parent strain 79. but survives inside resting THP-1 macrophages. FEMS Microbiol. Lett. 161:201-208.
80. Kim, J. J., and I. F. Tannock. 2005. Repopulation of cancer cells during therapy: an important cause of treatment failure. Nat Rev Cancer 5:516-525.
81. Kobaek-Larsen, M., I. Thorup, A. Diederichsen, C. Fenger, and M. R. Hoiting a. 2000. Review of colorectal cancer and its metastases in rodent models: comparative aspects with those in humans. Comp Med 50:16-26.
82. Kong, W., S. Y. Wanda, X. Zhang, W. Bollen, S. A. Tinge, K. L. Roland, and R. Curtiss III. 2008. Regulated programmed lysis of recombinant *Salmonella* in host tissues to release protective antigens and confer biological containment. Proc. Natl. Acad. Sci. USA 105:9361-9366.
83. Koski P, H. S., S. Sukupolyi, S. Taira, P. Riikonen, K. Osterlund, R. Hurme, and M. Rhen. 1992. A new alpha-helical coiled coil protein encoded by the *Salmonella typhimurium* virulence plasmid. J Biol. Chem. 267: 12258-12265.
84. Kotton, C. N., and E. L. Hohmann. 2004. Enteric pathogens as vaccine vectors for foreign antigen delivery. Infect. I m mu n. 72:5535-5547.
85. Kouraklis, G. P. 2003. Gene therapy for cancer: current status and prospects. Dig Dis Sci 48:854-855.
86. Latham, J. P., P. F. Searle, V. Mautner, and N. D. James. 2000. Prostate-specific antigen promoter/enhancer driven gene therapy for prostate cancer: construction and testing of a tissue-specific adenovirus vector. Cancer Res 60:334-341.
87. Lee, C. H., C. L. Wu, and A. L. Shiau. 2004. Endostatin gene therapy delivered by *Salmonella choleraesuis* in murine tumor models. Gene Med 6:1382-1393.
88. Lee, C. H., C. L. Wu, and A. L. Shiau. 2005. Systemic administration of attenuated *Salmonella choleraesuis* carrying thrombospondin-1 gene leads to tumor-specific transgene expression, delayed tumor growth and prolonged survival in the murine melanoma model. Cancer Gene Ther 12:175-184.
89. Lee, H. S., S. B. Cho, H. E. Lee, M. A. Kim, J. H. Kim, J. Park do, H. K. Yang, B. L. Lee, and W. H. Kim. 2007. Protein expression profiling and molecular classification of gastric cancer by the tissue array method. Clin Cancer Res 13:4154-4163.
90. Li, Y., S. Wang, G. Scarpellini, B. Gunn, W. Xin, S. Y. Wanda, K. L. Roland, and R. Curtiss, III. 2009. Evaluation of new generation *Salmonella enterica* serovar *Typhimurium* vaccines with regulated delayed attenuation to induce immune responses against PspA. Proc Natl Acad Sci USA. 106:593-598.
91. Low, K. B., M. lttensohn, T. Le, J. Platt, S. Sodi, M. Amoss, O. Ash, E. Carmichael, A. Chakraborty, J. Fischer, S. L. Lin, X. Luo, S. I. Miller, L. Zheng, I. King, J. M. Pawelek, and D. Bermudes. 1999. Lipid A mutant *Salmonella* with suppressed virulence and TNF-a induction retain tumor-targeting in vivo. Nat. Biotechnol. 17:37-41.
92. Lucas, R. L., C. P. Lostroh, C. C. DiRusso, M. P. Spector, B. L. Wanner, and C. A. Lee. 2000 Multiple factors independently regulate hilA and invasion gene expression in *Salmonella enterica* serovar *typhimurium*. J. Bacteriol. 182:1872-1882.
93. Lundberg, U., U. Vinatzer, D. Berdnik, A. von Gabain, and M. Baccarini. 1999. Growth phase-regulated induction of *Salmonella*-induced macrophage apoptosis correlates with transient expression of SPI-1 genes. J. Bacteriol. 181:3433-3437.
94. Luria, S. E., and J. W. Burrous. 1957. Hybridization between *Escherichia coli* and *Shigella*. J. Bacteriol. 74:461-476.
95. Magalska, A., A. Brzezinska, A. Bielak-Zmijewska, K. Piwocka, G. Mosieniak, and E. Sikora. 2006. Curcumin induces cell death without oligonucleosomal DNA fragmentation in quiescent and proliferating human CD8+ cells. Acta Biochim Pol 53:531-538.
96. Malmgren, R. A., and C. C. Flanigan. 1955. Localization of the vegetative form of *Clostridium tetani* in mouse tumors following intravenous spore administration. Cancer Res 15:473-478.
97. Mariathasan, S., K. Newton, D. M. Monack, D. Vucic, D. M. French, W. P. Lee, M. Roose-Girma, S. Erickson, and V. M. Dixit. 2004. Differential activation of the inflammasome by caspase-1 adaptors ASC and lpaf. Nature 430:213-218.
98. Marincola, F. M., E. M. Jaffee, D. J. Hicklin, and S. Ferrone. 2000. Escape of human solid tumors from T-cell recognition: molecular mechanisms and functional significance. Adv Immunol 74:181-273.
99. Mazumder, R., T. J. Phelps, N. R. Krieg, and R. E. Benoit. 1999. Determining chemotactic responses by two subsurface microaerophiles using a simplified capillary assay method. J Microbiol Methods 37:255-263.
100. Medina, E., and C. A. Guzman. 2001. Use of live bacterial vaccine vectors for antigen delivery: potential and limitations. Vaccine 19:1573-1580.
101. Mesibov, R., G. W. Ordal, and J. Adler. 1973. The range of attractant concentrations for bacterial chemotaxis and the threshold and size of response over this range. Weber law and related phenomena. J Gen Physiol 62:203-223.
102. Miao, E. A., C. M. Alpuche-Aranda, M. Dors, A. E. Clark, M. W. Bader, S. I. Miller, and A. Aderem. 2006. Cytoplasmic flagellin activates caspase-1 and secretion of interleukin 10 via loaf. Nat. Immunol. 7:569-575.
103. Michl, P., and T. M. Gress. 2004. Bacteria and bacterial toxins as therapeutic agents for solid tumors. Curr Cancer Drug Targets 4:689-702.
104. Miller, V. L., and J. J. Mekalanos. 1988. A novel suicide vector and its use in construction of insertion mutations: osmoregulation of outer membrane proteins and virulence determinants in *Vibrio cholerae* requires toxR. J. Bacteriol. 170:2575-2583.
105. Minchinton, A. I., and I. F. Tannock. 2006. Drug penetration in solid tumours. Nat Rev Cancer 6:583-592.
106. Minton, N. P. 2003. *Clostridia* in cancer therapy. Nat Rev Microbiol 1:237-242.
107. Mirzayans, R., R. A. Aubin, and M. C. Paterson. 1992. Differential expression and stability of foreign genes introduced into human fibroblasts by nuclear versus cytoplasmic microinjection. Mutat. Res. 281:115-122.
108. Monack, D. M., B. Raupach, A. E. Hromockyj, and S. Falkow. 1996. *Salmonella typhimurium* invasion induces apoptosis in infected macrophages. Proc. Natl. Acad. Sci. USA 93:9833-9838.
109. Nakayama, K., S. M. Kelly, and R. Curtiss III. 1988. Construction of an Asd+ expression-cloning vector: stable maintenance and high level expression of cloned genes in a *Salmonella* vaccine strain. Bio/Tech 6:693-697.
110. Nemunaitis, J., C. Cunningham, N. Senzer, J. Kuhn, J. Cramm, C. Litz, R. Cavagnolo, A. Cahill, C. Clairmont, and M. Sznol. 2003. Pilot trial of genetically modified, attenuated *Salmonella* expressing the *E. coli* cytosine deaminase gene in refractory cancer patients. Cancer Gene Ther 10:737-744.

111. Newman, R. M., P. Salunkhe, A. Godzik, J. C. Reed. 2006. Identification and characterization of a novel bacterial virulence factor that shares homology with mammalian Toll/interleukin-1 receptor family proteins. Infect Immun. 74:594-601.

112. Patel, J. C., and J. E. Galan. 2006. Differential activation and function of Rho GTPases during *Salmonella*-host cell interactions. J Cell Biol 175:453-463.

113. Pawelek, J. M., K. B. Low, and D. Bermudes. 1997. Tumor-targeted *Salmonella* as a novel anticancer vector. Cancer Res 57:4537-4544.

114. Poltorak, A., X. He, I. Smirnova, M. Y. Liu, C. Van Huffel, X. Du, D. Birdwell, E. Alejos, M. Silva, C. Galanos, M. Freudenberg, P. Ricciardi-Castagnoli, B. Layton, and B. Beutler. 1998. Defective LPS signaling in C3H/HeJ and C57BL/10ScCr mice: mutations in Tlr4 gene. Science 282:2085-2088.

115. Rensing-Ehl, A., K. Frei, R. Flury, B. Matiba, S. M. Mariani, M. Weller, P. Aebischer, P. H. Krammer, and A. Fontana. 1995. Local Fas/APO-1 (CD95) ligand-mediated tumor cell killing in vivo. Eur J Immunol 25:2253-2258.

116. Rescigno, M., V. Piguet, B. Valzasina, S. Lens, R. Zubler, L. French, V. Kindler, J. Tschopp, and P. Ricciardi-Castagnoli. 2000. Fas engagement induces the maturation of dendritic cells (DCs), the release of interleukin (IL)-1 beta, and the production of interferon gamma in the absence of IL-12 during DC-T cell cognate interaction: a new role for Fas ligand in inflammatory responses. Exp Med 192:1661-1668.

117. Ribeiro, S. C., G. A. Monteiro, and D. M. Prazeres. 2004. The role of polyadenylation signal secondary structures on the resistance of plasmid vectors to nucleases. J. Gene. Med. 6:565-573.

118. Roland, K., R. Curtiss, III, and D. Sizemore. 1999. Construction and evaluation of a Acya Acrp *Salmonella typhimurium* strain expressing avian pathogenic *Escherichia coli* 078 LPS as a vaccine to prevent airsacculitis in chickens. Avian Dis. 43:429-441.

119. Roth, J. A., and R. J. Cristiano. 1997. Gene therapy for cancer: what have we done and where are we going? J Natl Cancer Inst 89:21-39.

120. Saltzman, D. A. 2005. Cancer immunotherapy based on the killing of *Salmonella typhimurium*-infected tumour cells. Expert Opin Biol Ther 5:443-449.

121. Sambrook, J., E. F. Fritsch, and T. Maniatis. 1989. Molecular cloning: a laboratory manual, 2nd ed. Cold Spring Harbor Laboratory Press, Plainview, N.Y.

122. Sanders, D. A., B. Mendez, and D. E. Koshland, Jr. 1989. Role of the CheW protein in bacterial chemotaxis: overexpression is equivalent to absence. J Bacteriol 171:6271-6278.

123. Schmieger, H.1972. Phage P22-mutants with increased or decreased transduction abilities. Mol. Gen. Genet. 119:75-88.

124. Schmieger, H., and H. Backhaus. 1976. Altered cotransduction frequencies exhibited by HT-mutants of *Salmonella*-phage P22. Mol. Gen. Genet. 143:307-309.

125. Schodel, F., S. M. Kelly, D. Peterson, D. Milich, J. Hughes, S. Tinge, R. Wirtz, and R. Curtiss III. 1994. Development of recombinant Salmonellae expressing hybrid hepatitis B virus core particles as candidate oral vaccines. Dev. Biol. Stand. 82:151-158.

126. Shankaran, V., H. Ikeda, A. T. Bruce, J. M. White, P. E. Swanson, L. J. Old, and R. D. Schreiber. 2001. IFNgamma and lymphocytes prevent primary tumour development and shape tumour immunogenicity. Nature 410:1107-1111.

127. Sun, W., S. Wang, and R. Curtiss III. 2008. Highly efficient method for introducing successive multiple scarless gene deletions and markerless gene insertions into the *Yersinia pestis* chromosome. Appl. Environ. Microbiol. 74:4241-4245.

128. Takeuchi, A. 1967. Electron microscope studies of experimental *Salmonella* infection. I. Penetration into the intestinal epithelium by *Salmonella typhimurium*. Am J Pathol 50:109-136.

129. Tallant, T., A. Deb, N. Kar, J. Lupica, M. J. de Veer, and J. A. DiDonato. 2004. Flagellin acting via TLR5 is the major activator of key signaling pathways leading to NF-kappa B and proinflammatory gene program activation in intestinal epithelial cells. BMC Microbiol. 4:1471-2180.

130. Tansuwanwong, S., Y. Hiroyuki, I. Kohzoh, and U. Vinitketkumnuen. 2006. Induction of apoptosis in RKO colon cancer cell line by an aqueous extract of Millingtonia hortensis. Asian Pac J Cancer Prev 7:641-644.

131. Theys, J., S. Barbe, W. Landuyt, S, Nuyts, L. Van Mellaert, B. Wouters, J. Anne, and P. Lambin. 2003. Tumor-specific gene delivery using genetically engineered bacteria. Curr Gene Ther 3:207-221.

132. Thorburn, A. 2004. Death receptor-induced cell killing. Cell Signal 16:139-144. 133. Toso, J. F., V. J. Gill, P. Hwu, F. M. Marincola, N. P. Restifo, D. J. Schwartzentruber, R. M. Sherry, S. L. Topalian, J. C. Yang, F. Stock, L. J. Freezer, K. E. Morton, C. Seipp, L. Haworth, S. Mavroukakis, D. White, S. MacDonald, J. Mao, M. Sznol, and S. A. Rosenberg. 2002. Phase I study of the intravenous administration of attenuated *Salmonella typhimurium* to patients with metastatic melanoma. J Clin Oncol 20:142-152.

134. Tseng, W., X. Leong, and E. Engleman. 2007. Orthotopic mouse model of colorectal cancer. J V is Exp: 484.

135. Vacik, J., B. S. Dean, W. E. Zimmer, and D. A. Dean. 1999. Cell-specific nuclear import of plasmid DNA. Gene Ther. 6:1006-1014.

136. Valentine, P. J., B. P. Devore, and F. Heffron. 1998. Identification of three highly attenuated *Salmonella typhimurium* mutants that are more immunogenic and protective in mice than a prototypical aroA mutant. Infect Immun 66:3378-3383.

137. Vassaux, G., J. Nitcheu, S. Jezzard, and N. R. Lemoine. 2006. Bacterial gene therapy strategies. J Pathol 208:290-298.

138. Vile, R. G., and I. R. Hart. 1993. Use of tissue-specific expression of the herpes simplex virus thymidine kinase gene to inhibit growth of established murine melanomas following direct intratumoral injection of DNA. Cancer Res 53:3860-3864.

139. Vitiello M, D. I. M., Galdiero M, Raieta K, Tortora A, Rotondo P, Peluso L, Galdiero M. 2004 Interleukin-8 production by THP-1 cells stimulated by *Salmonella enterica* serovar *Typhimurium porins* is mediated by AP-1, NF-kappaB and MAPK pathways. Cytokine 27:15-24.

140. Vojtek, A. B., and J. A. Cooper. 1995. Rho family members: activators of MAP kinase cascades. Cell 82:527-529.

141. Whitfield, C. 2006. Biosynthesis and assembly of capsular polysaccharides in *Escherichia coli*. Annu Rev Biochem 75:39-68.

142. Wilmanns, C., D. Fan, C. A. O'Brian, C. D. Bucana, and I. J. Fidler. 1992. Orthotopic and ectopic organ environments differentially influence the sensitivity of murine colon carcinoma cells to doxorubicin and 5-fluorouracil. Int J Cancer 52:98-104.

143. Yamamoto, K., and Y. Imae. 1993. Cloning and characterization of the *Salmonella typhimurium* specific chemoreceptor Tcp for taxis to citrate and from phenol. Proc Natl Acad Sci USA 90:217-221.

144. Yuan, S. L., Y. Q. Wei, X. J. Wang, F. Xiao, S. F. Li, and J. Zhang. 2004. Growth inhibition and apoptosis induction of tanshinone II-A on human hepatocellular carcinoma cells. World J Gastroenterol 10:2024-2028.

145. Zhang, J. H., and M. Xu. 2000. DNA fragmentation in apoptosis. Cell Res 10:205-211.

146. Zhao, M., M. Yang, X. M. Li, P. Jiang, E. Baranov, S. Li, M. Xu, S. Penman, and R. M. Hoffman. 2005. Tumor-targeting bacterial therapy with amino acid auxotrophs of GFP-expressing *Salmonella typhimurium*. Proc Natl Acad Sci USA 102:755-760.

147. Zhao, M., M. Yang, H. Ma, X. Li, X. Tan, S. Li, Z. Yang, and R. M. Hoffman. 2006. Targeted therapy with a *Salmonella typhimurium* leucine-arginine auxotroph cures orthotopic human breast tumors in nude mice. Cancer Res 66:7647-7652.

148. Zhou, D., L. M. Chen, L. Hernandez, S. B. Shears, and J. E. Galan. 2001. A *Salmonella* inositol polyphosphatase acts in conjunction with other bacterial effectors to promote host cell actin cytoskeleton rearrangements and bacterial internalization. Mol Microbiol 39:248-259.

h. increased expression of at least one nucleic acid selected from the group consisting of sseL tlpA, and avrA and/or expression of at least one protein selected from the group consisting of Fas ligand (FasL) and tumor necrosis factor (TNF)-related apoptosis-inducing ligand (TRAIL).

2. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$.

3. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar.

4. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar, $\Delta P_{tsr}::P_{trc\ \Delta lacO}$ tsr.

5. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar, $\Delta P_{tsr}::P_{trc\ \Delta lacO}$ tsr, $\Delta trg$ or $\Delta P_{trg}::rhaRS\text{-}P_{rhaB}$ trg.

6. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$

What is claimed is:

1. A recombinant *Salmonella* bacterium, wherein the bacterium has:
   a. $\Delta P_{murA}::TT$ araC $P_{BAD}$ murA,
   b. at least one mutation selected from the group consisting of $\Delta P_{murA}::TT$ araC $P_{BAD}$ murA and $\Delta asdA::TT$ araC $P_{BAD}$ c2, and, optionally, at least one mutation selected from the group consisting of $\Delta(gmd\text{-}fcl)$ and $\Delta relA$,
   c. constitutive expression, from a constitutive promoter, of at least one nucleic acid selected from the group consisting of tar and tsr,
   d. a deletion or mutation to decrease expression of trg,
   e. constitutive expression, from a constitutive promoter, of hilA,
   f. at least one mutation selected from the group consisting of $\Delta purA$ and $\Delta(wza\text{-}wcaM)$,
   g. regulated delayed synthesis of at least one nucleic acid selected from the group consisting of sopE2 and sopB, and $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar, $\Delta P_{tsr}::P_{trc\ \Delta lacO}$ tsr, $\Delta trg$ or $\Delta P_{trg}::rhaRS\text{-}P_{rhaB}$ trg, $\Delta P_{hilA}::P_{trc\ \Delta lacO}$ hilA.

7. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar, $\Delta P_{tsr}::P_{trc\ \Delta lacO}$ tsr, $\Delta trg$ or $\Delta P_{trg}::rhaRS\text{-}P_{rhaB}$ trg, $\Delta P_{hilA}::P_{trc\ \Delta lacO}$ hilA, $\Delta purA$.

8. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta(araC\ P_{BAD})::P22\ P_R$ araBAD, $\Delta pagP::P_{lpp}$ lpxE, $\Delta endA$, $\Delta P_{tar}::P_{trc\ \Delta lacO}$ tar, $\Delta P_{tsr}::P_{trc\ \Delta lacO}$ tsr, $\Delta trg$ or $\Delta P_{trg}::rhaRS\text{-}P_{rhaB}$ trg, $\Delta P_{hilA}::P_{trc\ \Delta lacO}$ hilA, $\Delta purA$, $\Delta P_{sopE2}::P_{trc}$ sopE2.

9. A bacterium of claim 1, wherein the bacterium comprises the following mutations: $\Delta asdA::TT$ araC $P_{BAD}$ c2, $\Delta P_{murA}::TT$ araC $P_{BAD}$ murA, $\Delta(wza\text{-}wcaM)$, $\Delta relA::araC$ $P_{BAD}$ lacI TT, $\Delta$(araC $P_{BAD}$)::P22 $P_R$ araBAD, $\Delta$pagP::$P_{lpp}$ IpxE, $\Delta$endA, $\Delta P_{tar}$::$P_{trc\ \Delta lacO}$ tar, $\Delta P_{tsr}$::$P_{trc\ \Delta lacO}$ tsr, $\Delta$trg or $\Delta P_{trg}$::rhaRS-$P_{rhaB}$ trg, $\Delta P_{hilA}$::$P_{trc\ \Delta lacO}$ hilA, $\Delta$purA, $\Delta P_{sopE2}$::$P_{trc}$ sopE2, $\Delta P_{tlpA}$::$P_{ansB}$ tlpA.

10. A method of inhibiting tumor growth, the method comprising administering a recombinant bacterium of claim 1 to a tumor.

11. A method of treating cancer in a subject, the method comprising administering a recombinant bacterium of claim 1 to the subject, wherein the subject has cancer.

12. A recombinant *Salmonella* bacterium, wherein the bacterium has:
   a. constitutive expression, from a constitutive promoter, of Tar and Tsr, and
   b. elimination of expression of Trg.

13. A recombinant *Salmonella* bacterium, wherein the bacterium has:
   a. constitutive expression, from a constitutive promoter, of at least one nucleic acid selected from the group consisting tar and tsr,
   b. a deletion or mutation to prevent or decrease expression of trg,
   c. constitutive expression, from a constitutive promoter, of hilA,
   d. at least one mutation selected from the group consisting of $\Delta$purA and $\Delta$(wza-wcaM), and
   e. increased expression of at least one nucleic acid selected from the group consisting of sseL, tlpA, and avrA and/or a tumor specific DNA vaccine vector that expresses at least one protein selected from the group consisting of FasL and TRAIL.

14. The bacterium of claim 13, wherein the bacteria further has regulated delayed synthesis of at least one nucleic acid selected from the group consisting of sopE2 and sopB.

15. A recombinant *Salmonella* bacterium, wherein the bacterium comprises:
   a. $\Delta P_{tar}$::$P_{trc\ \Delta lacO}$ tar and $\Delta P_{tsr}$::$P_{trc\ \Delta lacO}$ tsr,
   b. $\Delta$trg or $\Delta P_{trg}$::rhaRS-$P_{rhaB}$ trg,
   c. $\Delta P_{hilA}$::$\Delta P_{trc\ \Delta lacO}$ hilA,
   d. $\Delta$(wza-wcaM) and, optionally, $\Delta$purA, and
   e. $\Delta P_{tlpA}$::$P_{ansB}$ tlpA or a tumor specific DNA vaccine vector to a tumor cell that expresses FasL.

16. The bacterium of claim 15, wherein the bacteria further comprises $\Delta P_{sopE2}$::$P_{trc}$ sopE2.

17. A recombinant *Salmonella* bacterium, wherein the bacterium comprises:
   a. constitutive expression, from a constitutive promoter, of at least one nucleic acid selected from the group consisting tar and tsr,
   b. deletion or mutation to decrease expression of trg,
   c. constitutive expression, from a constitutive promoter, of hilA,
   d. at least one mutation selected from the group consisting of $\Delta$purA and $\Delta$(wza-wcaM), and
   e. increased expression of at least one nucleic acid selected from the group consisting of sseL, tlpA, and avrA and/or a tumor specific DNA vaccine vector that expresses at least one protein selected from the group consisting of FasL and TRAIL.

18. The bacterium of claim 17, wherein the bacteria further comprises regulated delayed synthesis of at least one nucleic acid selected from the group consisting of sopE2 and sopB.

* * * * *

UNITED STATES PATENT AND TRADEMARK OFFICE
CERTIFICATE OF CORRECTION

PATENT NO. : 9,598,697 B2  
APPLICATION NO. : 13/700591  
DATED : March 21, 2017  
INVENTOR(S) : Roy Curtiss and Wei Kong Page 1 of 1

It is certified that error appears in the above-identified patent and that said Letters Patent is hereby corrected as shown below:

In the Specification

In Column 1, Line 04:
Delete the following paragraph:
"GOVERNMENTAL RIGHTS
This invention was made with government support under ROI AI065779, ROI AI056289, and R2I CAI52456-01 awarded by the National Institutes of Health. The government has certain rights in the invention."

Insert the following paragraph:
-- GOVERNMENT SUPPORT CLAUSE
This invention was made with government support under AI065779, AI056289, CA152456 awarded by the National Institutes of Health. The government has certain rights in the invention. --

Signed and Sealed this
Twenty-sixth Day of November, 2019

Andrei Iancu
*Director of the United States Patent and Trademark Office*